US009504738B2

(12) United States Patent
Pravin

(10) Patent No.: US 9,504,738 B2
(45) Date of Patent: Nov. 29, 2016

(54) IMMUNOGENIC EPITOPES, PEPTIDOMIMETICS, AND ANTI-PEPTIDE ANTIBODIES, AND METHODS OF THEIR USE

(71) Applicant: Ohio State Innovation Foundation, Columbus, OH (US)

(72) Inventor: Kaumaya Pravin, Westerville, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 435 days.

(21) Appl. No.: 13/662,024

(22) Filed: Oct. 26, 2012

(65) Prior Publication Data

US 2013/0216564 A1  Aug. 22, 2013

Related U.S. Application Data

(62) Division of application No. 12/700,388, filed on Feb. 4, 2010, now abandoned.

(51) Int. Cl.
| | |
|---|---|
| A61K 38/16 | (2006.01) |
| A61K 39/00 | (2006.01) |
| C07K 14/52 | (2006.01) |
| C07K 14/71 | (2006.01) |
| C07K 16/22 | (2006.01) |
| C07K 16/32 | (2006.01) |
| A61K 38/00 | (2006.01) |

(52) U.S. Cl.
CPC ........... *A61K 39/0011* (2013.01); *C07K 14/52* (2013.01); *C07K 14/71* (2013.01); *C07K 16/22* (2013.01); *C07K 16/32* (2013.01); *A61K 38/00* (2013.01); *A61K 2039/505* (2013.01); *A61K 2039/507* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 5,601,989 A | 2/1997 | Cheever et al. | 435/7.23 |
| 5,726,023 A | 3/1998 | Cheever et al. | 435/7.1 |
| 5,773,230 A | 6/1998 | Cheever et al. | 435/7.23 |
| 5,801,005 A | 9/1998 | Cheever et al. | 435/7.024 |
| 5,840,525 A | 11/1998 | Vandlen et al. | 435/69.1 |
| 5,846,538 A | 12/1998 | Cheever et al. | 424/185.1 |
| 5,869,445 A | 2/1999 | Cheever et al. | 514/2 |
| 5,876,712 A | 3/1999 | Cheever et al. | 424/93.7 |
| 6,015,567 A | 1/2000 | Hudziak et al. | 424/277.1 |
| 6,075,122 A | 6/2000 | Cheever et al. | 530/350 |
| 6,165,464 A | 12/2000 | Hudziak et al. | 424/131.1 |
| 6,339,139 B1 | 1/2002 | Gu et al. | 530/300 |
| 7,060,284 B1 | 6/2006 | Kaumaya et al. | 424/277.1 |
| 7,291,601 B1 * | 11/2007 | Chae | C07K 7/06 514/13.3 |
| 7,666,430 B2 | 2/2010 | Kaumaya et al. | 424/185.1 |
| 7,691,396 B2 | 4/2010 | Kaumaya et al. | 424/277.1 |
| 7,892,549 B2 | 2/2011 | Paton et al. | 424/143.1 |
| 8,080,253 B2 | 12/2011 | Kaumaya et al. | 424/192.1 |
| 8,110,657 B2 | 2/2012 | Kaumaya et al. | 560/326 |
| 2003/0170235 A1 | 9/2003 | Cohen et al. | 424/193.1 |
| 2003/0235594 A1 | 12/2003 | Humphreys et al. | 424/192.1 |
| 2005/0233964 A1 * | 10/2005 | Kaumaya et al. | 514/12 |
| 2006/0110400 A1 | 5/2006 | Glover et al. | 424/185.1 |
| 2006/0188976 A1 | 8/2006 | Takeshita et al. | 435/183 |
| 2010/0234283 A1 | 9/2010 | Kaumaya et al. | 514/9 |
| 2011/0086055 A1 | 4/2011 | Kaumaya et al. | 424/192.1 |
| 2012/0121626 A1 | 5/2012 | Kaumaya et al. | 424/192.1 |
| 2012/0201841 A1 | 8/2012 | Kaumaya et al. | 424/185.1 |

FOREIGN PATENT DOCUMENTS

| | | |
|---|---|---|
| AU | 2005213457 | 2/2005 |
| AU | 2006261342 | 6/2005 |
| AU | 2006261342 | 6/2006 |
| CA | 2555274 | 2/2005 |
| CA | 2612394 | 6/2005 |
| CA | 2612394 | 6/2006 |
| EP | 00953823 | 8/2000 |
| EP | 00953823.2 | 8/2000 |
| EP | 05722777 | 2/2005 |
| EP | 05722777.9 | 2/2005 |
| EP | 06785065.1 | 6/2005 |
| EP | 06785065 | 6/2006 |
| EP | 06785065.1 | 6/2006 |
| EP | 12170985 | 6/2012 |
| EP | 12170985.1 | 6/2012 |
| JP | 2001-513369 | 8/2000 |
| JP | 2003520781 | 7/2003 |

(Continued)

OTHER PUBLICATIONS

Muller et al ('The crystal structure of vascular endothelial growth factor (VEGF) refined to 1.93 A resolution: multiple copy flexibility and receptor binding' Structure v5 Oct. 15, 1997 pp. 1325-1338).*
Amici, A. et al, DNA vaccination with full-length or truncated neu induces protective immunity against the development of spontaneous mammary tumors in HER- 2/neu transgenic mice. Gene Ther, 2000. 7(8): p. 703-6.
Amici, A. et al, Genetic immunization against neulerbB2 transgenic breast cancer. Cancer Immunol Immunother, 1998. 47(4): p. 183-90.
Boocock et al., Expression of vascular endothelial growth factor and its receptors flt and KDR in ovarian carcinoma. J. Natl. Cancer Inst., 1995. 87: p. 506-516.
Cobleigh, M.A. et al., A phase III dose-escalation trial of bevacizumab in previously treated metastatic breast cancer. Semin Oncol, 2003. 30(5 Suppl16): p. 117-24.
Dakappagari, NK et al., Peptide Vaccine Strategies for Immunotherapy of HER-2,NEU Overexpressing Cancers. Americanc Peptide Symposium, 1999. Abstract P752.
Dakappagari, N.K. et al., A chimeric multi-human epidermal growth factor receptor-2 B cell epitope peptide vaccine mediates superior antitumor responses. J. Immunol, 2003. 170(8): p. 4242-53.

(Continued)

*Primary Examiner* — Christina Bradley
*Assistant Examiner* — Ronald Niebauer
(74) *Attorney, Agent, or Firm* — Meunier Carlin & Curfman LLC

(57) ABSTRACT

Provided herein are compositions and methods for the treatment of cancers. The compositions comprise at least one VEGF peptide mimic, HER-2 epitope, immunogenic VEGF peptides, and HER-2 immunogenic epitopes. The peptides and epitopes may be linear, cyclized, retro-inverso, or a combination of such forms. Also provided herein are antibodies raised to VEGF peptide mimics, HER-2 epitopes, immunogenic VEGF peptides, and HER-2 immunogenic epitopes.

20 Claims, 31 Drawing Sheets

(56) References Cited

FOREIGN PATENT DOCUMENTS

| JP | 2004522412 | 7/2004 |
|---|---|---|
| JP | 2008-517193 | 6/2005 |
| JP | 2012-93680 | 6/2005 |
| JP | 2008-517193 | 6/2006 |
| JP | 2012-93680 | 4/2012 |
| NZ | 564951 | 6/2005 |
| NZ | 564951 | 6/2006 |
| WO | WO 94/00153 | 1/1994 |
| WO | WO 94/07530 | 4/1994 |
| WO | WO 94/07531 | 4/1994 |
| WO | WO 95/17210 | 6/1995 |
| WO | WO 96/02555 | 2/1996 |
| WO | WO 96/33739 | 10/1996 |
| WO | WO 96/34888 | 11/1996 |
| WO | WO 97/38011 | 10/1997 |
| WO | WO 98/17797 | 4/1998 |
| WO | WO 99/31140 | 6/1999 |
| WO | WO 00/34337 | 6/2000 |
| WO | PCT/US2000/021222 | 8/2000 |
| WO | WO 01/08636 | 2/2001 |
| WO | WO 01/21193 | 3/2001 |
| WO | WO 02/14503 | 2/2002 |
| WO | WO 2004/030616 | 4/2004 |
| WO | WO 2004/30616 | 4/2004 |
| WO | WO 2004/078907 | 9/2004 |
| WO | WO 2004/113380 | 12/2004 |
| WO | PCT/US2005/003747 | 2/2005 |
| WO | WO 2005/039616 | 5/2005 |
| WO | PCT/US2006/023672 | 6/2005 |
| WO | WO 2005/076972 | 8/2005 |
| WO | WO 2006/138675 | 12/2006 |

OTHER PUBLICATIONS

Dakappagari, N.K. et al., Conformational HER-2/neu B-cell Epitope Peptide Vaccine Designed to Incorporate Two Native Disulfide Bonds Enhances Tumor Cell Binding and Antitumor Activities. J. Bioi Chern., 2005, 280(1): p. 54-63.

Dakappagari, N.K. et al., Intracellular delivery of a novel multiepitope peptide vaccine by an amphipathic peptide carrier enhances cytotoxic T-cell responses in HLA-A *201 mice. J Pept Res, 2005. 65(2): p. 189-99.

De Lorenzo, C. et al., A fully human antitumor immunoRNase selective for ErbB-2-positive carcinomas. Cancer Res, 2004. 64(14): p. 4870-4.

DelaCruz, J.S. et al., Protein vaccination with the HER2/neu extracellular domain plus anti-HER2/neu antibody-cytokine fusion proteins induces a protective anti-HER2/neu immune response in mice. Vaccine, 2003. 21(13-14): p. 1317-26.

Fendly, B.M. et al., Characterization of murine monoclonal antibodies reactive to either the human epidermal growth factor receptor or HER21neu gene product. Cancer Res, 1990. 50(5): p. 1550-8.

Ferrara, N., Vascular endothelial growth factor as a target for anticancer therapy. Oncologist, 2004. 9 Suppl1: p. 2-10.

Hopp et al., Prediction of protein antigenic determinants from amino acid sequences. Proc Natl Acad Sci, 1981. 78: p. 3824-3828.

Hynes, N.E. et al., The biology of erbB-2/neu/HER-2 and its role in cancer. Biochim Biophys Acta, 1994. 1198(2-3): p. 165-84.

Jain, R.K., Tumor angiogenesis and accessibility: role of vascular endothelial growth factor. Semin Oncol, 2002. 29(6 Suppl 16): p. 3-9.

Kim et al., Vascular endothelial growth factor proteins: Identification of biologically relevant regions by neutralizing monoclonal antibodies. Growth Factors, 1992. 7: p. 53-64.

Kumagai, T. et al., Role of extracellular subdomains of p 185c-neu and the epidermal growth factor receptor in ligandindependent association and transactivation. Proc Natl Acad Sci U S A, 2003. 1 00(16): p. 9220-5.

Le, X.F. et al., Roles of human epidermal growth factor receptor 2, c-jun NH2-terminal kinase, phosphoinositide 3-kinase, and p70 S6 kinase pathways in regulation of cyclin G2 expression in human breast cancer cells. Molecular Cancer Therapeutics, 2007, 6: 2843-2857.

LeCouter et at., Identification of an angiogenic mitogen selective for endocrine gland endothelium. Nature, 2001. 412: p. 877-884.

Lewis, G.D. et al., Differential responses of human tumor eel/lines to anti-p 185HER2 monoclonal antibodies. Cancer Immunol Immunother, 1993. 37(4): p. 255-63.

Markman et al., Phase III randomized trial of 12 versus 3 months of maintenance paclitaxel in patients with advanced ovarian cancer after complete response to platinum and paclitaxel-based chemotherapy: a Southwest Oncology Group and Gynecologic Oncology Group trial. J Clin Oncol, 2003. 21: p. 2460-5.

McGuire et al., Cyclophosphamide and cisplatin compared with paclitaxel and cisplatin in patients with stage III and stage IV ovarian cancer. N Engl J Med, 1996. 334: p. 1-6.

Nair, S. et al., Synergy between tumor immunotherapy and antiangiogenic therapy. Blood, 2003. 102(3): p. 964-71.

Pal, D. et al., Beta-Sheet propensity and its correlation with parameters based on conformation. Acta Crystallographica Section D, 2000. D56: pp. 589-594.

Perez, S.A. et al., HER-2/neu-derived peptide 884-899 is expressed by human breast, colorectal and pancreatic adenocarcinomas and is recognized by in-vitro-induced specific CD4(+) T cell clones. Cancer Immunol Immunother, 2002. 50(11): p. 615-24.

Samuelsson, A. et al., Anti-inflammatory activity of IVIG mediated through the inhibitory Fe receptor. Science, 2001. 291 (5503): p. 484-6.

Sotiriadou, R. et al., Peptide HER2(776-788) represents a naturally processed broad Mhc class II-restricted T cell epitope. Br J Cancer, 2001. 85(10): p. 152-734.

Spiridon, C. I. et al., A comparison of the in vitro and in vivo activities of IgG and Fab2 fragments of a mixture of three monoclonal anti-Her-2 antibodies. Chin Cancer Res, 2004. 10(10): p. 3542-51.

Tuttle, T.M. et at., Proliferative and cytokine responses to class II HER- 2/neuassociated peptides in breast cancer patients. Clin Cancer Res, 1998. 4(8): p. 2015-24.

Wagner et al., Immunological Consolidation of Ovarian Carcinoma Recurrences with Monoclonal Anti-Idiotype Antibody ACA125: Immune Responses and Sruvival in Palliative Treatment. Clinical Cancer Research, 2001. 7: p. 1154-1162.

Preliminary Amedment filed Apr. 12, 2010 for European application No. 06785065.1, which claims priority to PCT/US2006/023672 filed on Jun. 15, 2006 (Applicant—The Ohio State University Research Foundation// Inventor—Kaumaya et at.) (8 pages).

Withdrawl of application issued May 6, 2011 for European application No. 06785065.1. , which claims priority to PCT/US2006/023672 filed on Jun. 15, 2006—(Applicant—The Ohio State University Research Foundation// Inventor—Kaumaya et al.) (2 pages).

Request for further processing filed Jul. 18, 2011 for European application No. 06785065.1 , which claims priority to PCT/US2006/023672 filed on Jun. 15, 2006—(Applicant—The Ohio State University Research Foundation// Inventor—Kaumaya et al.) (8 pages).

Decision to allow further processing issued Sep. 7, 2011 for European application No. 06785065.1, which claims priority to PCT/US2006/023672 filed on Jun. 15, 2006—(Applicant—The Ohio State University Research Foundation// Inventor—Kaumaya et al.) (1 page).

Office Action issued on Dec. 22, 2011 for European application No. 06785065.1 filed on, which claims priority to PCT/US2006/023672 filed on Jun. 15, 2006 (Applicant—The Ohio State University Research Foundation// Inventor—Kaumaya et al.) (3 pages).

Office Action issued Oct. 17, 2011 for Japanese application No. 2008-517193 , which claims priority to PCT/US2006/023672 filed on Jun. 15, 2006 (Applicant—The Ohio State University Research Foundation//Inventor—Kaumaya et al.) (12 pages).

Response to office action filed Apr. 17, 2012 for Japanese application No. 2008-517193 , which claims priority to PCT/US2006/023672 filed on Jun. 15, 2006 (Applicant—The Ohio State University Research Foundation// Inventor—Kaumaya et al.) (6 pages).

(56) References Cited

OTHER PUBLICATIONS

International preliminary report on patentability issued Dec. 17, 2009 for PCT/US2006/23672 filed Jun. 15, 2006 (Applicant—The Ohio State University Research Foundation// Inventor—Kaumaya et al.) (5 pages).
Non-final Office Action issued Apr. 15, 2008 for U.S. Appl. No. 11/424,526, filed Jun. 15, 2006 (Inventor—Kaumaya et al.) (19 pages).
Response to Office Action filed Oct. 15, 2008 for U.S. Appl. No. 11/424,526, filed Jun. 15, 2006 (Inventor—Kaumaya et al.) (14 pages).
Response to Office Action and Terminal Disclaimer filed Jul. 27, 2012 for U.S. Appl. No. 12/697,578, filed Feb. 1, 2010 (Inventor—Kaumaya et al.) (7 pages).
Response to restriction requirement filed Dec. 9, 2002 for U.S. Appl. No. 09/632,036, filed on Aug. 3, 2000 (Inventor—Kaumaya et al.) (1 page).
Miscellaneous Action issued Feb. 26, 2003 for U.S. Appl. No. 09/632,036, filed on Aug. 3, 2000 (Inventor—Kaumaya et al.) (2 pages).
Response to Miscellaneous Action issued Mar. 31, 2003 for U.S. Appl. No. 09/632,036, filed Aug. 3, 2000 (Inventor—Kaumaya et al.) (2 pages).
Restriction requirement issued Aug. 6, 2003 for U.S. Appl. No. 09/632,036, filed Aug. 3, 2000 (Inventor—Kaumaya et al.) (13 pages).
Response to restriction requirement filed Dec.10, 2003 for U.S. Appl. No. 09/632,036, filed Aug. 3, 2000 (Inventor—Kaumaya et al.) (2 pages).
Response to Notice of Non-complient amendment issued Jun. 24, 2005 for U.S. Appl. No. 09/632,036, filed on Aug. 3, 2000 (Inventor—Kaumaya et al.) (21 pages).
Response to Office Action filed Aug. 26, 2011 for U.S. Appl. No. 12/683,114, filed on Jan. 6, 2010 (Inventor—Kaumaya et al.) (11 pages).
Preliminary Amendment filed May 8, 2002 for European application No. 00953823.2, which claims priority to PCT/US2000/021222 filed on Aug. 3, 2000 (Applicant—The Ohio State University Research Foundation// Inventor—Kaumaya et at.) (18 pages).
Supplementary European Search Report issued Aug. 10, 2004 for European application No. 00953823.2, which claims priority to PCT/US2000/021222 filed on Aug. 3, 2000—(Applicant—The Ohio State University Research Foundation// Inventor—Kaumaya et al.) (7 pages).
Application deemed withdrawn May 17, 2010 for European application No. 00953823.2, which claims priority to PCT/US2000/021222 filed on Aug. 3, 2000 (Applicant—The Ohio State University Research Foundation// Inventor—Kaumaya et al.) (1 page).
Telephone communication with Office Dec. 28, 2011 for European application No. 00953823.2, which claims priority to PCT/US2000/021222 filed on Aug. 3, 2000 (Applicant—The Ohio State University Research Foundation// Inventor—Kaumaya et al.) (3 pages).
Telephone communication with Office Sep. 4, 2012 for European application No. 00953823.2, which claims priority to PCT/US2000/021222 filed on Aug. 3, 2000 (Applicant—The Ohio State University Research Foundationfi Inventor—Kaumaya et al.) (4 pages).
Office Action issued Apr. 15, 2009 for U.S. Appl. No. 11/052,721, filed Feb. 7, 2005 (Inventor—Kaumaya et a1.) (8 pages).
Response to Office Action filed May 20, 2010 for U.S. Appl. No. 11/052,721, filed Feb. 7, 2005 (Inventor—Kaumaya et al.) (10 pages).
Response to Restriction Requirement filed May 29, 2012 for U.S. Appl. No. 13/331,891, filed Dec. 20, 2011 (Inventor—Kaumaya et a1.) (6 pages).
Response to Invitation to correct deficientcies filed Aug. 24, 2009 for European application No. 05722777.9, which claims priority to PCT/US2005/003747 filed on Feb. 7, 2005 (Applicant—The Ohio State University Research Foundationfi Inventor—Kaumaya et al.) (3 pages).
Communication from Examining Division issued May 27, 2010 for European application No. 05722777.9, which claims priority to PCT/US2005/003747 filed on Feb. 7, 2005 (Applicant—The Ohio State University Research Foundationfi Inventor—Kaumaya et al.) (5 pages).
Request to allow further processing filed Mar. 16, 2011 for European application No. 05722777.9, which claims priority to PCT/US2005/003747 filed on Feb. 7, 2005 (Applicant—The Ohio State University Research Foundation// Inventor—Kaumaya et al.) (9 pages).
Communication from Examining Division issued Oct. 28, 2011 for European application No. 05722777.9, which claims priority to PCT/US2005/003747 filed on Feb. 7, 2005 (Applicant—The Ohio State University Research Foundation// Inventor—Kaumaya et al.) (4 pages).
Response to Communication from Examining Division filed Mar. 7, 2012 for European application No. 05722777.9, which claims priority to PCT/US2005/003747 filed on Feb. 7, 2005 (Applicant—The Ohio State University Research Foundation// Inventor—Kaumaya et al.) (27 pages).
Non-Final Office Action issued on May 12, 2015 for U.S. Appl. No. 13/905,996, filed May 30, 2013 and published as US-2014-0010831-A1 on Jan. 9, 2014 (Inventor—Kaumaya, et al. // Applicant—The Ohio State University) (8 pages).
U.S. Appl. No. 13/905,996, filed May 30, 2013, Kaumaya.
U.S. Appl. No. 60/690,574, filed Jun. 15, 2006, Pravin T.P. Kaumaya.
U.S. Appl. No. 11/424,526 (U.S. Pat. No. 7,691,396), filed Jun. 15, 2006, Pravin T.P. Kaumaya.
U.S. Appl. No. 12/697,578, filed Feb. 1, 2010, Pravin T.P. Kaumaya.
U.S. Appl. No. 60/146,869, filed Aug. 3, 1996, Pravin T.P. Kaumaya.
U.S. Appl. No. 09/632,036 (U.S. Pat. No. 7,060,284), filed Aug. 3, 2000, Pravin T.P. Kaumaya.
U.S. Appl. No. 11/423,194 (U.S. Pat. No. 7,666,430), filed Jun. 9, 2006, Pravin T.P. Kaumaya.
U.S. Appl. No. 12/683,114 (U.S. Pat. No. 8,110,657), filed Jan. 6, 2010, Pravin T.P. Kaumaya.
U.S. Appl. No. 13/366,546, filed Feb. 6, 2012, Pravin T.P. Kaumaya.
U.S. Appl. No. 11/052,721 (U.S. Pat. No. 8,080,253), filed Feb. 7, 2005, Pravin T.P. Kaumaya.
U.S. Appl. No. 13/331,891, filed Dec. 20, 2011, Pravin T.P. Kaumaya.
U.S. Appl. No. 61/149,959, filed Feb. 4, 2009, Pravin T.P. Kaumaya.
U.S. Appl. No. 12/700,388, filed Feb. 4, 2010, Pravin T.P. Kaumaya.
Abe, Y. et al., Disulfide bond structure of humanepidermal growth factor receptor. J Biol Chem, 1998. 273(18): p. 11150-7.
Agus, D.B. et al., Phase I Clinical Study of Pertuzumab, a Novel HER Dimerization Inhibitor, in Patients With Advanced Cancer. J Clin Oncol, 2005. 23(11): p. 2534-43.
Agus, D.B. et al., Targeting ligand-activated ErbB2 signaling inhibits breast and prostate tumor growth. Cancer Cell, 2002. 2(2): p. 127-37.
Allred, D.C. et al., Overexpression of HER-2/neu and its relationship with other prognostic factors change during the progression of in situ to invasive breast cancer. Hum Pathol, 1992. 23(9): p. 974-9.
Amici, A. et al, DNA vaccination with full-length or truncated neu induces protective immunity against the development of spontaneous mammary tumors in HER-2/neu transgenic mice. Gene Ther, 2000. 7(8): p. 703-6.
Amici, A. et al, Genetic immunization against neulerbB2 transgenic breast cancer. Cancer Immunol lmmunother, 1998. 47(4): p. 183-90.
Baselga, J., et al., Phase II study of weekly intravenous recombinant humanized anti-p185HER2 monoclonal antibody in patients with HER2/neu-overexpressing metastatic breast cancer. J. Clin. Oncol. 14:737-44, 1996.
Baxevanis, C.N. et al., Tumor-specific CD4+ T lymphocytes from cancer patients are required for optimal induction of cytotoxic T cells against the autologous tumor. J Immunol, 2000. 164(7): p. 3902-12.
Bennasroune, A. et al., Transmembrane Peptides as Inhibitors of ErbB Receptor Signaling. Mol. Bioi. Cell, 2004. 15(7): p. 3464-3474.

(56) References Cited

OTHER PUBLICATIONS

Berchuck, A. et al., Overexpression of HER-2/neu is associated with poor survival in advanced epithelial ovarian cancer. Cancer Res, 1990. 50(13): p. 4087-91.
Berezov, A. et al., Disabling receptor ensembles with rationally designed interface peptidomimetics. J Bioi Chem, 2002. 277(31): p. 28330-9.
Berezov, A. et al., Structure-based approaches to inhibition of erbB receptors with peptide mimetics. Immunol Res, 2003. 27(2-3): p. 303-8.
Bernards, R., et al., Effective tumor immunotherapy directed against an oncogene-encoded product using a vaccinia virus vector. Proc. Natl. Acad. Sci. USA, 84:6854-8, 1987.
Binetruy-Tournaire, R. et al., Identification of a peptide blocking vascular endothelial growth factor (VEGF)-mediated angiogenesis. Embo J, 2000. 19(7): p. 1525-33.
Boggio, K. et al., Ability of systemic inter/eukin-12 to hamper progressive stages of mammary carcinogenesis in HER2/neu transgenic mice. Cancer Res, 2000. 60(2): p. 359-64.
Boggio, K. et al., Interleukin 12-mediated prevention of spontaneous mammary adenocarcinomas in two lines of Her-2/neu transgenic mice. J Exp Med, 1998. 188(3): p. 589-96.
Boocock et al., Expression of vascular endothelial growth factor and its receptors fit and KDR in ovarian carcinoma. J. Natl. Cancer Inst., 1995. 87: p. 506-516.
Bowie, J.U. et al., Deciphering the message in protein sequences: Tolerance to amino acid substitutions. Science, 1990. 247: p. 1306-1309.
Carmeliet, P. et al., Angiogenesis in cancer and other diseases. Nature, 2000. 407(6801): p. 249-57.
Cefai, D. et al., Targeting HER-2/neu for active-specific immunotherapy in a mouse model of spontaneous breast cancer. Int J Cancer, 1999. 83(3): p. 393-400.
Chang, S.Y. et al., Enhanced efficacy of DNA vaccination against Her-2/neu tumor antigen by genetic adjuvants. Int J Cancer, 2004. 111 (1): p. 86-95.
Chen et al., Monoclonal antibodies against vascular endothelial growth factor165 ($VEGF_{165}$): Neutralization of biological activity and recognition of the epitope. Biochemistry and Molecular Biology International, 1999. 47(2): p. 161-169.
Cho, H.S. et al., Structure of the extracellular region of HER2 alone and in complex with the Herceptin Fa b. Nature, 2003. 421(6924): p. 756-60.
Chorev, M. et al., Recent developments in retro peptides and proteins-an ongoing topochemical exploration. Trends Biotechnol, 1995. 13(10): p. 438-45.
Chou et al., Prediction of the secondary structure of proteins from their amino acid sequence. Adv Enzymol Relat Subj Biochem, 1978. 47: p. 45-148.
Choudhury, A. et at., Small interfering RNA (siRNA) inhibits the expression of the Her2/neu gene, upregulates HLA class I and induces apoptosis of Her2/neu positive tumor eel/lines. Int J Cancer, 2004. 108(1): p. 71-7.
Cifaldi, L. et al., A light, nontoxic interleukin 12 protocol inhibits HER-2/neu mammary carcinogenesis in BALB/c transgenic mice with established hyperplasia. Cancer Res, 2001. 61(7): p. 2809-12.
Clynes, R.A. et al., Inhibitory Fe receptors modulate in vivo cytoxicity against tumor targets [see comments]. Nature Medicine, 2000. 6(4): p. 443-6.
Cobleigh, M.A. et al., A phase III dose-escalation trial of bevacizumab in previously treated metastatic breast cancer. Semin Oncol, 2003. 30(5 Suppl16): p. 117-24.
Cole et al., The EBV-Hybridoma Technique and its application to human lung cancer. Monoclonal Antibodies and Cancer Therapy, 1985. p. 77-96.
Cuadros, C. et al., Cooperative effect between immunotherapy and antiangiogenic therapy leads to effective tumor rejection in tolerant Her-2/neumice. Cancer Res, 2003. 63(18): p. 5895-901.

Dakappagari, NK et al., Peptide Vaccine Strategies for Immunotherapy of HER-2/NEU Overexpressing Cancers. Americanc Peptide Symposium, 1999. Abstract P752.
Dakappagari, N.K. et al., Prevention of mammary tumors with a chimeric HER-2 B-cell epitope peptide vaccine. Cancer Res, 2000. 60(14): p. 3782-9.
Dakappagari, N.K. et al., Evalution of Chimeric B-Cell Epitope of HER-2: Application to Cancer Patients. Dissertation at Ohio State University, 2001.
Dakappagari, N.K. et al., Evaluation of synergistic interaction between cytokines and peptide epitope vaccines in protection against Her-2 expressing lung metastases. American Peptide Symposium, 2001. Abstract P1012.
Dakappagari, N.K. et al., A chimeric multi-human epidermal growth factor receptor-2 B cell epitope peptide vaccine mediates superior antitumor responses. J Immunol, 2003. 170(8): p. 4242-53.
Dakappagari, N.K. et al., Conformational HER-2/neu B-cell Epitope Peptide Vaccine Designed to Incorporate Two Native Disulfide Bonds Enhances Tumor Cell Binding and Antitumor Activities. J Bioi Chern, 2005. 280(1): p. 54-63.
Dankort, D. et al., Grb2 and Shc adapter proteins play distinct roles in Neu (ErbB-2)-induced mammary tumorigenesis: implications for human breast cancer. Mol Cell Bioi, 2001. 21 (5): p. 1540-51.
De Giovanni, C. et al., Immunoprevention of HER-2/neu transgenic mammary carcinoma through an interleukin 12-engineered allogeneic cell vaccine. Cancer Res, 2004, 64(11): p. 4001-9.
De Groot et al., Developing an epitope-driven tuberculosis (TB) vaccine. J Vaccine, 2005. 23(17-18): 2121-31.
De Lorenzo, C. et al., A fully human antitumor immunoRNase selective for ErbB-2-positive carcinomas. Cancer Res, 2004. 64(14): p. 4870-4.
DelaCruz, J.S. et al., Protein vaccination with the HER2/neu extracellular domain plus anti-HER2/neu antibody-cytokine fusion proteins induces a protective anti-HER2/neu immune response in mice. Vaccine, 2003. 21(13- 14): p. 1317-26.
Deulofeut et al., Cellular recognition and HLA restriction of a midsequence HBsAg peptide in hepatitis B vaccinated individuals. Mol Immunol, 1993. 30: p. 941-948.
DiCarlo, E. et al., Analysis of mammary carcinoma onset and progression in HER-2/neu oncogene transgenic mice reveals a lobular origin. Lab Invest, 1999. 79(10): p. 1261-9.
Disis, M.L. et al., Existent T-cell and antibody immunity to HER-2/neu protein in patients with breast cancer. Cancer Res, 1994. 54(1): p. 16-20.
Disis, M.L. et al., Immunization of oncogenic HER-s/neu protein with peptide based vaccines. Proceedings of the Annual Meeting of the American Association for Cancer Research, 1995. 36: p. 251.
Disis, M.L. et al., Peptide-based, but not whole protein, vaccines elicit immunity to HER-2/neu, oncogenic self-protein. J Immunol, 1996. 156(9): p. 3151-8.
Disis, M.L. et al., Granulocyte-Macrophage colony stimulating factor: An effective adjuvant for protein and peptide-based vaccines. Blood, 1996. 88(1): p. 202-210.
Disis, M.L. et al., Generation of immunity to the HER-2/ neuoncogenic protein in patients with breast and ovarian cancer using a peptide-based vaccine. Clin Cancer Res, 1999. 5(6): p. 1289-97.
Disis, M.L. et al., High-titer HER-2/neu protein-specific antibody can be detected in patients with early-stage breast cancer. J Clin Oncol, 1997. 15(11): p. 3363-7.
Drebin, J.A. et al., Inhibition of tumor growth by monoclonal antibody reactive with an oncogene-encoded tumor antigen. Proc Natl Acad Sci, 1986. 83: p. 9129-9133.
Drebin, J.A. et al., Monoclonal antibodies reactive with distinct domains of the neu oncogene-encoded p185 molecule exert synergistic anti-tumor effects in vivo. Oncogene, 1988. 2(3): p. 273-7.
Drebin, J.A. et al., Monoclonal antibodies specific for the neu oncogene product directly mediate anti-tumor effects in vivo. Oncogene, 1988. 2(4): p. 387-394.
Ei-Mousawi, M. et al., Alakhov, A vascular endothelial growth factor high affinity receptor 1-specific peptide with antiangiogenic activity identified using a phage display peptide library. J Bioi Chern, 2003. 278(47): p. 46681-91.

(56) References Cited

OTHER PUBLICATIONS

Esserman, L. J. et al., Vaccination with the extracellular domain p185neu prevents mammary tumor development in neu transgenic mice. Cancer Immunol. Immunother., 1999. 47:337-42.

Fairbrother, W.J. et al., Novel peptides selected to bind vascular endothelial growth factor target the receptor-binding site. Biochemistry, 1998. 37(51): p. 17754-64.

Fendly, B.M. et al., Characterization of murine monoclonal antibodies reactive to either the human epidermal growth factor receptor or HER2lneu gene product. Cancer Res, 1990. 50(5): p. 1550-8.

Ferrara, N. et al., Pituitary follicular cells secrete a novel heparin-binding growth factor specific for vascular endothelial cells. Biochem Biophys Res Commun, 1989. 161(2): p. 851-8.

Ferrara, N. et al., Discovery and development of bevacizumab, an anti-VEGF antibody for treating cancer. Nat Rev Drug Discov, 2004. 3(5): p. 391-400.

Ferrara, N., Vascular endothelial growth factor as a target for anticancer therapy. Oncologist, 2004. 9 Suppll: p. 2-10.

Ferrara, N., Vascular endothelial growth factor: basic science and clinical progress. Endocr Rev, 2004. 25(4): p. 581-611.

Ferrara, N., Vascular endothelial growth factor and age-related macular degeneration: from basic science to therapy. Nature Medicine, 2010. 16(10): p. 1107-1111.

Fisk, B. et al., Existent proliferative responses of peripheral blood mononuclear cells from healthy donors and ovarian cancer patients to HER-2 peptides. Anticancer Res, 1997. 17(1A): p. 45-53.

Fisk, B. et al., Identification of an immunodominant peptide of HER-2/neu protooncogene recognized by ovarian tumor-specific cytotoxic T lymphocyte lines. J Exp Med, 1995. 181(6): p. 2109-17.

Franovic, A. et al., Human cancers converge at the HIF-2α oncogenic axis. Proc. Natl. Acad. Sci., 2009. 106(50): 21306-21311.

Frangione-Beebe et al., Enhanced immunogenicity of a conformational epitope of human T-lymphotropic virus type 1 using a novel chimeric peptide. Vaccine, 2001. 19: p. 1068-1081.

Franklin, M.C. et al., Insights into ErbB signaling from the structure of the ErbB2-pertuzumab complex. Cancer Cell, 2004. 5(4): p. 317-28.

Gan, Y.H. et al., Antitumour immunity of Bacillus CalmetteGuerin and interferon alpha in murine bladder cancer. European Journal of Cancer, 1999. 35(7): p. 1123-9.

Garrett, T.P. et al., Crystal structure of a truncated epidermal growth factor receptor extracellular domain bound to transforming growth factor alpha. Cell, 2002. 110(6): p. 763-73.

Garrett, T.P. et al., The crystal structure of a truncated ErbB2 ectodomain reveals an active conformation, poised to interact with other ErbB receptors. Mol Cell, 2003. 11 (2): p. 495-505.

Gentz et al., Bioassay for trans-activation using purified human immunodeficiency virus tat-encoded protein: Trans-activation requires mRNA synthesis. Proc Natl Acad Sci, 1989. 86: p. 821-824.

Goodman, M. et al., Topochemical design of bioactive peptides and peptidomimetics. Bioorg Khim, 1992. 18(10-11): p. 1375-93.

Gordon et al., Phase I safety and pharmacokinetic study of recombinant human anti-vascular endothelial growth factor in patients with advanced cancer. J Clin Oncol, 2001. 19: p. 843-850.

Gu, X. G., et al., A novel hydrophobized polysaccharide/oncoprotein complex vaccine induces in vitro and in vivo cellular and humoral immune responses against HER-2-expressing murine sarcomas. Cancer Res., 58: 3385-90, 1998.

Guy, C.T. et al., Expression of the neu protooncogene in the mammary epithelium of transgenic mice induces metastatic disease. Proc Natl Acad Sci U S A, 1992. 89(22): p. 1 0578-82.

Hanahan et al., Patterns and emerging mechanisms of the angiogenic switch during tumorogenesis. Cell, 1996. 86: p. 853-864.

Harwerth, I.M. et al., Monoclonal antibodies directed to the erbB-2 receptor inhibit in vivo tumour cell growth. Br J Cancer, 1993. 68(6): p. 1140-5.

Hennighausen, L. et al., Mouse models for breast cancer. Oncogene, 2000. 19(8): p. 966-7.

Heroult, M. et al., Heparin affin regulatory peptide binds to vascular endothelial growth factor (VEGF) and inhibits VEGF-induced angiogenesis. Oncogene, 2004. 23(9): p. 17 45-53.

Herrera et al., Antigenicity and immunogenicity of multiple antigen peptides (MAP) containing P. vivax CS epitopes in Aotus monkeys. Parasite Immunology, 1997. 19: p. 161-170.

Hetian, L. et al., A novel peptide isolated from a phage display library inhibits tumor growth and metastasis by blocking the binding of vascular endothelial growth factor to its kinase domain receptor. J Bioi Chern, 2002. 277(45): p. 43137-42.

Hoeben, A. et al., Vascular endothelial growth factor and angiogenesis. Pharmacol Rev, 2004. 56(4): p. 549-80.

Holash, J. et al., VEGF-Trap: a VEGF blocker with potent antitumor effects. Proc Nati Acad Sci U S A, 2002. 99(17): p. 11393-8.

Hollingsworth et al., Tumor angiogenesis in advanced stage ovarian carcinoma. Am J Pathol, 1995. 147: p. 33-41.

Hopp et al., Prediction of protein antigenic determinants from amino acid sequences. Proc Nati Acad Sci, 1981. 78: p. 3824-3828.

Houck, K.A. et al, The vascular endothelial growth factor family: identification of a fourth molecular species and characterization of alternative splicing of RNA. Mol Endocrinol, 1991. 5(12): p. 1806-14.

Hudziak, R.M. et al., p185HER2 monoclonal antibody has anti proliferative effects in vitro and sensitizes human breast tumor cells to tumor necrosis factor. Mol Cell Bioi, 1989. 9(3): p. 1165-72.

Hynes N.E. et al., The biology of erbB-2/neu/HER-2 and its role in cancer. Biochim Biophys Acta, 1994. 1198(2-3): p. 165-84.

Izumi, Y. et al., Tumour biology: herceptin acts as an antiangiogenic cocktail. Nature, 2002. 416(6878): p. 279-80.

Jain, R.L., Tumor angiogenesis and accessibility: role of vascular endothelial growth factor. Semin Oncol, 2002. 29(6 Suppl 16): p. 3-9.

Jasinska, J. et al., Inhibition of tumor cell growth by antibodies induced after vaccination with peptides derived from the extracellular domain of Her-2/neu. Int J Cancer, 2003. 107(6): p. 976-83.

Jemal et al., Cancer Statistics, 2003. CA Cancer J Clin, 2003. 53: p. 5-26.

Jiang et al., The immunogenicity of peptide versus DNA vaccine of an HER-2 CTL Epitope for breast and ovarian cancers. American Peptide Symposium, 1999. Abstract P751.

Jiang et al., Evaluation of the immunogenicity of peptide and DNA constructs for HER-2/neu epitopes. Peptides for the New Millennium (Editors: Fields, GB, Tam, TP and Batany), Kluwer Acadmeic Publisher, 2000. p. 695-696.

Jiang, B. et al., A Novel Peptide Isolated from a Phage Display Peptide Library with Trastuzumab Can Mimic Antigen Epitope of HER-2. J Bioi Chern, 2005. 280(6): p. 4656-62.

Karplus et al., Prediction of chain flexibility in proteins, a tool for the selection of peptide antigens. Naturwiss, 1985. 72: p. 212-213.

Kasprzyk, P.G. et al., Therapy of an animal model of human gastric cancer using a combination of anti-erbB-2 monoclonal antibodies. Cancer Research, 1992. 52(10): p. 2771-6.

Kaumaya et al., Synthesis and biophysical characterization of engineered topographic immunogenic determinants with aa topology. Biochemistry, 1990. 29: p. 13-23.

Kaumaya et al., Peptide Vaccines incorporating a "promiscuous" T-cell epitope bypass certain halotype restricted immune responses and provide broad spectrum immunogenicity. Journal of Molecular Recognition, 1993. 6: p. 81-94.

Kaumaya, P.T.P. et al., Denovo Engineering of Protein Immunogenic & Antigenic Determinants., in Peptides, G.M.B. Anantharamaiah, C., Editor. 1994, Springer-Verlag. p. 133-164.

Kaumaya et al., "Synthetic Peptides: Dream or Reality." Published in Peptides in Immunology, Wiley and Sons, Ltd. (1996).

Kaumaya et al., A combination of HER-2 peptide epitope vaccines mediate superior biological effects. American Peptide Symposium, 2001. Abstract P1004.

Kaumaya et al., HER-2/neu cancer vaccines: Present status and Future. International Journal of Peptide Research and Therapeutics, 2006. 12(1): p. 65-77.

Kawashima et al., Identification of HLA-A3-restricted cytotoxic T lymphocyte epitopes from Carcinoembryonic Antigen and HER-2/

(56) References Cited

OTHER PUBLICATIONS neu by primary in vitro immunization with peptide-pulsed dendritic cells. Cancer Research, 1999. 59: p. 431-435.
Ke, N. et al., One-week 96-we/1 soft agar growth assay for cancer target validation. Biotechniques, 2004. 36(5): p. 826-8, 830, 832-3.
Kelly et al., T-cell, adhesion, and B-cell epitopes of the cell surface *Streptococcus mutans* protein antigen I/II. Infection and Immunity, 1995. 63(9): p. 3649-3658.
Kerbel, R. et al., Clinical translation of angiogenesis inhibitors. Nat Rev Cancer, 2002. 2(10): p. 727-39.
Kern, J.A. et al., p185neu expression in human lung adenocarcinomas predicts shortened survival. Cancer Res, 1990. 50(16): p. 5184-7.
Kim et al., Vascular endothelial growth factor proteins: Identification of biologically relevant regions by neutralizing monoclonal antibodies. Growth Factors, 1992. 7: p.53-64.
Kim et al., Inhibtion of vascular endothelial growth vactor-induced angiogenesis suppresses tumor growth in vivo. Nature, 1993. 326: p. 841-844.
Kim, J.Y. et al., The role of ErbB2 signaling in the onset of terminal differentiation of oligodendrocytes in vivo. J Neurosci, 2003. 23(13): p. 5561-71.
Kobayashi, H. et al., Defining promiscuous MHC class II helper T-ee// epitopes for the HER2/neu tumor antigen. Cancer Res, 2000. 60(18): p. 5228-36.
Kobs-Conrad et al., Engineered topographic determinants with aB, BaB, and BaBa topologies show high affinity binding to native protein antigen (Lactate Dehydrogenase-C4). The Journal of Biological Chemistry, 1993. 268(34): p. 25285-25295.
Kohler et al., Continuous cultures of fused cells secreting antibody of predefined specificity. Nature, 1975. 256: p. 495-497.
Konecny, G.E. et al., Association between HER-2/neu and vascular endothelial growth factor expression predicts clinical outcome in primary breast cancer patients. Clin Cancer Res, 2004. 1 0(5): p. 1706-16.
Kono et al., Identification of HER-2/neu-derived peptide epitopes recognized by gastric cancer-specific cytotoxic T lymphocytes. Int. J. Cancer, 1998. 78: p. 202-208.
Kostler, W.J. et al., Single-agent trastuzumab versus trastuzumab plus cytotoxic chemotherapy in metastatic breast cancer: a single-institution experience. Anticancer Drugs, 2005. 16(2): p. 185-190.
Kozbor et al., The production of monoclonal antibodies from human lymphocytes. Immunology Today, 1983. 4: p. 72-79.
Kremer, C. et al., Up-regulation offlk-1/vascular endothelial growth factor receptor 2 by its ligand in a cerebral slice culture system. Cancer Res, 1997. 57(17): p. 3852-9.
Krishan, A., Rapid flow cytofluorometric analysis of mammalian cell cycle by propidium iodide staining J Cell Bioi, 1975. 66(1): p. 188-93.
Kumagai, T. et al., Role of extracellular subdomains of p. 185c-neu and the epidermal growth factor receptor in ligandindependent association and transactivation. Proc Nati Acad Sci U S A, 2003. 1 00(16): p. 9220-5.
Kuo, C.J. et al., Comparative evaluation of the antitumor activity of antiangiogenic proteins delivered by gene transfer. Proc Nati Acad Sci U S A, 2001. 98(8): p. 4605-10.
Kyngas, J. et al., Unreliability of the Chou-Fasman parameters in predicting protein secondary structure. Protein Engineering, 1998. 11(5): pp. 345-348.
Lairmore, M.D. et al., Human T-lymphotropic virus type 1 peptides in chimeric and multivalent constructs with promiscuous T-cell epitopes enhance immunogenicity and overcome genetic restriction. Journal of Virology, 1995. 69(10): pp. 6077-6089.
Le, X.F. et al., Roles of human epidermal growth factor receptor 2, c-jun NH2-terminal kinase, phosphoinositide 3-kinase, P70 S6 kinase pathways in regulation of cyclin G2 expression in human breast cancer cells. Molecular Cancer Therapeutics, 2007. 6: 2843-2857.
LeCouter et al., Identification of an angiogenic mitogen selective for endocrine gland endothelium. Nature, 2001. 412: p. 877-884.
Leung et al., Vascular endothelial growth factor is a secreted angiogenic mitogen. Science, 1989. 246: p. 1306-1309.
Lewis, G.D. et al., Differential responses of human tumor eel/lines to anti-p. 185HER2 monoclonal antibodies. Cancer Immunol Immunother, 1993. 37(4): p. 255-63.
Li, M. et al., Reconstitution of human Fe gamma Rill cell type specificity in transgenic mice. J Exp Med, 1996. 183(3): p. 1259-63.
Lindencrona, J.A. et al., CD4+ T cell-mediated HER-2/neu-specific tumor rejection in the absence of B cells. Int J Cancer, 2004. 1 09(2): p. 259-64.
Lu et al., Identification of the residues in the extracellular region of KDR important for the interaction with vascular endothelial growth factor and neutralizing anti-KDR antibodies. Journal of Biological Chemistry, 2000. 275(19): p. 14321-14330.
Margolin et al., Phase 1b trial of intravenous recombinant humanized monoclonal antibody to vascular endothelial growth factor in combination with chemotherapy in patients with advanced cancer: Pharmacologic and long-term safety data. J Clin Oncol, 2001. 19: p. 851-856.
Markman et al., Phase III randomized trial of 12 versus 3 months of maintenance paclitaxel in patients with advanced ovarian cancer after complete response to platinum and paclitaxel-based chemotherapy: a Southwest Oncology Group and Gynecologic Oncology Group trial. J Clin Oncol, 2003. 21: p. 2460-5.
Marmor, M.D. et al., Signal transduction and oncogenesis by ErbB/HER receptors. Int J Radiat Oncol Bioi Phys, 2004. 58(3): p. 903-13.
McGuire et al., Cyclophosphamide and cisplatin compared with paclitaxel and cisplatin in patients with stage III and stage IV ovarian cancer. N Engl J Med, 1996. 334: p. 1-6.
Montgomery, R.B. et al., Endogenous anti-HER2 antibodies block HER2 phosphorylation and signaling through extracellular signal-regulated kinase. Cancer Res, 2005. 65(2): p. 650-6.
Moriyama, M. et al., Expression of c-erbB-2 gene product in urinary bladder cancer. J Urol, 1991. 145(2): p. 423-7.
Morris, M.C. et al., A peptide carrier for the delivery of biologically active proteins into mammalian cells. Nat Biotechnol, 2001. 19(12): p. 1173-6.
Muller, Y.A. et al., Vascular endothelial growth factor: crystal structure and functional mapping of the kinase domain receptor binding site. Proc Natl Acad Sci US A, 1997. 94(14): p. 7192-7.
Muller, Y.A. et al., VEGF and the Fab fragment of a humanized neutralizing antibody: crystal structure of the complex at 2.4 A resolution and mutational analysis of the interface. Structure, 1998. 6(9): p. 1153-67.
Nahta, R. et al., In vitro effects oftrastuzumab and vinorelbine in trastuzumab-resistant breast cancer cells. Cancer Chemother Pharmacol, 2004. 53(2): p. 186-90.
Nahta, R. et al., The HER-2-targeting antibodies trastuzumab and pertuzumab synergistically inhibit the survival of breast cancer cells. Cancer Res, 2004. 64(7): p. 2343-6.
Nair, S. S et al., Synergy between tumor immunotherapy and antiangiogenic therapy. Blood, 2003. 102(3): p. 964-71.
Nanni, P. et al., Combined allogeneic tumor cell vaccination and systemic interleukin 12 prevents mammary carcinogenesis in HER-2/neu transgenic mice. J Exp Med, 2001.194(9): p. 1195-205.
Noguchi, Y. et al., Influence of interleukin 12 on p53 peptide vaccination against established Meth A sarcoma. Proceedings of the National Academy of Sciences of the United States of America, 1995. 92(6): p. 2219-23.
Ogiso, H. et al., Crystal structure of the complex of human epidermal growth factor and receptor extracellular domains. Cell, 2002. 11 0(6): p. 775-87.
Okugawa et al., A novel human HER-2-derived peptide homologous to the mouse $K^d$-restricted tumor rejection antigen can induce HLA-A24-restricted cytotoxic T lymphocytes in ovarian cancer patients and healthy individuals. Eur. J. Immunol, 2000. 30: p. 3338-3346.
Olson et al., Vascular permeability factor gene expression in normal and neoplastic human ovaries. Cancer Res, 1994. 54: p. 276-80.
Oshima, R.G. et al., Angiogenic acceleration of Neu induced mammary tumor progression and metastasis. Cancer Res, 2004. 64(1): p. 169-79.

(56) References Cited

OTHER PUBLICATIONS

Pal, D et al., Beta-Sheet propensity and its correlation with parameters based on ' conformation. Acta Crystallographica Section D, 2000. D56: pp. 589-594.

Paley et al., Vascular endothelial growth factor expression in early stage ovarian Cancer. Cancer, 1997. 80: p. 98-106.

Park, J.B. et al., Amplification, overexpression, and rearrangement of the erbB-2 protooncogene in primary human stomach carcinomas. Cancer Res, 1989. 49(23): p. 6605-9.

Partidos, C.D. et al., Specificity of the T-cell responses in covalently linked peptides each comprising of a T helper epitope. Molecular Immunology, 1997. 34(16-17): pp. 1105-1111.

Passaniti et al., A simple, quantitative method for assessing angiogenesis and antiangiogenic agents using reconstituted basement membrane, heparin, and fibroblast growth factor. Lab Invest, 1992. 67: p. 519-528.

Pegram, M.D. et al., Combined biological therapy of breast cancer using monoclonal antibodies directed against HER2/neu protein and vascular endothelial growth factor. Semin Oncol, 2002. 29(3 Suppl 11): p. 29-37.

Pegram, M.D., et al., Phase II study of receptor-enhanced chemosensitivity using humanized anti-p185HER2/neu monoclonal antibody plus cisplatin in patients with HER2/neu-overexpressing metastatic breast cancer refractory to chemotherapy treatment. J. Clin. Oncol., 1998. 16:2659-71.

Peoples et al., Breast and ovarian cancer-specific cytotoxic T lymphocytes recognize the same HER2/neu-derived peptide. Proc. Natl. Acad. Sci. USA, 1995. 92: p. 432-436.

Perez, S.A. et al., HER-2/neu-derived peptide 884-899 is expressed by human breast, colorectal and pancreatic adenocarinomas and is recognized by in-vitro-induced specific CD4(+) T cell clones. Cancer Immunol Immunother, 2002. 50(11): p. 615-24.

Piechocki, M.P. et al., Complementary antitumor immunity induced by plasmid DNA encoding secreted and cytoplasmic human ErbB-2. J Immunol, 2001. 167(6): p. 3367-74.

Piechocki, M.P. et al., Wei, Human ErbB-2 (Her-2) transgenic mice: a model system for testing Her-2 based vaccines. J Immunol, 2003. 171 (11): p. 5787-94.

Press, M.F. et al., Amplification and overexpression of HER-2/neu in carcinomas of the salivary gland: correlation with poor prognosis. Cancer Res, 1994. 54(21): p. 5675-82.

Pupa, S.M. et al., Prevention of spontaneous neu-expressing mammary tumor development in mice transgenic for rat proto-neu by DNA vaccination. Gene Ther, 2001. 8(1): p. 75-9.

Pupa, S.M. et al., Inhibition of Mammary Carcinoma Development in HER-2/neu Transgenic Mice through Induction of Autoimmunity by Xenogeneic DNA Vaccination. Cancer Res, 2005. 65(3): p. 1071-8.

Quaglino, E. et al., Electroporated DNA vaccine clears away multifocal mammary carcinomas in her-2/neu transgenic mice. Cancer Res, 2004. 64(8): p. 2858-64.

Reilly, R.T. et al., the collaboration of both humoral and cellular HER-2/neu-targeted immune responses is required for the complete eradication of HER-2/neu-expressing tumors. Cancer Res, 2001. 61 (3): p. 880-3.

Reilly, R.T. et al., HER-2/neu is a tumor rejection target in tolerized HER-2/neu transgenic mice. Cancer Research, 2000. 60(13): p. 3569-76.

Riemer, A.B. et al., Generation of Peptide mimics of the epitope recognized by trastuzumab on the oncogenic protein Her-2/neu. J Immunol, 2004. 173(1): p. 394-401.

Rose et al., Hydrophobicity of Amino Acid Residues in Globular Proteins. Science, 1985. 229: p. 834-838.

Rovero, S. et al., DNA vaccination against rat her-2/Neu p185 more effectively inhibits carcinogenesis than transplantable carcinomas in transgenic BALB/c mice. J Immunol, 2000. 165(9): p. 5133-42.

Rugo, H.S., Bevacizumab in the treatment of breast cancer: rationale and current data. Oncologist, 2004. 9 Suppl 1: p. 43-9.

Saito, H. et al., Relationship between the expression of vascular endothelial growth factor and the density of dendritic cells in gastric adenocarcinoma tissue. Br J Cancer, 1998. 78(12): p. 1573-7.

Sakaguchi, Regulatory T cells: key controllers of immunologic self-tolerance. Cell, 2000. 101: p. 455-8.

Sakai, Y. et al., Vaccination by genetically modified dendritic cells expressing a truncated neu oncogene prevents development of breast cancer in transgenic mice. Cancer Res, 2004. 64(21): p. 8022-8.

Salazar, L.G. et al., Immunization of cancer patients with HER-2/neu-derived peptides demonstrating high-affinity binding to multiple class II alleles. Clinical Cancer Research, 2003. 9: p. 5559-5565.

Samuelsson, A et al., Anti-inflammatory activity of IVIG mediated through the inhibitory Fe receptor. Science, 2001. 291 (5503): p. 484-6.

Saucier, C. et al., The She adaptor protein is critical for VEGF induction by Met/HGF and ErbB2 receptors and for early onset of tumor angiogenesis. Proc Natl Acad Sci US A, 2004. 101(8): p. 2345-50.

Schaller, G. et al., Therapy of metastatic breast cancer with humanized antibodies against the HER2 receptor protein. J Cancer Res Clin Oncol, 1999. 125(8-9): p. 520-4.

Schirle, M. et al., Combining computer algorithms with experimental approaches permits the rapid and accurate identification of T cell epitopes from defined antigens. Journal of Immunological Methods, 2001. 257: p. 1-16.

Scholl, S. et al., Targeting HER2 in otherturnortypes. Ann Oncol, 2001. 12 Suppl1: p. S81-7.

Skolnick, J. et al. From genes to protein structure and function: novel applications of computational approaches in the genomic era. TIBTECH, 2000. 18: p. 34-39.

Slamon, D.J. et al., Studies of the HER-2/neu proto-oncogene in human breast and ovarian cancer. Science, 1990. 244(4905): p. 707-12.

Sliwkowski, M.X. et al., Nonclinical studies addressing the mechanism of action of trastuzumab (Herceptin). Seminars In Oncology, 1999. 26(4 Suppl 12): p. 60-70.

Sotiriadou, R. et al., Peptide HER2(776-788) represents a naturally processed broad MHC class II-restricted T cell epitope. Br J Cancer, 2001. 85(10): p. 1527-34.

Spadaro, M. et al., Immunological inhibition of carcinogenesis. Cancer Immunol Immunother, 2004. 53(3): p. 204-16.

Spiridon, C. I. et al., Targeting multiple Her-2 epitopes with monoclonal antibodies results in improved antigrowth activity of a human breast cancer eel/line in vitro and in vivo. Clin Cancer Res, 2002. 8(6): p. 1720-30.

Spiridon, C. I. et al., A comparison of the in vitro and in vivo activities of lgG and Fab2 fragments of a mixture of three monoclonal anti-Her-2 antibodies. Chin Cancer Res, 2004. 10(10): p. 3542-51.

Srinivasan, M. et al., Suppression of experimental autoimmune encephalomyelitis using peptide mimics of C02 B. J Immunol, 2002. 169(4): p. 2180-8.

Srinivasan, M. et al., A retro-inverso peptide mimic of CD28 encompassing the MYPPPY motif adopts a polyproline type II helix and inhibits encephalitogenic T cells in vitro. J Immunol, 2001. 167(1): p. 578-85.

Street, A.G. et al., Intrinsic Beta-Sheet propensities result from van der Waals interactions between side chains and the local backbone. Proc Natl Acad Sci, 1999. 96: 9074-9076.

Sun, J. et al., Blocking angiogenesis and tumorigenesis with GFA-116, a synthetic molecule that inhibits binding of vascular endothelial growth factor to its receptor. Cancer Res, 2004. 64(1 0): p. 3586-92.

Sun, X. et al., Angiostatin enhances 87. 1-mediated cancer immunotherapy independently of effects on vascular endothelial growth factor expression. CancerGeneTher, 2001. 8(10): p. 719-27.

Tagliabue et al., Selection of monoclonal antibodies which induce internalization and phosphorylation of p185HER2 and growth inhibition of cells with HERs/neu gene amplification. International Journal of Cancer, 1991. 47: p. 933-937.

(56) References Cited

OTHER PUBLICATIONS

Tempter et al., Vascular endothelial growth factor serum concentrations in ovarian cancer. Obstet Gynecol, 1998. 92: p. 360-3.
Thornton et al., Location of "continuous" antigenic determinants in the protruding regions of proteins. The EMBO Journal, 1986. 5(2): p. 409-413.
Tischer, E. et al., The human gene for vascular endothelial growth factor. Multiple protein forms are encoded through alternative exon splicing. J Bioi Chern, 1991. 266(18): p. 11947-54.
Tokuda, Y. et al., In vitro and in vivo anti-tumour effects of a humanised monoclonal antibody against cerbB-2 product. BrJ Cancer, 1996. 73(11): p. 1362-5.
Triozai et al., Subunit peptide cancer vaccines targeting activating mutations of the p21 RAS proto-oncogene. Biomedical Peptides, Proteins, and Nucleic Acids, 1995. 1: p. 185-192.
Tuttle, T.M. et al., Proliferative and cytokine responses to class II HER- 2/neuassociated peptides in breast cancer patients. Clin Cancer Res, 1998. 4(8): p. 2015-24.
Vaisman, N. et al., Specific inhibition of the reaction between a tumor-inhibitory antibody and the ErbB-2 receptor by a mimotope derived from a phage display library. Immunol Lett, 2000. 75(1): p. 61-7.
Vicari D. Evaluation of VEGF peptide mimics as inhibitors of angiogenesis, Dissertation, The Ohio State University, 2008.
Vicari, et al. VEGF peptidomimetics: an alternate approach for angiogenesis targeted therapy, ACS Conference, Jun. 13, 2008.
Vinter-Jensen, L., Pharmacological effects of epidermal growth factor (EGF) with focus on the urinary and gastrointestinal tracts. APMIS Suppl, 1999. 93: p. 1-42.
Wagner et al., Immunological Consolidation of Ovarian Carcinoma Recurrences with Monoclonal Anti-ldiotype Antibody ACA125: Immune Responses and Sruvival in Palliative Treatment. Clinical Cancer Research, 2001. 7: p. 1154-1162.
Wei et al., Immunogene therapy of tumors with vaccine based on Xenopus homologous vascular endothelial growth factor as a model antigen. Proc Natl Acad Sci, 2001. 98: p. 11545-11550.
Welling et al., Prediction of sequential antigenic regions in proteins. FEBS Lett., 1985. 188: p. 215-218.
Wolff et al., Direct gene transfer into mouse muscle in vivo. Science, 1990. 247: p. 1465-1468.
Woodbine et al., Peptide vaccine strategy for immunotherapy of human breast cancer using HER-2/neu oncogene. The American Peptide Symposium, 1995. Abstract MS009.
Woodbine et al., Biological effects of peptide antibodies raised to HER-2/neu. Implications for therapy of human breast cancer. The American Peptide Symposium, 1997. Abstract P442.
Woodbine et al., Biological effects of anti-peptide receptor tyrosine kinase: Implications for therapy antibodies against HER-2/neu of human breast cancer. Dissertation at Ohio State University, 1998.
Xu, F. et al., Antibody-induced growth inhibition is mediated through immunochemically and functionally distinct epitopes on the extracellular domain of the c-erbB-2 (HER-2/neu) gene product p185. Int J Cancer, 1993. 53(3): p. 401-8.
Yang et al., Design and synthesizing of human vascular endothelial growth factor (VEGF) peptide. US National Library of Medicine; Bethesda, MD, USA (English Abstract Only). 1999.
Yang, J.C. et al., A randomized trial of bevacizumab, an anti-vascular endothelial growth factor antibody, for metastatic renal cancer. N Engl J Med, 2003. 349(5): p. 427-34.
Ye, D. et al., Augmentation of a humanized anti-HER2 mAb 405 induced growth inhibition by a human-mouse chimeric anti-EGF receptor mAb C225. Oncogene, 1999. 18(3): p. 731-8.
Yen, L. et al., Heregulin selectively upregulates vascular endothelial growth factor secretion in cancer cells and stimulates angiogenesis. Oncogene, 2000. 19(31): p. 3460-9.
Yip, Y.L. et al., Anti-ErbB-2 monoclonal antibodies and ErbB-2-directed vaccines. Cancer Immunol Immunother, 2002. 50(11): p. 569-87.
Yip, Y.L. et al., Identification of epitope regions recognized by tumor inhibitory and stimulatory anti-ErbB-2 monoclonal antibodies: implications for vaccine design. J Immunol, 2001. 166(8): p. 5271-8.
Zilberberg, L. et al., Structure and inhibitory effects on angiogenesis and tumor development of a new vascular endothelial growth inhibitor. J Bioi Chern, 2003. 278(37): p. 35564-73.
Preliminary Amendment filed on Mar. 4, 2008 for Australian application No. 2006261342, which claims priority to PCT/US2006/023672 filed on Jun. 15, 2006 (Applicant—The Ohio State University Research Foundation// Inventor—Kaumaya et al.) (27 pages).
Direction to request examination issued Oct. 16, 2009 for Australian application No. 2006261342, which claims priority to PCT/US2006/023672 filed on Jun. 15, 2006 (Applicant—The Ohio State University Research Foundation// Inventor—Kaumaya et al.) (1 page).
Request for examination filed Jan. 18, 2010 for Australian application No. 2006261342, which claims priority to PCT/US2006/023672 filed on Jun. 15, 2006 (Applicant—The Ohio State University Research Foundation// Inventor—Kaumaya et al.) (2 pages).
Office action issued Jan. 5, 2011 for Australian application No. 2006261342, which claims priority to PCT/US2006/023672 filed on Jun. 15, 2006 (Applicant—The Ohio State University Research Foundation//Inventor—Kaumaya et al.) (3 pages).
Request to enter Canadian national phase filed Dec. 17, 2007 for PCT/US2006/023672 filed Jun. 15, 2006 (Applicant—The Ohio State University Research Foundation// Inventor—Kaumaya et al.) (3 pages).
Communication regarding possible amendment to claims issued Mar. 1, 2010 for European application No. 06785065.1, which claims priority to PCT/US2006/023672 filed on Jun. 15, 2006 (Applicant—The Ohio State University Research Foundationfi Inventor—Kaumaya et al.) (2 pages).
Preliminary Amedment filed Apr. 12, 2010 for European application No. 06785065.1, which claims priority to PCT/US2006/023672 filed on Jun. 15, 2006 (Applicant—the Ohio State University Research Foundation// Inventor—Kaumaya et al.) (8 pages).
Supplementary European Search Report issued Aug. 19, 2010 for European application No. 06785065.1 , which claims priority to PCT/US2006/023672 filed on Jun. 15, 2006 (Applicant—The Ohio State University Research Foundation// Inventor—Kaumaya et al.) (8 pages).
Invitation to declare maintenance of the application and to correct deficiencies in the Written Opinion/amend application issued Sep. 7, 2010 for European application No. 06785065.1 , which claims priority to PCT/US2006/023672 filed on Jun. 15, 2006 (Applicant—The Ohio State University Research Foundation// Inventor—Kaumaya et al.) (1 page).
Withdrawl of application issued May 6, 2011 for European application No. 06785065.1 which claims priority to PCT/US2006/023672 filed on Jun. 15, 2006 (Applicant—The Ohio State University Research Foundation// Inventor—Kaumaya et al.) (2 pages).
Request for further processing filed Jul. 18, 2011 for European application No. 06785065.1, which claims priority to PCT/US2006/023672 filed on Jun. 15, 2006 (Applicant—The Ohio State University Research Foundation// Inventor—Kaumaya et al.) (8 pages).
Decision to allow further processing issued Sep. 7, 2011 for European application No. 06785065.1, which claims priority to PCT/US2006/023672 filed on Jun. 15, 2006 (Applicant—The Ohio State University Research Foundation// Inventor—Kaumaya et al.) (1 page).
Office Action issued on Dec. 22, 2011 for European application No. 06785065.1 filed on, which claims priority to PCT/US2006/023672 filed on Jun. 15, 2006(Applicant—The Ohio State University Research Foundation// Inventor—Kaumaya et al.) (3 pages).
Response to Office Action filed on Jul. 2, 2012 for European application No. 06785065.1, which claims priority to PCT/US2006/023672 filed on Jun. 15, 2006 (Applicant—The Ohio State University Research Foundation// Inventor—Kaumaya et al.) (18 pages).
Amendment of claims filed on Jun. 1, 2009 for Japanese application No. 2008-517193 , which claims priority to PCT/US2006/023672

(56) References Cited

OTHER PUBLICATIONS filed on Jun. 15, 2006 (Applicant—The Ohio State University Research Foundation// Inventor—Kaumaya et al.) (7 pages).
Office Action issued Sep. 17, 2011 for Japanese application No. 2008-517193, which claims priority to PCT/US2006/023672 filed on Jun. 15, 2006 (Applicant—The Ohio State University Research Foundation// Inventor—Kaumaya et al.) (12 pages).
Response to office action filed Apr. 17, 2012 for Japanese application No. 2008-517193, which claims priority to PCT/US2006/023672 filed on Jun. 15, 2006 (Applicant—The Ohio State University Research Foundation// Inventor—Kaumaya et al.) (6 pages).
Amendment to specification filed Mar. 4, 2008 for New Zeland application No. 564951, which claims priority to PCT/US2006/023672 filed on Jun. 15, 2006 (Applicant—The Ohio State University Research Foundation// Inventor—Kaumaya et al.) (27 pages).
International preliminary report on patentability issued Dec. 17, 2009 for PCT/US2006/23672 filed Jun. 15, 2006 (Applicant—The Ohio State University Research Foundationfi Inventor—Kaumaya et al.) (5 pages).
Written opinion of international search report issued Jan. 17, 2008 for PCT/US2006/23672 filed Jun. 15, 2006 (Applicant—The Ohio State University Research Foundation// Inventor—Kaumaya et al.) (4 pages).
Preliminary amendment filed Jun. 15, 2006 for U.S. Appl. No. 11/424,526, filed Jun. 15, 2006 (Inventor—Kaumaya et al.) (15 pages).
Restriction requirement issued Nov. 1, 2007 for U.S. Appl. No. 11/424,526, filed Jun. 15, 2006 (Inventor—Kaumaya et al.) (15 pages).
Response to restriction requirement filed Feb. 1, 2008 for U.S. Appl. No. 11/424,526, filed Jun. 15, 2006 (Inventor—Kaumaya et al.) (15 pages).
Non-final Office Action issued Apr. 15, 2008 for U.S. Appl. No. 11/424,526, filed on Jun. 15, 2006 (Inventor—Kaumaya et al.) (19 pages).
Response to Office Action filed Oct. 15, 2008 for U.S. Appl. No. 11/424,526, filed on Jun. 15, 2006 (Inventor—Kaumaya et al.) (14 pages).
Non-final Office Action issued Jan. 7, 2009 for U.S. Appl. No. 11/424,526, filed Jun. 15, 2006 (Inventor—Kaumaya et al.) (9 pages).
Response to Office Action filed Jul. 7, 2009 for U.S. Appl. No. 11/424,526, filed Jun. 15, 2006 (Inventor—Kaumaya et al.) (8 pages).
Notice of allowance issed Oct. 30, 2009 for U.S. Appl. No. 11/424,526, filed Jun. 15, 2006 (Inventor—Kaumaya et al.) (7 pages).
Notice of Abandonment issued Oct. 18, 2010 for U.S. Appl. No. 12/697,578, filed Feb. 1, 2010 (Inventor—Kaumaya et al.) (2 pages).
Petition to Revive filed Dec. 6, 2010 for U.S. Appl. No. 12/697,578, filed Feb. 1, 2010 (Inventor—Kaumaya et al.) (3 pages).
Restriction Requirement issued Mar. 18, 2011 for U.S. Appl. No. 12/697,578, filed Feb. 1, 2010 (Inventor—Kaumaya et al.) (9 pages).
Response to Restriction Requirement filed Jun. 15, 2011 for U.S. Appl. No. 12/697,578, filed Feb. 1, 2010 (Inventor—Kaumaya et al.) (3 pages).
Office Action issued Sep. 1, 2011 for U.S. Appl. No. 12/697,578, filed Feb. 1, 2010 (Inventor—Kaumaya et al.) (11 pages).
Response to Office Action filed Mar. 1, 2012 for U.S. Appl. No. 12/697,578, filed Feb. 1, 2010 (Inventor—Kaumaya et al.) (9 pages).
Office Action issued Apr. 27, 2012 for U.S. Appl. No. 12/697,578, filed Feb. 1, 2010 (Inventor—Kaumaya et al.) (6 pages).
Response to Office Action and Terminal Disclaimer filed Jul. 27, 2012 for U.S. Appl. No. 12/697,578, filed Feb. 1, 2010 (Inventor—Kaumaya et al.) (7 pages).

Terminal Disclaimer Review Decision issued Jul. 31, 2012 for U.S. Appl. No. 12/697,578, filed Feb. 1, 2010 (Inventor—Kaumaya et al.) (1 page).
Notice of Allowance issued Aug. 7, 2012 for U.S. Appl. No. 12/697,578, filed Feb. 1, 2010 (Inventor—Kaumaya et al.) (7 pages).
Preliminary Amendment filed Apr. 15, 2002 for U.S. Appl. No. 09/632,036, filed Aug. 3, 2000 (Inventor—Kaumaya et al.) (34 pages).
Restriction requirement issued Oct. 2, 2002 for U.S. Appl. No. 09/632,036, filed Aug. 3, 2000 (Inventor—Kaumaya et al.) (6 pages).
Response to restriction requirement filed Dec. 9, 2002 for U.S. Appl. No. 09/632,036, filed Aug. 3, 2000 (Inventor—Kaumaya et al.) (1 page).
Second Preliminary Amendment filed Dec. 2, 2002 for U.S. Appl. No. 09/632,036, filed Aug. 3, 2000 (Inventor—Kaumaya et al.) (8 pages).
Miscellaneous Action issued Feb. 26, 2003 for U.S. Appl. No. 09/632,036, filed Aug. 3, 2000 (Inventor—Kaumaya et al.) (2 pages).
Response to Miscellaneous Action issued Mar. 31, 2003 for U.S. Appl. No. 09/632,036, filed Aug. 3, 2000 (Inventor—Kaumaya et al.) (2 pages).
Amendment filed May 27, 2003 for U.S. Appl. No. 09/632,036, filed Aug. 3, 2000 (Inventor—Kaumaya et al.) (21 pages).
Restriction requirement issued Aug. 6, 2003 for U.S. Appl. No. 09/632,036 filed on Aug. 3, 2000 (Inventor—Kaumaya et al.) (13 pages).
Response to restriction requirement filed Dec. 10, 2003 for U.S. Appl. No. 09/632,036, filed Aug. 3, 2000 (Inventor—Kaumaya et al.) (2 pages).
Communication Regarding Non-Responsive Election issued May 5, 2004 for U.S. Appl. No. 09/632,036, filed Aug. 3, 2000 (Inventor—Kaumaya et al.) (6 pages).
Response to restriction requirement filed Jun. 9, 2004 for U.S. Appl. No. 09/632,036, filed Aug. 3, 2000 (Inventor—Kaumaya et al.) (2 pages).
Office Action issued Oct. 15, 2004 for U.S. Appl. No. 09/632,036, filed Aug. 3, 2000 (Inventor—Kaumaya et al.) (46 pages).
Response to Office Action filed Mar. 17, 2005 for U.S. Appl. No. 09/632,036, filed Aug. 3, 2000 (Inventor—Kaumaya et al.) (30 pages).
Notice of Non-complient amendment issued Jun. 17, 2005 for U.S. Appl. No. 09/632,036, filed Aug. 3, 2000 (Inventor—Kaumaya et al.) (3 pages).
Response to Notice of Non-complient amendment issued Jun. 24, 2005 for U.S. Appl. No. 09/632,036, filed Aug. 3, 2000 (Inventor—Kaumaya et al.) (21 pages).
Office Action issued Sep. 21, 2005 for U.S. Appl. No. 09/632,036, filed Aug. 3, 2000 (Inventor—Kaumaya et al.) (23 pages).
Response to Office Action filed Nov. 14, 2005 for U.S. Appl. No. 09/632,036, filed Aug. 3, 2000 (Inventor—Kaumaya et al.) (7 pages).
Notice of Allowance issued Jan. 25, 2006 for U.S. Appl. No. 09/632,036, filed Aug. 3, 2000 (Inventor—Kaumaya et al.) (9 pages).
Restriction Requirement issued Apr. 10, 2008 for U.S. Appl. No. 11/423,194, filed Jun. 9, 2006 (Inventor—Kaumaya et al.) (45 pages).
Response to Restriction Requirement filed Apr. 17, 2009 for U.S. Appl. No. 11/423,194, filed Jun. 9, 2006 (Inventor—Kaumaya et al.) (2 pages).
Voluntary Amendment filed Aug. 10, 2009 for U.S. Appl. No. 11/423,194, filed Jun. 9, 2006 (Inventor—Kaumaya et al.) (11 pages).
Notice of Allowance issued Oct. 6, 2009 for U.S. Appl. No. 11/423,194, filed Jun. 9, 2006 (Inventor—Kaumaya et al.) (4 pages).
Restriction Requirement issued Nov. 16, 2010 for U.S. Appl. No. 12/683,114, filed Jan. 6, 2010 (Inventor—Kaumaya et al.) (16 pages).

(56) References Cited

OTHER PUBLICATIONS

Response to Restriction Requirement filed Feb. 16, 2011 for U.S. Appl. No. 12/683,114, filed Jan. 6, 2010 (Inventor—Kaumaya et al.) (2 pages).
Office Action issued Mar. 30, 2011 for U.S. Appl. No. 12/683,114, filed Jan. 6, 2010 (Inventor—Kaumaya et al.) (9 pages).
Response to Office Action filed Aug. 26, 2011 for U.S. Appl. No. 12/683,114, filed Jan. 6, 2010 (Inventor—Kaumaya et al.) (11 pages).
Notice of Allowance issued Sep. 29, 2011 for U.S. Appl. No. 12/683,114, filed Jan. 6, 2010 (Inventor—Kaumaya et al.) (8 pages).
Communication regarding possible amendment to claims issued Mar. 28, 2002 for European application No. 00953823.2, which claims priority to PCT/US2000/021222 filed on Aug. 3, 2000 (Applicant—The Ohio State University Research foundation// Inventor—Kaumaya et al.) (2 pages).
Preliminary Amendment filed May 7, 2002 for European application No. 00953823.2, which claims priority to PCT/US2000/021222 filed on Aug. 3, 2000 (Applicant—The Ohio State University Research Foundation// Inventor—Kaumaya et al.) (43 pages).
Preliminary Amendment filed May 8, 2002 for European application No. 00953823.2, which claims priority to PCT/US2000/021222 filed on Aug. 3, 2010 (Applicant—The Ohio State University Research Foundation// Inventor—Kaumaya et al.) (18 pages).
Supplementary European Search Report issued Aug. 10, 2004 for European application No. 00953823.2, which claims priority to PCT/US2000/021222 filed on Aug. 3, 200 (Applicant—The Ohio State University Research Foundation// Inventor—Kaumaya et al.) (7 pages).
Office Action issued Nov. 18, 2005 for European application No. 00953823.2, which claims priority to PCT/US2000/021222 filed on Aug. 3, 2000 (Applicant—The Ohio State University Research Foundation// Inventor—Kaumaya et al.) (16 pages).
Application deemed withdrawn Jul. 7, 2006 for European application No. 00953823.2, which claims priority to PCT/US2000/021222 filed on Aug. 3, 2000 (Applicant—The Ohio State University Research Foundation// Inventor—Kaumaya et al.) (1 page).
Request to allow further processing filed Sep. 18, 2006 for European application No. 00953823.2, which claims priority to PCT/US2000/021222 filed on Aug. 3, 2000 (Applicant—The Ohio State University Research Foundation// Inventor—Kaumaya et al.) (26 pages).
Decision to allow further processing issued Oct. 9, 2006 for European application No. 00953823.2, which claims priority to PCT/US2000/021222 filed on Aug. 3, 2000 (Applicant—The Ohio State University Research Foundation// Inventor—Kaumaya et al.) (1 page).
Office Action issued Mar. 4, 2008 for European application No. 00953823.2, which claims priority to PCT/US2000/021222 filed on Aug. 3, 2000 (Applicant—The Ohio State University Research Foundation// Inventor—Kaumaya et al.) (5 pages).
Application deemed withdrawn Oct. 17, 2008 for European application No. 00953823.2, which claims priority to PCT/US2000/021222 filed on Aug. 3, 2000 (Applicant—The Ohio State University Research Foundation// Inventor—Kaumaya et al.) (1 page).
Request to allow further processing filed Dec. 29, 2008 for European application No. 00953823.2, which claims priority to PCT/US2000/021222 filed on Aug. 3, 2000 (Applicant—The Ohio State University Research Foundation// Inventor—Kaumaya et al.) (12 pages).
Decision to allow further processing issued Jan. 28, 2009 for European application No. 00953823.2, which claims priority to PCT/US2000/021222 filed on Aug. 3, 2000 (Applicant—The Ohio State University Research Foundation// Inventor—Kaumaya et al.) (1 page).
Office Action issued Sep. 28, 2009 for European application No. 00953823.2, which claims priority to PCT/US2000/021222 filed on Aug. 3, 2000 (Applicant—The Ohio State University Research Foundation//Inventor—Kaumaya et al.) (4 pages).
Application deemed withdrawn May 17, 2010 for European application No. 00953823.2, which claims priority to PCT/US2000/021222 filed on Aug. 3, 2000 (Applicant—The Ohio State University Research Foundationfi Inventor—Kaumaya et al.) (1 page).
Request to allow further processing filed Jul. 16, 2010 for European application No. 00953823.2, which claims priority to PCT/US2000/021222 filed on Aug. 3, 2000 (Applicant—The Ohio State University Research Foundation// Inventor—Kaumaya et al.) (11 pages).
Decision to allow further processing issued Aug. 6, 2010 for European application No. 00953823.2, which claims priority to PCT/US2000/021222 filed on Aug. 3, 2000 (Applicant—The Ohio State University Research Foundation// Inventor—Kaumaya et al.) (1 page).
Office Action issued Jan. 18, 2011 for European application No. 00953823.2, which claims priority to PCT/US2000/021222 filed on Aug. 3, 2000 (Applicant—The Ohio State University Research Foundation// Inventor—Kaumaya et al.) (6 pages).
Response to Office Action issued May 26, 2011 for European application No. 00953823.2, which claims priority to PCT/US2000/021222 filed on Aug. 3, 2000 (Applicant—The Ohio State University Research Foundation// Inventor—Kaumaya et al.) (39 pages).
Telephone communication with Office Dec. 28, 2011 for European application No. 00953823.2, which claims priority to PCT/US2000/021222 filed on Aug. 2, 2000 (Applicant—The Ohio State University Research Foundation// Inventor—Kaumaya et al.) (3 pages).
Response to communication with Office Mar. 5, 2012 for European application No. 00953823.2, which claims priority to PCT/US2000/021222 filed on Aug. 3, 2000 (Applicant—The Ohio State University Research Foundation// Inventor—Kaumaya et al.) (13 pages).
Telephone communication with Office Jun. 14, 2012 for European application No. 00953823.2, which claims priority to PCT/US2000/021222 filed on Aug. 3, 2000 (Applicant—The Ohio State University Research Foundation// Inventor—Kaumaya et al.) (3 pages).
Response to communication with Office Aug. 10, 2012 for European application No. 00953823.2, which claims priority to PCT/US2000/021222 filed on Aug. 3, 2000 (Applicant—The Ohio State University Research Foundation// Inventor—Kaumaya et al.) (4 pages).
Office Action issued Aug. 29, 2012 for European application No. 00953823.2, which claims priority to PCT/US2000/021222 filed on Aug. 3, 2000 (Applicant—The Ohio State University Research Foundation//Inventor—Kaumaya et al.) (4 pages).
Telephone communication with Office Sep. 4, 2012 for European application No. 00953823.2, which claims priority to PCT/US2000/021222 filed on Aug. 3, 2000 (Applicant—The Ohio State University Research Foundation// Inventor—Kaumaya et al.) (4 pages).
Request for Examination and Voluntary Amendment filed Aug. 3, 2007 for Japanese application No. 2001-513369, which claims priority to PCT/US2000/021222 filed on Aug. 3, 2000 (Applicant—The Ohio State University Research Foundation// Inventor—Kaumaya et al.) (23 pages).
Office Action issued Jun. 23, 2010 for Japanese application No. 2001-513369, which claims priority to PCT/US2000/021222 filed on Aug. 3, 2000 (Applicant—The Ohio State University Research Foundation// Inventor—Kaumaya et al.) (7 pages).
Response to Office Action as shown by amended claims filed Sep. 22, 2010 for Japanese application No. 2001-513369, which claims priority to PCT/US2000/021222 filed on Aug. 3, 2000 (Applicant—The Ohio State University Research Foundation// Inventor—Kaumaya et al.) (9 pages).
Notice of Allowance issued Nov. 29, 2010 for Japanese application No. 2001-513369, which claims priority to PCT/US2000/021222 filed on Aug. 3, 2000 (Applicant—The Ohio State University Research Foundation// Inventor—Kaumaya et al.) (3 pages).
International Preliminary Examination Report issued Jun. 28, 2001 for PCT/US2000/021222 filed on Aug. 3, 2000 (Applicant—The Ohio State University Research Foundation// Inventor—Kaumaya et al.) (5 pages).
Preliminary amendment filed Jun. 21, 2005 for U.S. Appl. No. 11/052,721, filed Feb. 7, 2005 (Inventor—Kaumaya et al.) (11 pages).
Restriction Requirement issued Jun. 5, 2007 for U.S. Appl. No. 11/052,721, filed Feb. 7, 2005 (Inventor—Kaumaya et al.) (7 pages).

(56) References Cited

OTHER PUBLICATIONS

Response to Restriction Requirement issued Aug. 6, 2007 for U.S. Appl. No. 11/052,721, filed Feb. 7, 2005 (Inventor—Kaumaya et al.) (3 pages).
Office Action issued Oct. 2, 2007 for U.S. Appl. No. 11/052,721, filed Feb. 7, 2005 (Inventor—Kaumaya et al.) (11 pages).
Response to Office Action filed Apr. 2, 2008 for U.S. Appl. No. 11/052,721, filed Feb. 7, 2005 (Inventor—Kaumaya et al.) (15 pages).
Office Action issued Jul. 11, 2008 for U.S. Appl. No. 11/052,721, filed Feb. 7, 2005 (Inventor—Kaumaya et al.) (11 pages).
Response to Office Action filed Jan. 12, 2009 for U.S. Appl. No. 11/052,721, filed Feb. 7, 2005 (Inventor—Kaumaya et al.) (12 pages).
Office Action issued Apr. 15, 2009 for U.S. Appl. No. 11/052,721, filed Feb. 7, 2005 (Inventor—Kaumaya et al.) (8 pages).
Response to Office Action filed Jul. 15, 2009 for U.S. Appl. No. 11/052,721, filed Feb. 7, 2005 (Inventor—Kaumaya et al.) (6 pages).
Office Action issued Nov. 20, 2009 for U.S. Appl. No. 11/052,721, filed Feb. 7, 2005 (Inventor—Kaumaya et al.) (7 pages).
Response to Office Action filed May 20, 2010 for U.S. Appl. No. 11/052,721, filed Feb. 7, 2015 (Inventor—Kaumaya et al.) (10 pages).
Office Action issued Jun. 29, 2010 for U.S. Appl. No. 11/052,721, filed Feb. 7, 2005 (Inventor—Kaumaya et al.) (10 pages).
Response to Office Action filed Dec. 29, 2010 for U.S. Appl. No. 11/052,721, filed Feb. 7, 2005 (Inventor—Kaumaya et al.) (5 pages).
Ex Parte Quayle Action issued Feb. 25, 2011 for U.S. Appl. No. 11/052,721, filed Feb. 7, 2005 (Inventor—Kaumaya et al.) (4 pages).
Response to Ex Parte Quayle Action filed Apr. 19, 2011 for U.S. Appl. No. 11/052,721, filed Feb. 7, 2005 (Inventor—Kaumaya et al.) (5 pages).
Notice of Allowance issued Jun. 16, 2011 for U.S. Appl. No. 11/052,721, filed Feb. 7, 2005 (Inventor—Kaumaya et al.) (6 pages).
Notice of Allowance issued Aug. 17, 2011 for U.S. Appl. No. 11/052,721, filed Feb. 7, 2005 (Inventor—Kaumaya et al.) (5 pages).
Preliminary Amendment filed Jan. 30, 2012 for U.S. Appl. No. 13/331,891, filed Dec. 20, 2011 (Inventor—Kaumaya et al.) (57 pages).
Restriction Requirement issued Mar. 5, 2012 for U.S. Appl. No. 13/331,891, filed Dec. 20, 2011 (Inventor—Kaumaya et al.) (5 pages).
Response to Restriction Requirement filed May 29, 2012 for U.S. Appl. No. 13/331,891, filed Dec. 20, 2011 (Inventor—Kaumaya et al.) (6 pages).
Office Action issued Nov. 5, 2012 for U.S. Appl. No. 13/331,891, filed Dec. 20, 2011 (Inventor—Kaumaya et al.) (8 pages).
Office Action issed Jun. 15, 2009 for Australian application No. 2005213457, which claims priority to PCT/US2005/003747 filed on Feb. 7, 2005 (Applicant—The Ohio State University Research Foundation// Inventor—Kaumaya et al.) (2 pages).
Request for examination filed Feb. 5, 2010 for Canadian application No. 2555274, which claims priority to PCT/US2005/003747 filed on Feb. 7, 2005 (Applicant—The Ohio State University Research Foundation// Inventor—Kaumaya et al.) (2 pages).
Office Action issed Nov. 23, 2011 for Canadian application No. 2555274, which claims priority to PCT/US2005/003747 filed on Feb. 7, 2005 (Applicant—The Ohio State University Research Foundation// Inventor—Kaumaya et al.) (3 pages).
Response to Office Action filed May 23, 2012 for Canadian application No. 2555274, which claims priority to PCT/US2005/003747 filed on Feb. 7, 2005 (Applicant—The Ohio State University Research Foundation//Inventor—Kaumaya et al.) (12 pages).

Communication regarding possible amendment of claims issued Apr. 14, 2009 for European application No. 05722777.9, which claims priority to PCT/US2005/003747 filed on Feb. 7, 2005 (Applicant—The Ohio State University Research Foundation//Inventor—Kaumaya et al.) (2 pages).
Invitation to correct deficientcies issued Jun. 30, 2009 for European application No. 05722777.9, which claims priority to PCT/US2005/003747 filed on Feb. 7, 2005 (Applicant—The Ohio State University Research Foundation// Inventor—Kaumaya et al.) (3 pages).
Response to Invitation to correct deficientcies filed Aug. 24, 2009 for European application No. 05722777.9, which claims priority to PCT/US2005/003747 filed on Feb. 7, 2005 (Applicant—The Ohio State University Research Foundation// Inventor—Kaumaya et al.) (3 pages).
Supplemental European Search Report issued Feb. 3, 2010 for European application No. 05722777.9, which claims priority to PCT/US2005/003747 filed on Feb. 7, 2005 (Applicant—The Ohio State University Research Foundation// Inventor—Kaumaya et al.) (6 pages).
Communication from Examining Division issued May 27, 2010 for European application No. 05722777.9, which claims priority to PCT/US2005/003747 filed on Feb. 7, 2005 (Applicant—The Ohio State University Research Foundation// Inventor—Kaumaya et al.) (5 pages).
Application deemed withdrawn Jan. 12, 2011 for European application No. 05722777.9, which claims priority to PCT/US2005/003747 filed on Feb. 7, 2005 (Applicant—The Ohio State University Research Foundation// Inventor—Kaumaya et al.) (1 page).
Request to allow further processing filed Mar. 16, 2011 for European application No. 05722777.9, which claims priority to PCT/US2005/003747, filed on Feb. 7, 2005 (Applicant—The Ohio State University Research Foundation// Inventor—Kaumaya et al.) (9 pages).
Decision to allow further processing issued Mar. 28, 2012 for European application No. 05722777.9, which claims priority to PCT/US2005/003747 filed on Feb. 7, 2005 (Applicant—The Ohio State University Research Foundation// Inventor—Kaumaya et al.) (1 page).
Communication from Examining Division issued Oct. 28, 2011 for European application No. 05722777.9, which claims priority to PCT/US2005/003747 filed on Feb. 7, 2005 (Applicant—The Ohio State University Research Foundationli Inventor—Kaumaya et al.) (4 pages).
Response to Communication from Examining Division filed Mar. 7, 2012 for European application No. 05722777.9, which claims priority to PCT/US2005/003747 filed on Feb. 7, 2005 (Applicant—The Ohio State University Research Foundationfi Inventor—Kaumaya et al.) (27 pages).
Communication from Examining Division issued Mar. 22, 2012 for European application No. 05722777.9, which claims priority to PCT/US2005/003747 filed on Feb. 7, 2005 (Applicant—The Ohio State University Research Foundation// Inventor—Kaumaya et al.) (3 pages).
Response to Communication from Examining Division filed Jul. 31, 2012 for European application No. 05722777.9, which claims priority to PCT/US2005/003747 filed on Feb. 7, 2005 (Applicant—The Ohio State University Research Foundation// Inventor—Kaumaya et al.) (5 pages).
Communication from Examining Division issued Sep. 13, 2012 for European application No. 05722777.9, which claims priority to PCT/US2005/003747 filed on Feb. 7, 2005 (Applicant—The Ohio State University Research Foundation// Inventor—Kaumaya et al.) (4 pages).
International Search Report issued Jul. 14, 2008 for PCT/US2005/003747 filed on Feb. 7, 2005 (Applicant—The Ohio State University Research Foundation// Inventor—Kaumaya et al.) (5 pages).
Written Opinion of the International Search Authority issued Feb. 20, 2009 for PCT/US2005/003747 filed on Feb. 7, 2005 (Applicant—The Ohio State University Research Foundation// Inventor—Kaumaya et al.) (6 pages).

(56) References Cited

OTHER PUBLICATIONS

International Preliminary Report on Patentability issued Feb. 24, 2009 for PCT/US2005/003747 filed on Feb. 7, 2005 (Applicant—The Ohio State University Research Foundationfi Inventor—Kaumaya et al.) (7 pages).

Requirement for Restriction/Election issued May 24, 2012 for U.S. Appl. No. 12/700,388, filed Feb. 4, 2010 (Inventor—Kaumaya) (9 pages).

Response to Requirement for Restriction/Election filed Jun. 21, 2012 with the USPTO for U.S. Appl. No. 12/700,388, filed Feb. 4, 2010 (1st Named Inventor—Kaumaya) (9 pages).

Non-final Rejection issued Jul. 5, 2012 for U.S. Appl. No. 12/700,388, filed Feb. 4, 2010 (Inventor—Kaumaya) (10 pages).

Applicant-initiated Interview Summary filed Oct. 25, 2012 for U.S. Appl. No. 12/700,388, filed Feb. 4, 2010 (Inventor—Kaumaya) (3 pages).

\* cited by examiner

FIG. 4A
FIG. 4B
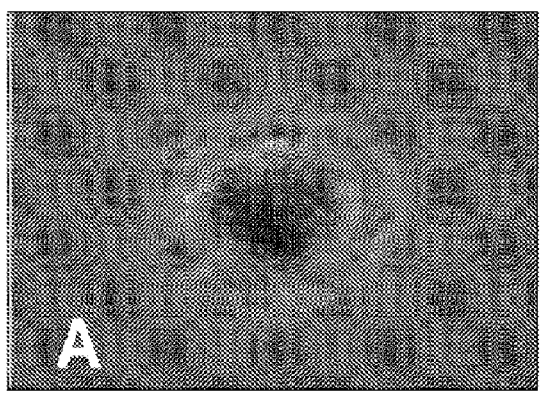
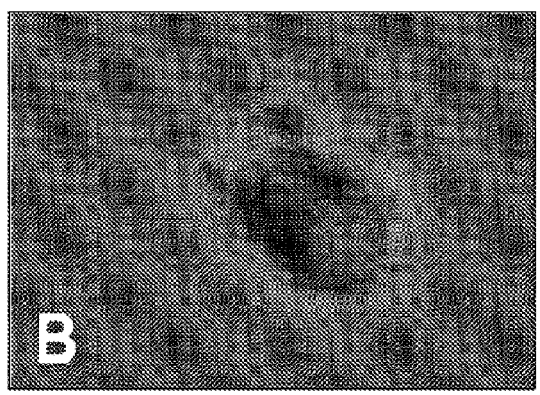
FIG. 4C
FIG. 4D
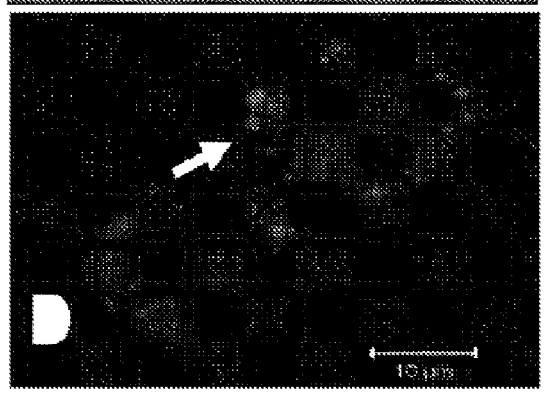
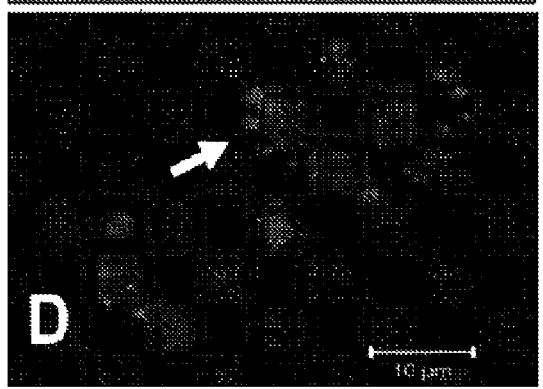
Figure 4

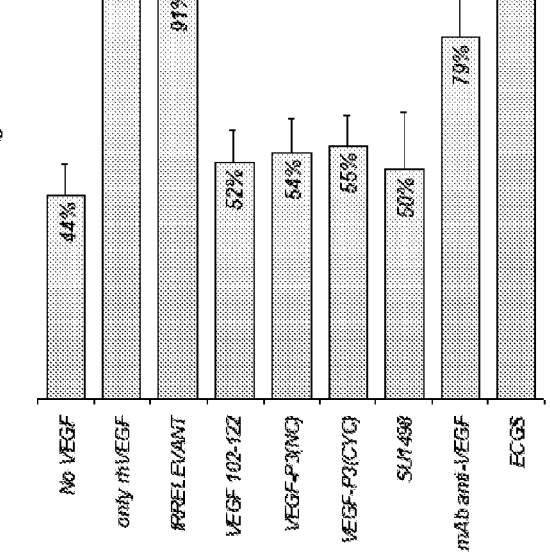
FIG. 9B
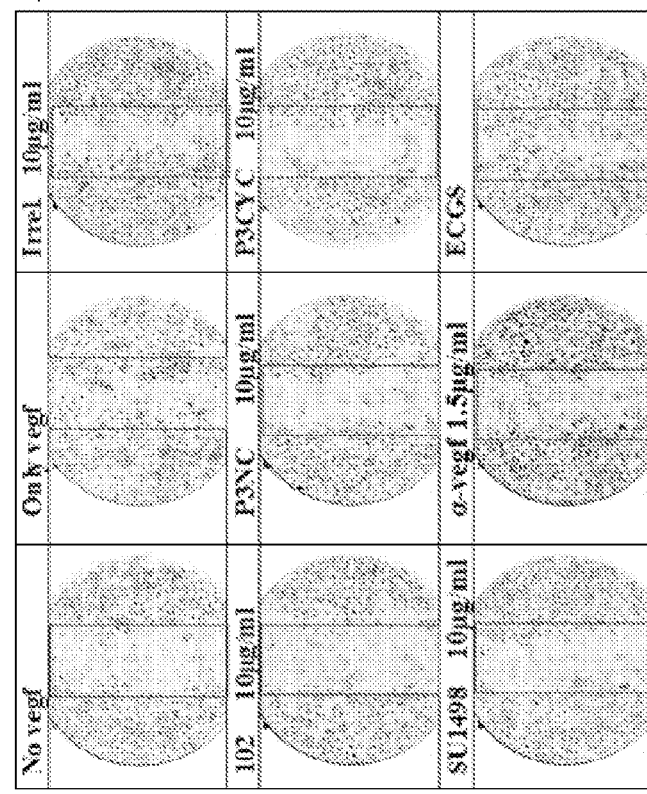
FIG. 9A
Figure 9

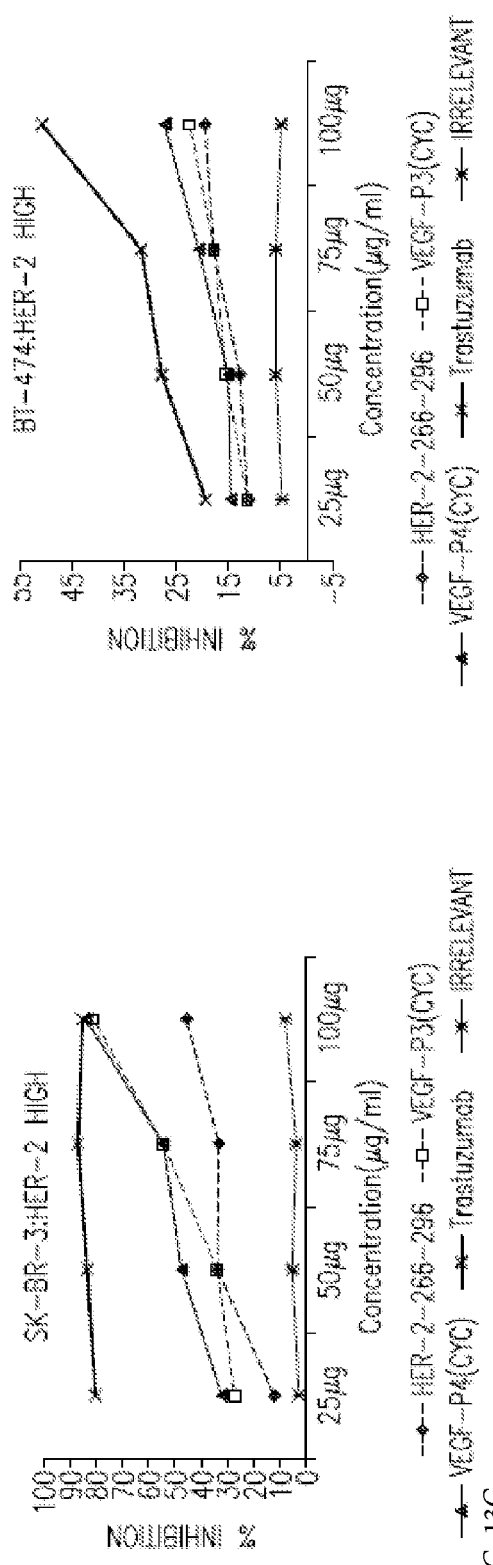
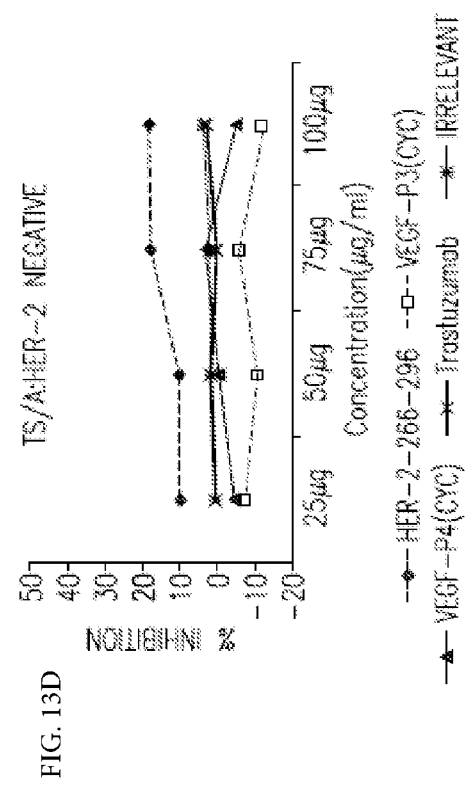
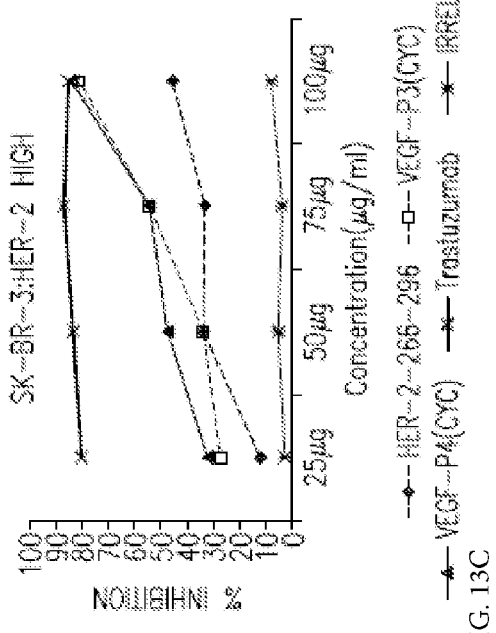
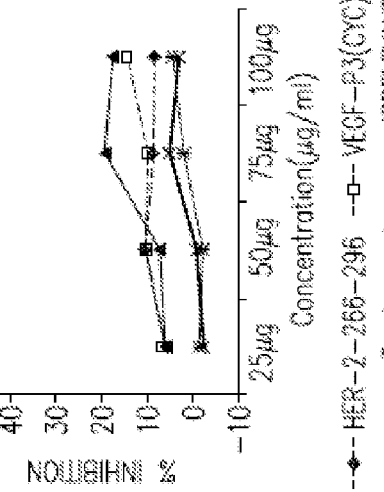
Figure 13A-D

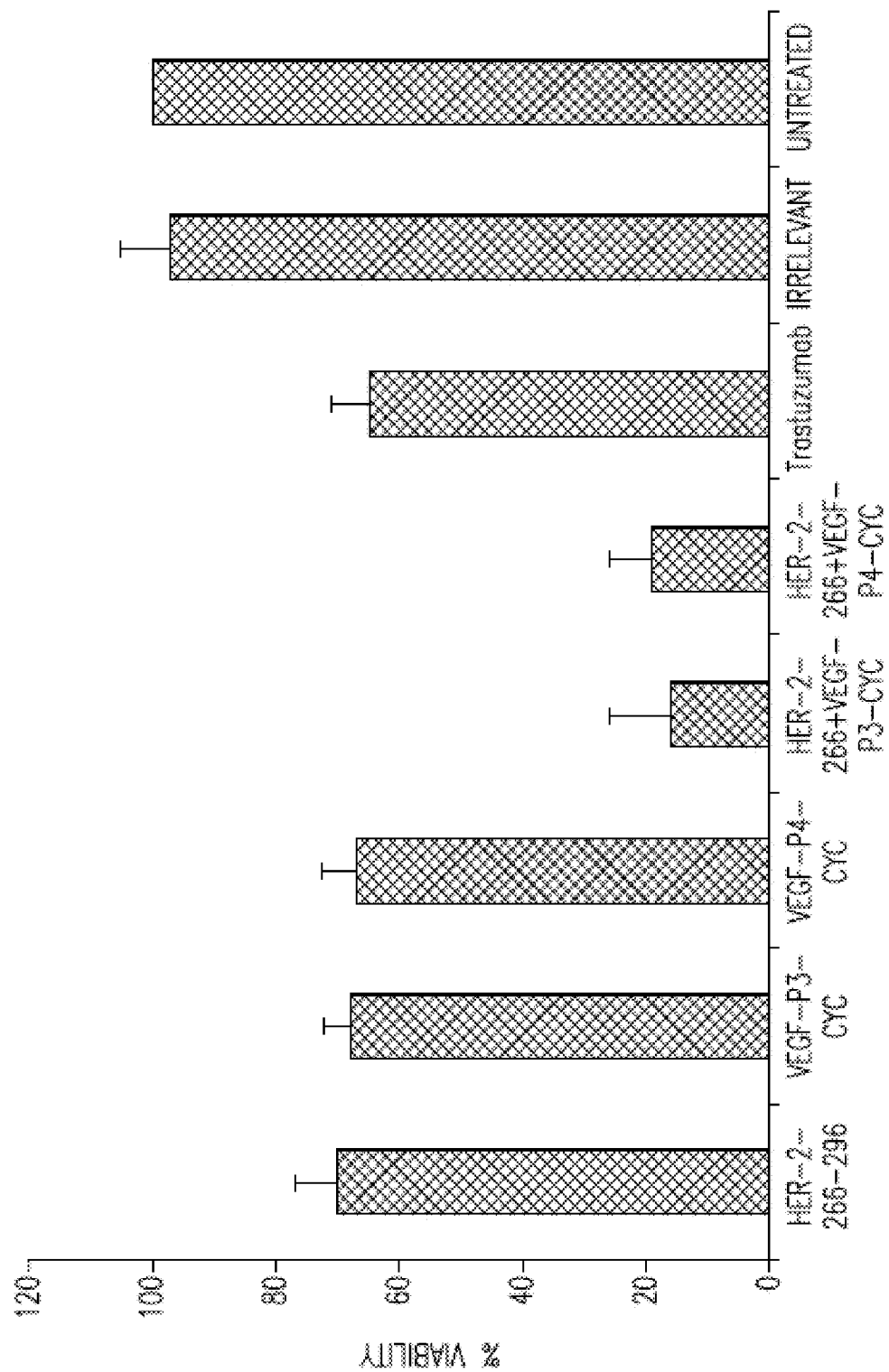

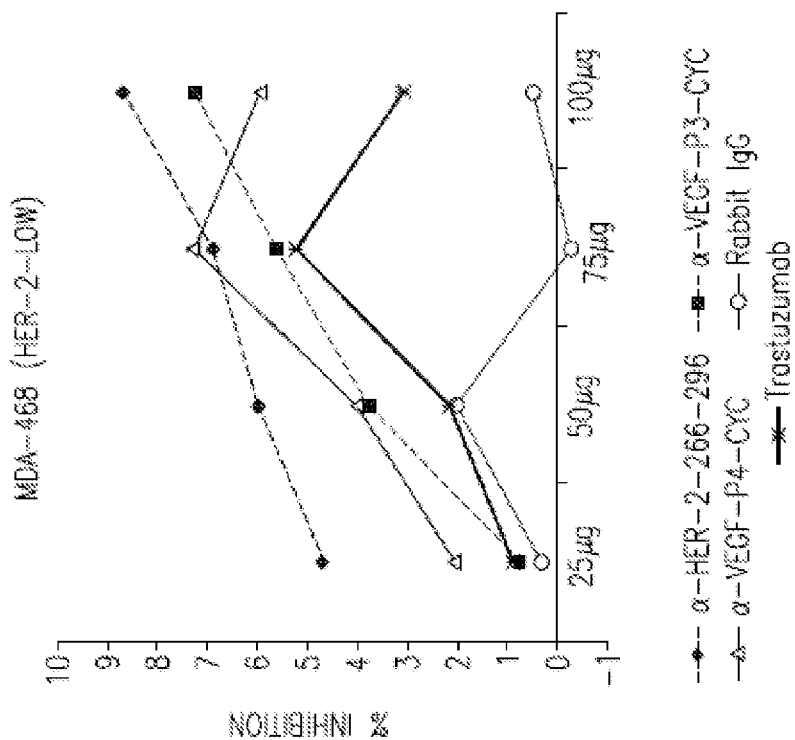
FIG. 16C
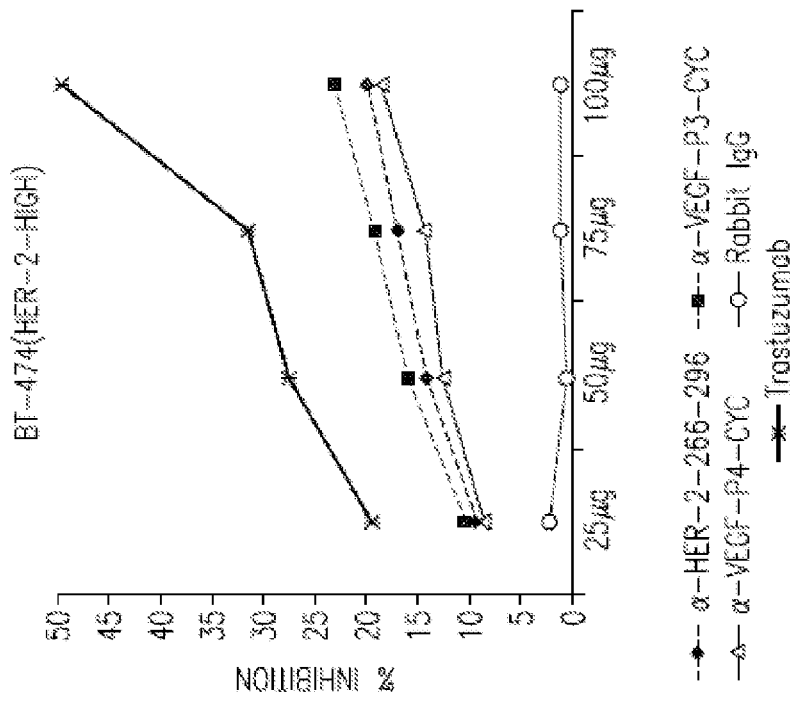
FIG. 16B
Figures 16B & 16C

FIG. 21A
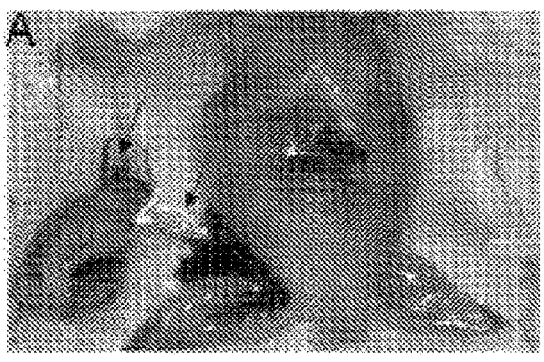
FIG. 21B
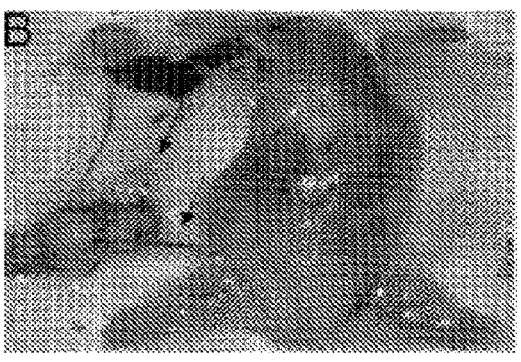
FIG. 21C
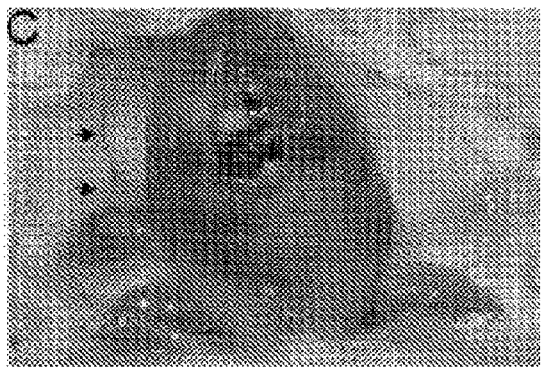
FIG. 21D
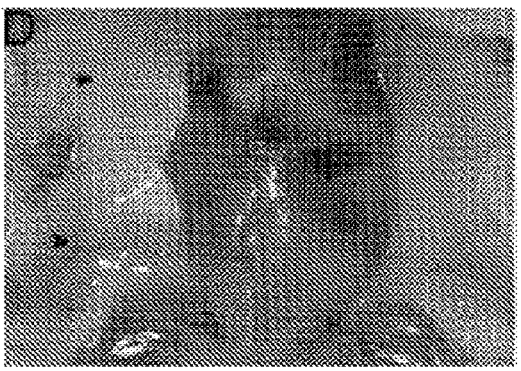
Figure 21

IMMUNOGENIC EPITOPES, PEPTIDOMIMETICS, AND ANTI-PEPTIDE ANTIBODIES, AND METHODS OF THEIR USE

CROSS-REFERENCE TO RELATED APPLICATIONS

This application is a divisional of and claims priority to U.S. patent application Ser. No. 12/700,388, filed Feb. 4, 2010, entitled "IMMUNOGENIC EPITOPES, PEPTIDOMIMETICS, AND ANTI-PEPTIDE ANTIBODIES, AND METHODS OF THEIR USE" which application claims the benefit of priority to U.S. Patent Application No. 61/149,959, filed Feb. 4, 2009, and which are fully incorporated by reference and made a part hereof.

STATEMENT REGARDING FEDERALLY SPONSORED RESEARCH

This invention was made in part with Government support awarded by the National Cancer Institute. The Government may have certain rights in the invention.

BACKGROUND

The formation of new blood vessels, called angiogenesis, is a process tightly regulated by a balance between pro- and anti-angiogenic factors and physiologically it is activated in wound healing, ovulation, and menstruation. However, it is also stimulated in pathologic conditions such as cancer, macular degeneration in the eyes, psoriasis, and diabetes. Since most tumors cannot grow beyond a few millimeters in the absence of new blood vessel formation, angiogenesis inhibitors have been explored as a drug target to be used in combination with several other cancer therapies. Several studies have explored the use of DNA vaccines, small tyrosine kinase inhibitors, siRNAs, ribozymes, antibodies, and receptor blocking agents aimed at better understanding the angiogenic mechanism and development of potential inhibitors. Specialized cancer treatments with anti-angiogenic agents approved by the FDA include the monoclonal antibody bevaciznmab (Avastin) and the small tyrosine kinase inhibitors SU11248 (sunitinib) and BAY 43-9006 (sorafenib). Although the clinical application of these drugs in cancer therapy are promising, drug resistance development and long-term side effects like hypertension and endothelium dysfunction remain a concern.

The pro-angiogenic factor VEGF is the most studied growth factor in this field due to its specificity and important role in the activation of all steps of angiogenesis in the endothelium vasculature. The splicing variant VEGF165 is the predominant form and had been shown to be up-regulated in the tumor microenvironment by hypoxia or activation of oncogenes like HER-2. VEGF is a glycoprotein and consists of an anti-parallel homodimer structure containing inter- and intra-disulfide bonds and it has been shown to bind to three receptor types: VEGFR-1 (flt-1), VEGFR-2 (flk-1 or KDR), and neurophilin-1 (NR-1). The VEGF: VEGFR-1 interaction exhibits high affinity although the role of VEGFR-1 is not fully understood. Research suggests its function in activated pathways in macrophages or endothelial progenitor cells (EPC). In the endothelial cells the majority of angiogenesis signaling (proliferation, migration and survival) proceeds via the interaction between VEGF and VEGFR-2.

The binding site of VEGF to its receptors has been characterized by crystal structure analysis as well as alanine scanning and reveals overlapping regions located at the poles in the homodimer. VEGF:VEGFR-2 interaction has been explored using antibodies that bind VEGF as well as the extra-cellular domain of VEGFR-2, identifying VEGF epitopes in the binding region that inhibit VEGF dependent pathways. The interaction between VEGF and VEGFR-2 has been identified and comprises residues at a loop region formed by the anti-parallel β-sheets β5-β6 in the VEGF protein.

Blockade of receptor-ligand interaction offers a validated and proven approach in drug development because receptor: ligand interaction is usually confined to a defined portion of the ligand and the receptor, and recent technologies have allowed the accurate identification of these binding regions. Peptidomimetics is the approach of reproducing the biological activity or binding properties in a smaller molecule, like peptides or modified peptides which were designed to mimic the desired region.

HER-2 (human epidermal growth factor receptor-2) is a member of the HER family of receptor tyrosine kinases and is overexpressed in about 30% of invasive breast cancers. HER-2 is essential for muscle spindle development and regulates the formation of neuromuscular synapses. High expression of HER-2 causes disruption of the HER network in tumor cells leading to increase survival of the tumors. HER-2 overexpression is not only limited to breast cancer and its amplification has been seen in subsets of gastric, endometrial, ovarian, lung, esophageal, and uterine cancers. The amount of HER-2 in cancer cells is much higher than in normal tissues and tumors with high levels of HER-2 expression always show intense immunohistochemical staining. This makes HER-2 a potential therapeutic target and also suggests that HER-2 targeted therapy will target most cancer cells in a given patient. The overexpression of HER-2 has also been shown in both the primary and metastatic sites which suggests that HER-2 therapy may have potential in all disease sites.

The upregulation of HER-2 is associated with increased expression of VEGF at both the RNA and protein level in human breast cancer cells and exposure of HER-2 positive cells to Trastuzumab significantly decreases VEGF expression. Shc, a downstream adaptor protein of the HER-2 signaling pathway has been identified as a critical switch for VEGF production showing that VEGF is a downstream target of the HER-2 signaling pathway. This shows that the effects of HER-2 on tumor cell behavior may be mediated in part through stimulation of angiogenesis. Angiogenesis is the growth of new blood vessels from pre-existing ones and contributes to the development of numerous types of tumors and their metastasis. VEGF, a well known pro-angiogenic factor is secreted by most tumor cells. VEGF stimulates angiogenesis by binding to its receptor VEGFR-2 which is expressed by both endothelial and tumor cells. Pertuzumab binds to the extracellular domain of HER-2 at sub-domain II thereby preventing receptor dimerization and signal transduction.

The oncoprotein HER-2 is also a ligandless member of the HER family of receptors and other members of this family are HER-1, HER-3 and HER-4. The absence of a HER-2 ligand makes it a preferred dimerization partner with other HER receptors. All members of the HER family have an extracellular domain, a single transmembrane domain and a cytoplasmic portion that contains a conserved tyrosine kinase domain flanked by a carboxyl terminal tail with autophosphorylation sites HER-2 is known to regulate the formation of neuromuscular synapses and also important in muscle spindle development. High levels of HER-2 causes dysregulation of the HER network resulting to transformation, tumorigenesis and resistance to cytotoxic effects of TNFα. HER-2 overexpressing breast cancers are biologically different from other breast cancers and are known to be resistant to hormonal agents, and have increased ability to metastasize to other organs of the body like the lung and brain. HER-2 upregulation is not only limited to breast cancers as its amplification has been reported in subsets of gastric, esophageal, ovarian, uterine, endometrial and lung cancers. HER-2 upregulation is always accompanied by VEGF upregulation both at the RNA and protein level and most drugs that target HER-2 are known to also down regulate VEGF expression. This implies that, the effects of HER-2 may partly be mediated by upregulation of VEGF. Immunization with both tumor and angiogenesis associated antigens showed synergistic effects. Tumor cells are known to up regulate the expression of VEGF and its receptors thereby stimulating angiogenesis.

BRIEF SUMMARY

Provided herein are compositions and methods for the treatment of cancers. In one embodiment a composition comprising a peptide that comprises an amino acid sequence ITMQCGIHQGQHPKIMICEMSF (SEQ ID NO: 1) is disclosed. The composition may have the two cysteine residues of the peptide are linked by a disulfide bond to form a cyclized peptide. The cyclized peptide may form a twisted, anti-parallel, β-sheet structure. The cyclized peptide may mimic the structure of amino acids 102 to 122 of native VEGF. In some embodiments the peptide may be in retro-inverso form. The two cysteine residues of the retroinverso peptide may also be linked by a disulfide bond to form a cyclized retro-inverso peptide. In some embodiments the peptide is capable of binding to a VEGF receptor. The VEGF receptor may be selected from the group consisting of VEGFR-1 (flt-1), VEGFR-2 (flk-1 or KDR), and VEGFR-3 (neurophilin-1 (NR-1)). In some embodiments the VEGF receptor is VEGFR-2.

In other embodiments the peptide further comprises a T-cell epitope selected from the group consisting of: KLLSLIKGVIVHRLEGVE (SEQ ID NO: 2); NSVDDALINSTIYSYFPSV (SEQ ID NO: 3); PGINGKAIHL VNNQSSE (SEQ ID NO: 4); QYIKANSKFIGITEL (SEQ ID NO: 5); FNNFTVSFWLRVPKVSASHLE (SEQ ID NO: 6); LSEIKGVIVHRLEGV (SEQ ID NO: 7); FFLL TRIL TIPQSLN (SEQ ID NO: 8); and TCGVGVRVRSRVNAANKKPE (SEQ ID NO: 9). In some embodiments the peptide further comprising a T-cell epitope may be immunogenic. The peptide further comprising a T-cell epitope may even further comprise a linker between the peptide and T-cell epitope. The linker may comprise a sequence that is between 1 and 15 amino acids in length. In some embodiments the linker may comprise an amino acid sequence of GPSL (SEQ ID NO: 10).

In yet another embodiment the composition may further comprise at least one HER-2 epitope selected from the group consisting of: TGTDMKLRLP ASPETHLDM (SEQ ID NO: ill; A VLDNGDPLNNTTPVTGASPGG (SEQ ID NO: 12); L WKDIFHKNNQLALTLIDTNRS (SEQ ID NO: 13); TLIDTNRSRACHPCSPMCKGSRCWGESSEDCQSLT (SEQ ID NO: 14); ALVTYNTDTFESMPNPEGRYT (SEQ ID NO: 15); PLHNQEVTAEDGTQRAEKCSKPCA (SEQ ID NO: 16); PESFDGDPASNTAPLQPE (SEQ ID NO: 17); LYISAWPDSLPDLSVFQNLQ (SEQ ID NO: 18); LFRN-PHQALLHTANRPEDE (SEQ ID NO: 19); CLPCHPECQPQNGSVTCFGPEADQCVACAHYKDP (SEQ ID NO: 20); KPDLSYMPIWKFPDEEGA (SEQ ID NO: 21); INGTHSCVDLDDKGCPAEQRAS (SEQ ID NO: 22); CHPECQPQNGSVTCFGPEADQCVACAHYKDPPFCV A (SEQ ID NO: 23); VACAHYKDPPFCVA (SEQ ID NO: 24); VARCPSGVKPDLSYMPIWKFPDEEGACQPL (SEQ ID NO: 25); IWKFPDEEGACQPL (SEQ ID NO: 26); LHCPALVTYNTDTFESMPNPEGRYTFGASCV (SEQ ID NO: 27); ACPYNYLSTDVGSCTLVCPLHNQEVTAEDGTQRCEK (SEQ ID NO: 28); CPLHNQEVTAEDGTQRCEK (SEQ ID NO: 29); and CPINCTHSCVDLDDKGCPAEQRAS (SEQ ID NO: 30).

In some embodiments the HER-2 epitope may be cyclized through a disulfide linkage between two cysteine residues. The HER-2 epitope may also be in retro-inverso form. In some embodiments the HER-2 epitope may be immunogenic. In still some embodiments the HER-2 epitope may further comprise a T-cell epitope selected from the group consisting of: KLLSLIKGVIVHRLEGVE (SEQ ID NO: 31); NSVDDALINSTIYSYFPSV (SEQ ID NO: 32); PGINGKAIHL VNNQSSE (SEQ ID NO: 33); QYIKANSKFIGITEL (SEQ ID NO: 34); FNNFTVSFWLRVPKVSASHLE (SEQ ID NO: 35); LSEIKGVIVHRLEGV (SEQ ID NO: 36); FFLLTRILTIPQSLN (SEQ ID NO: 37); and TCGVGVRVRSRVNAANKKPE (SEQ ID NO: 38). In some embodiments the HER-2 epitope further comprising a T-cell epitope may even further comprise a linker 1 to 15 amino acids in length. The linker may comprise an amino acid sequence of GPSL (SEQ ID NO: 10).

Also provided herein are isolated antibodies that specifically binds to the polypeptides disclosed herein. In some embodiments the antibody may be monoclonal, humanized, or both. In some embodiments an antigen-binding fragment of the antibody is contemplated.

Also provided herein are methods of treating cancers in subjects comprising administering a pharmaceutical composition to the subject, the pharmaceutical composition comprising a pharmaceutically acceptable vehicle, and at least one composition disclosed herein.

It is to be understood that both the foregoing brief summary and the following detailed description are exemplary and explanatory only and are not restrictive of the embodiments disclosed herein, as claimed.

BRIEF DESCRIPTION OF THE SEVERAL VIEWS OF THE DRAWING

The accompanying drawings, which are incorporated in and constitute a part of this specification, illustrate some embodiments disclosed herein, and together with the description, serve to explain principles of the embodiments disclosed herein.

FIG. 1 discloses SEQ ID NO: 39.

FIG. 2 discloses SEQ ID NO: 39 and 40, respectively, in order of appearance.

FIG. 3D shows a binding decrease of the extracellular domain of VEGFR-2 to VEGF mimic peptides was observed when rhVEGF was incubated with KDR-fc prior to injection, confirming that the extracellular domain of VEGFR-2 binding sites to VEGF mimic peptides and VEGF are located in the same region.

FIG. 4(A-D) shows in FIG. 4A that biotinylated VEGFR-2 specific peptides as detected by streptavidin Texas red after incubation with peptide-pre-incubated cells but not on the naive ones indicates binding and internalization in HUVEC and in a tumor cell line expressing only his receptor (293-KDR); FIGS. 4B and 4C show the binding of the peptide was seen unevenly distributed over HUVEC where the receptors are known to be expressed in clusters and reside in an endosomal population close to the plasma membrane; and FIG. 4D shows that in the case of 293-KDR cells, the binding could be seen all over the expressing cells because expression is uniform throughout the cell surface, which explains the increased accumulation in some cells (193-KDR) and the clustering in others (HUVECS). These results clearly illustrate that the VEGF peptides are specific to VEGFR-2 and recognize cells that are known to express the receptor in a pattern which is consistent with its known distribution.

FIG. 5(A-B) shows that all three VEGF mimic peptides were able to decrease the level of receptor phosphorylation of KDR (FIG. 5A) and pY42/44 and CD31 (FIG. 5B).

FIG. 6(A-B) shows in FIG. 6A that the degree of VEGFR-2 phosphorylation is notably increased in the presence of exogenous VEGF (10 ng/ml) and decreased when an exogenous receptor (KDR-Fc at 100 ng/ml) was used as a competitor; and FIG. 6B shows the quantification of VEGFR-2 phosphorylation using the Human Phospho-VEGF R2/KDR DuoSet IC kit.

FIG. 7 shows that all VEGF mimics can inhibit HUVEC proliferation in a dose dependent way and that the conformational peptide VEGF-P3(CYC) demonstrated the highest inhibitory effect.

FIG. 8(A-B) shows in picture (FIG. 8A) and graphical format (FIG. 8B) that network formation is VEGF dependent whereas a cell network with several sprout points is more evident in the VEGF treated HUVEC than the non-VEGF treated HUVEC and that a decrease in the network branching and tube formation was observed in VEGF treated HUVEC in the presence of VEGF mimic peptides and no significant effect was seen with the irrelevant control.

FIG. 9(A-B) shows in picture (FIG. 9A) and graphical format (FIG. 9B) that cells were able to migrate towards the scratched area in higher number when exogenous rhVEGF was added compared to the absence VEGF and that all three VEGF mimic peptides demonstrated ability of inhibiting HUVEC migration at similar levels (approximately 50%) of the small VEGFR-2 tyrosine kinase inhibitor (SU1498) at a standard concentration, indicating that VEGF mimic peptides are capable of blocking the VEGF dependent migration in endothelial cells.

FIG. 10 shows that when a promiscuous T cell epitope, MVF 288-302, which has been demonstrated to enhance immune response, was incorporated into VEGF mimic peptides and used for raising antibodies in rabbits, all three constructions of VEGF mimic peptides demonstrated high immunogenicity and were able to recognize the entire protein when the rhVEGF was used as an antigen in an ELISA assay.

FIG. 11(A-C) shows the competitive ELISA results for anti-MVF-VEGF 102-122 (FIG. 11A), anti-MVF-VEGF-P3 (NC) (FIG. 11B), and anti-MVF-VEGF-P3(CYC) (FIG. 11C).

FIG. 12 shows that anti-VEGF-P3(CYC) demonstrated the highest inhibition and anti-VEGF-P3(NC) seems to be slightly more efficient than the natural sequence.

FIG. 13(A-E) shows the anti-proliferative effects of combination treatment with HER-2 and VEGF peptide mimics. SK-BR-3 (FIG. 13A), BT474 (FIG. 13B), MDA-468 (FIG. 13C), and TS/A (FIG. 13D) cells were incubated with HER-2 peptide, VEGF peptides, Trastuzumab and irrelevant peptide. Bioconversion of MTT was used to estimate the number of active tumor cells remaining after 3 days. Peptides were added at four different concentrations using the above mentioned cell lines. The proliferation inhibition rate was calculated using the formula (ODnormal Untreated-OD peptides or Ab)/ODnormal untreated×100. Error bars represent SD. FIG. 13E shows BT-474 cells were treated in the same manner as in FIG. 13A-D and treated with HER-2 peptide, VEGF peptides or combination of both. Trastuzumab and irrelevant peptide were used as positive and negative controls. Rate of inhibition was calculated using the same formula in FIG. 13A-D and all results represents the average of three different experiments. Error bars represent SD of the mean.

FIG. 14(A-B) shows the effects of combination treatment on cell viability and HER-2 phosphorylation. FIG. 14A shows BT474 cells were incubated with media alone, HER-2 peptide, VEGF peptides, trastuzumab, and irrelevant peptide. The number of viable cells remaining after three days was determined using the aCella-TOX reagent kit and all instructions were done according to manufacturer's instructions. Cell viability is given as a percentage of untreated cells. Data points represent the mean of three independent experiments. Error bars represent SD. Results represent average of three different experiments. FIG. 14B shows BT-474 cells were incubated with 100 ug of HER-2 and VEGF peptides before being exposed to HRG (HER-3 activating ligand) for 10 minutes and lysed. Phosphorylated HER-2/neu was determined by indirect ELISA and percent inhibition was calculated as in FIG. 14A above. AG825 (Calbiochem) a potent HER-2 phosphorylation inhibitor was used as a positive control. Results represent average data from three different experiments. Error bars represent SD of the mean.

FIG. 15(A-D) shows in vivo anti-tumor and anti-angiogenic effects in a transplantable tumor model. Wild type BALB/c mice (n=5), at the age of 5-6 weeks was challenged with TUBO cells that were derived from BALB-neuT mice which are transgenic for the rat HER-2/neu oncogene, and were treated intravenously with HER-2 and VEGF peptide mimics, and scrambled irrelevant peptide, tumor measurements were performed twice a week using calipers. The data are presented as the average tumor size per group and are reported as $mm^3$ for combination treatment with HER-2 and L amino acid VEGF peptide (FIG. 15A) and for HER-2 peptide with D-amino acid VEGF peptide (FIG. 15B) and the group receiving the HER-2 in combination with the D-amino VEGF peptide showed significant prevention of tumor growth compared with the untreated group or the group receiving Irrelevant peptide (*$p<0.003$). Also, the same group treated both HER-2 and D-amino acid VEGF peptide showed the greatest percentage tumor free (FIG. 15C) and lowest percentage tumor weight (FIG. 15D) as compared to the control group with a p value of 0.05 (#) Error bars represent mean standard deviations.

FIG. 16(A-D) shows antibody responses elicited by peptide vaccines in outbred rabbits. FIGS. 16B and 16C show the anti-proliferative effects of combination treatment with HER-2 and VEGF peptide mimics. FIG. 16B-C shows BT474 (FIG. 16B) and MDA-468 (FIG. 16C) cells were incubated with HER-2 peptide, VEGF peptides, Trastuzumab and irrelevant peptide. Bioconversion of MTT was used to estimate the number of active tumor cells remaining after 3 days. Peptides were added at four different concentrations using the above mentioned cell lines. The proliferation inhibition rate was calculated using the formula (ODnormal Untreated-OD peptides or Ab)/ODnormal untreated×100. Error bars represent SD.

FIG. 17(A-B) shows the effects of combination treatment on cell viability and HER-2 phosphorylation.

FIG. 19(A-E) shows the effects of peptide treatment in a transplantable tumor model.

FIG. 21(A-D) shows that the VEGF peptide treatment also appeared to cause a decrease in blood flow to the tumors thereby limiting their size increase (FIG. 21A), and FIGS. 21C and 21D show normalization of the tumor vasculature, while FIG. 21B shows that immunization and treatment with irrelevant peptide only decreases tumor size but no effect on blood supply.

DETAILED DESCRIPTION

Figure 1:
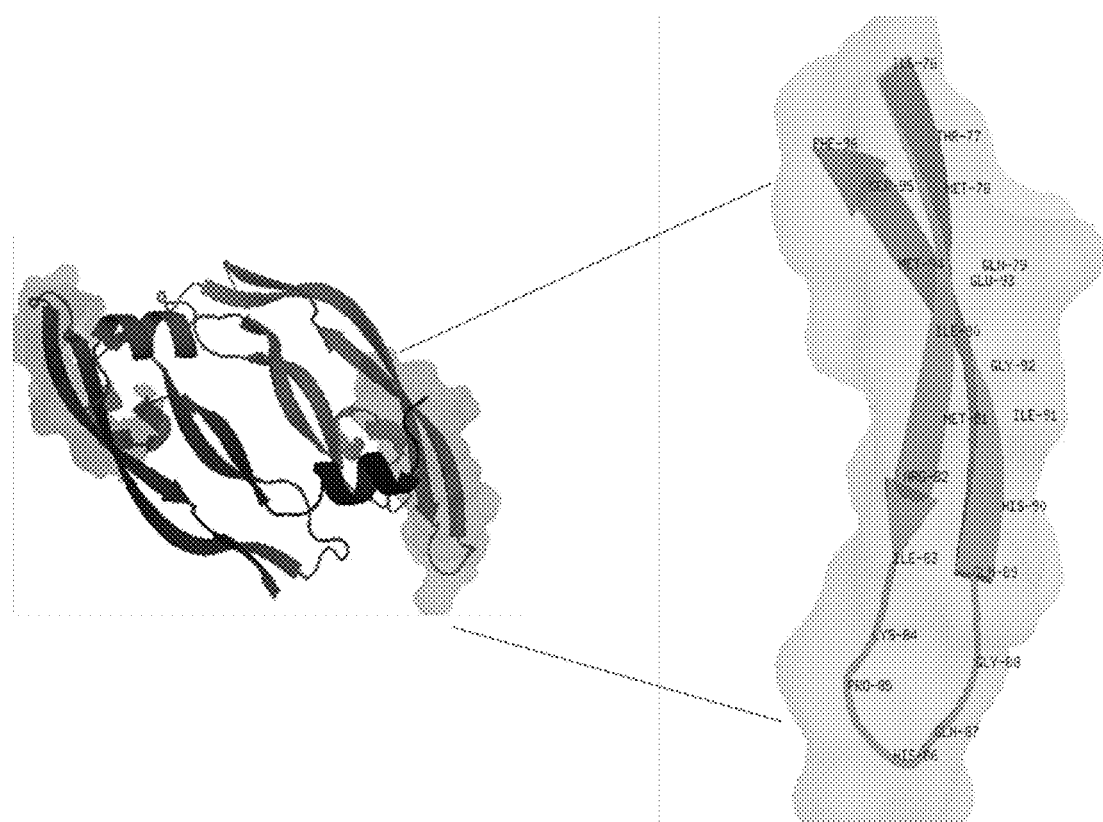
FIG. 1 shows that although the VEGF residues critical for antibody binding are distinct from those important for high-affinity receptor binding, they occupy a common region on VEGF demonstrating that the neutralizing effect of antibody binding results from steric blocking of VEGF-receptor interactions and only a small number of the residues buried in the VEGF-Fab interface are critical for high-affinity binding and are concentrated in one continuous segment of polypeptide loop between β5-β6.

The embodiments disclosed herein will now be described by reference to some more detailed embodiments, with occasional reference to the accompanying drawings. The embodiments disclosed herein may, however, be embodied in different forms and should not be construed as limited to the embodiments set forth herein. Rather, these embodiments are provided so that this disclosure will be thorough and complete, and will fully convey the scope of the embodiments disclosed herein to those skilled in the art.

Unless otherwise defined, all technical and scientific terms used herein have the same meaning as commonly understood by one of ordinary skill in the art to which the embodiments disclosed herein belong. The terminology used in the description herein is for describing particular embodiments only and is not intended to be limiting of the embodiments disclosed herein. As used in the description and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments disclosed herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments disclosed herein are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Provided herein are compositions and methods for the treatment of cancers. In one embodiment a composition comprising a VEGF peptide that comprises an amino acid sequence ITMQCGIHQGQHPKIMICEMSF (SEQ ID NO: 1) is disclosed. The VEGF peptide may have its two cysteine residues linked by a disulfide bond to form a cyclized VEGF peptide. The cyclized VEGF peptide may form a twisted, anti-parallel, β-sheet structure. The cyclized VEGF peptide may mimic the structure of amino acids 102 to 122 of native VEGF or amino acids 76 to 96 of the VEGF crystal structure. In some embodiments the VEGF peptide may be in retro-inverso form. The two cysteine residues of the retro-inverso VEGF peptide may also be linked by a disulfide bond to form a cyclized retro-inverso VEGF peptide. The retro-inverso modification comprises the reversal of all amide bonds within the peptide backbone. This reversal may be achieved by reversing the direction of the sequence and inverting the chirality of each amino acid residue by using D-amino acids instead of the L-amino acids. This retro-inverso isomer form may retain planarity and conformation restriction of at least some of the peptide bonds. For example, the non-retro-inverso form may be indicated as NH$_2$L[ITMQCGIHQGQHPKIMICEMSF]-COOH (SEQ ID NO: 1). The retro-inverso form may be indicated as NH$_2$-D[FSMECIMIKPHQGQHIGCQMTI]-COOH. In some embodiments the peptide is capable of binding to a VEGF receptor. The VEGF receptor may be selected from the group consisting of VEGFR-1 (flt-1), VEGFR-2 (flk-1 or KDR), and VEGFR-3 (neurophilin-1 (NR-1)). In some embodiments the VEGF receptor is VEGFR-2.

In other embodiments the VEGF peptide further comprises a T-cell epitope selected from the group consisting of: KLLSLIKGVIVHRLEGVE (SEQ ID NO: 2); NSVDDAL-INSTIYSYFPSV (SEQ ID NO: 3); PGINGKAIHL VNNQSSE (SEQ ID NO: 4); QYIKANSKFIGITEL (SEQ ID NO: 5); FNNFTVSFWLRVPKVSASHLE (SEQ ID NO: 6); LSEIKGVIVHRLEGV (SEQ ID NO: 7); FFLLTRILT-IPQSLN (SEQ ID NO: 8); and TCGVGVRVRSRV-NAANKKPE (SEQ ID NO: 9). In some embodiments the VEGF peptide further comprising a T-cell epitope may be immunogenic. It will be understood that any suitable T-cell epitope may be used. For example, a promiscuous T-cell epitope may be used. As used herein a "promiscuous" T-cell epitope is one which promotes release of cytokines that assists in bypassing MHC restriction. It will be further understood that any suitable linker may be used. For example, depending upon the T-cell epitope used, the VEGF or HER-2 epitopes or peptides may be linked to either the amino or the carboxy terminus of the T-cell epitope. The location and selection of the T-cell epitope depends on the structural characteristics of the VEGF or HER-2 B epitopes or peptides, whether alpha helical or beta-turn or strand. Methods for selecting suitable T-cell epitopes are described in Kaumaya et al., "De Novo" Engineering of Peptide Immunogenic and Antigenic Determinants as Potential Vaccines," in Peptides, Design, Synthesis and Biological Activity (1994), pp. 133-164, which is specifically incorporated herein by reference. A summary of the immune responses elicited a variety of T-cell epitopes containing B-cell epitope chimeras was presented in a review titled "Synthetic Peptides: Dream or Reality" by Kaumaya et al., and published in Peptides in Immunology, Wiley and Sons, Ltd. (1996). In some examples, the T-cell epitope may be from about 14 to about 22, about 15 to 21, or about 16 amino acids in length.

The VEGF peptide further comprising a T-cell epitope may even further comprise a linker between the VEGF peptide and T-cell epitope. The linker may comprise a sequence that is between 1 and 15 amino acids in length. In some embodiments the linker may comprise an amino acid sequence of GPSL (SEQ ID NO: 10).

In yet another embodiment the composition may further comprise at least one HER-2 epitope selected from the group consisting of: TGTDMKLRLPASPETHLDM (SEQ ID NO: 11); AVLDNGDPLNNTTPVTGASPGG (SEQ ID NO: 12); L WKDIFHKNNQLALTLIDTNRS (SEQ ID NO: 13); TLIDTNRSRACHPCSPMCKGSRCWGESSEDCQSLT (SEQ ID NO: 14); ALVTYNTDTFESMPNPEGRYT (SEQ ID NO: 15); PLHNQEVTAEDGTQRAEKCSKPCA (SEQ ID NO: 16); PESFDGDPASNTAPLQPE (SEQ ID NO: 17); LYISAWPDSLPDLSVFQNLQ (SEQ ID NO: 18); LFRN-PHQALLHTANRPEDE (SEQ ID NO: 19); CLPCHPEC-QPQNGSVTCFGPEADQCVACAHYKDP (SEQ ID NO: 20); KPDLSYMPIWKFPDEEGA (SEQ ID NO: 21); INGTHSCVDLDDKGCPAEQRAS (SEQ ID NO: 22); CHPECQPQNGSVTCFGPEADQCV ACAHYKDPPFCV A (SEQ ID NO: 23); VACAHYKDPPFCVA (SEQ ID NO: 24); VARCPSGVKPDLSYMPIWKFPDEEGACQPL (SEQ ID NO: 25); IWKFPDEEGACQPL (SEQ ID NO: 26); LHCPALVTYNTDTFESMPNPEGRYTFGASCV (SEQ ID NO: 27); ACPYNYLSTDVGSCTLVCPLHNQEVTAE-DGTQRCEK (SEQ ID NO: 28); CPLHNQEVTAE-DGTQRCEK (SEQ ID NO: 29); and CPINCTHSCVDLD-DKGCPAEQRAS (SEQ ID NO: 30). In other examples, the HER-2 epitopes may be the retro-inverso isomers of the HER-2 epitopes. The retro-inverso modification comprises the reversal of all amide bonds within the peptide backbone. This reversal may be achieved by reversing the direction of the sequence and inverting the chirality of each amino acid residue by using D-amino acids instead of the L-amino acids. This retro-inverso isomer form may retain planarity and conformation restriction of at least some of the peptide bonds. For example, the non-retro-inverso form may be indicated as NH$_2$-L[LHCPALVTYNTDTFESMPNPE-GRYTFGASCV]-COOH (SEQ ID NO: 27). The retro-inverso form may be indicated as NH$_2$D[VCSAG-FTYRGEPNPMSEFTDTNYTVLAPCHL]-COOH.

In some embodiments the HER-2 epitope may be cyclized through a disulfide linkage between two cysteine residues. The cyclized HER-2 epitope may also be in retro-inverso form. In still some embodiments the HER-2 epitope may further comprise a T-cell epitope selected from the group consisting of: KLLSLIKGVIVHRLEGVE (SEQ ID NO: 31); NSVDDALINSTIYSYFPSV (SEQ ID NO: 32); PGINGKAIHLVNNQSSE (SEQ ID NO: 33); QYIKANSK-FIGITEL (SEQ ID NO: 34); FNNFTVSFWLRVPK-VSASHLE (SEQ ID NO: m; LSEIKGVIVHRLEGV (SEQ ID NO: 36); FFLL TRIL TIPQSLN (SEQ ID NO: 37); and TCGVGVRVRSRVNAANKKPE (SEQ ID NO: 38). In some embodiments the HER-2 epitope further comprising a T-cell epitope may be immunogenic. In some embodiments the HER-2 epitope further comprising a T-cell epitope may even further comprise a linker 1 to 15 amino acids in length. The linker may comprise an amino acid sequence of GPSL (SEQ ID NO: 10). In other examples, the linker may be a peptide of from about 2 to about 15 amino acids, about 2 to about 10 amino acids, or from about 2 to about 6 amino acids in length.

Non-conservative amino acid substitutions and/or conservative substitutions may be made to the VEGF or HER-2 epitopes or peptides. Substitutions are conservative amino acid substitutions when the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine and isoleucine, with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

In some examples, the deletions and additions are located at the amino terminus, the carboxy terminus, or both, of one of the sequences shown above. For example, the peptide equivalent has an amino acid sequence which is at least 70% identical, at least 80% identical, at least 90% identical, or at least 95% identical to the corresponding peptide sequences. Sequences which are at least 90% identical have no more than 1 alteration, i.e., any combination of deletions, additions or substitutions, per 10 amino acids of the reference sequence. Percent identity is determined by comparing the amino acid sequence of the variant with the reference sequence using MEGALIGN project in the DNA STAR pro-gram.

Also provided herein are isolated antibodies that specifically binds to the polypeptides disclosed herein. In some embodiments the antibody may be monoclonal, humanized, or both. In some embodiments an antigen-binding fragment of the antibody is contemplated. The peptides and compositions comprising the peptides may be useful immunogens for inducing production of antibodies that interact with and bind to VEGF or the extracellular domain of the HER-2 protein. The chimeric peptides may also be useful as laboratory tools for detecting antibodies to VEGF and HER-2 protein in a subject's sera. The chimeric peptides may invoke an antibody response in a subject and that such antibodies may (a) immunoprecipitate VEGF or HER-2 protein, (b) bind to intact VEGF or HER-2 receptor on ER-2 overexpressing cells in culture, and (c) reduce proliferation of VEGF and HER-2 overexpressing cells in vitro. The chimeric peptides may also be used to immunize a subject and retard or prevent tumor development. The chimeric peptides may be used in vaccines to provide a protective effect.

The epitopes and peptides may be synthesized using commercially available peptide synthesizers. For example, epitopes and peptides may be synthesized co-linearly with the Th epitope to form a chimeric peptide. Peptide synthesis may be performed using Fmoc/t-But chemistry. The epitopes and peptides may be cyclized in any suitable manner. For example, disulfide bonds may be achieved using differentially protected cysteine residues, iodine oxidation, the addition of water to boost Acm removal and the concomitant formation of a disulfide bond, and/or the sily chloride-sulfoxide method.

The epitopes and peptides may also be produced using cell-free translation systems and RNA molecules derived from DNA constructs that encode the epitope or peptide. Alternatively, the epitopes or chimeric peptides are made by transfecting host cells with expression vectors that comprise a DNA sequence that encodes the respective epitope or chimeric peptide and then inducing expression of the polypeptide in the host cells. For recombinant production, recombinant constructs comprising one or more of the sequences which encode the epitope, chimeric peptide, or a variant thereof are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

The epitopes and peptides may be expressed in suitable host cells, such as for example, mammalian cells, yeast, bacteria, insect cells or other cells under the control of appropriate promoters using conventional techniques. Suitable hosts include, but are not limited to, *E. coli, P. pastoris*, Cos cells and 293 HEK cells. Following transformation of the suitable host strain and growth of the host strain to an appropriate cell density, the cells are harvested by centrifugation, disrupted by physical or chemical means, and the resulting crude extract retained for further purification of the epitope or peptide.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate the recombinant polypeptide.

To produce glycosylated epitopes and chimeric peptides, recombinant techniques may be used. For example, mammalian cells such as, Cos-7 and Hep-G2 cells be employed in the recombinant techniques. Alternatively, glycosylated epitopes and chimeric peptides may be produced using standard Fmoc/t-But synthesis. For example, one or more sugar units can be added to peptides using a chemoenzymatic approach employing endo-β-N-aceylglu cosaminidases as the key enzyme for oligosaccharide transfer.

Naturally occurring variants of the epitopes and peptides may also be isolated by, for example, by screening an appropriate cDNA or genomic library with a DNA sequence encoding the polypeptide.

In accordance with yet other embodiments, isolated polynucleotides which encode the epitopes and peptides discussed herein are provided. The present polynucleotides also encompass polynucleotides having sequences that are capable of hybridizing to the nucleotide sequences of the VEGF and HER-2 epitopes or peptides under stringent conditions, and/or highly stringent conditions. Hybridization conditions are based on the melting temperature ($T_m$) of the nucleic acid binding complex or probe, as described in Berger and Kimmel (1987) Guide to Molecular Cloning Teclmiques, Methods in Enzymology, vol. 152, Academic Press. The term "stringent conditions, as used herein, is the "stringency" which occurs within a range from about $T_m$-5 (5° below the melting temperature of the probe) to about 20° C. below $T_m$. As used herein "highly stringent" conditions employ at least 0.2×SSC buffer and at least 65° C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Polynucleotides comprising sequences encoding a VEGF or HER-2 B epitope or a chimeric peptide of the present invention may be synthesized in whole or in part using chemical methods or recombinant methods which are suitable. Polynucleotides which encode a VEGF or HER-2 B epitope or peptide may be obtained by screening a genomic library or cDNA library with antibodies immunospecific for the VEGF or HER-2 protein to identify clones containing such polynucleotide.

The polynucleotides are useful for producing a VEGF or HER-2 B epitope or a peptide. For example, an RNA molecule encoding a multivalent peptide may be used in a cell-free translation systems to prepare such polypeptides. Alternatively, a DNA molecule encoding a VEGF or HER-2B epitope or a peptide may be introduced into an expression vector and used to transform cells. Suitable expression vectors include, but are not limited to, chromosomal, non-chromosomal and synthetic DNA sequences, e.g., derivatives of SV40, bacterial plasmids, phage DNAs; yeast plasmids, vectors derived from combinations of plasmids and phage DNAs, viral DNA such as vaccinia, adenovirus, fowl pox virus, pseudorabies, baculovirus, and retrovirus. The DNA sequence may introduced into the expression vector by any suitable procedure.

In accordance with further embodiments, recombinant constructs comprising one or more of the polynucleotides encoding one or more VEGF or HER-2 B epitopes or peptides are provided. Suitable constructs include, for example, vectors, such as a plasmid, phagemid, or viral vector, into which a sequence that encodes the VEGF or HER-2 epitope or peptide has been inserted. In the expression vector, the DNA sequence which encodes the epitope or peptide is operatively linked to an expression control sequence, i.e., a promoter, which directs mRNA synthesis.

Representative examples of such promoters, include the LTR or SV40 promoter, the E. coli lac or trp, the phage lambda PL promoter and other promoters known to control expression of genes in prokaryotic or eukaryotic cells or in viruses. The expression vector may also contain a ribosome binding site for translation initiation and a transcription terminator. For example, the recombinant expression vectors also may include an origin of replication and a selectable marker, such as for example, the ampicillin resistance gene of E. coli to permit selection of transformed cells, i.e., cells that are expressing the heterologous DNA sequences. The polynucleotide sequence encoding the VEGF or HER-2 epitope or the peptide may be incorporated into the vector in frame with translation initiation and termination sequences. For example, the polynucleotide may further encode a signal sequence which is operatively linked to the amino terminus of the VEGF or HER-2 epitope or peptide.

The polynucleotides encoding the VEGF or HER-2B epitopes or peptides may be used to express recombinant peptide using suitable techniques. Such techniques include, but are not limited to, those described in Sambrook, J. et al (1989) Molecular Cloning A Laboratory Manual, Cold Spring Harbor Press, Plainview, N.Y. and Ausubel, F. M. et al. (1989) Current Protocols in Molecular Biology, John Wiley & Sons, New York, N.Y. Polynucleotides encoding the VEGF or HER-2 epitopes or peptides may also be used to immunize subjects.

In accordance with yet further embodiments, methods of treating cancer are provided. The methods comprise administering a pharmaceutical composition to a subject. In other embodiments, vaccines comprising at least one peptide, multivalent peptide, or both, of the polynucleotide which encodes the same are provided. The pharmaceutical composition comprises a pharmaceutically acceptable vehicle and at least one peptide, multivalent peptide, or both, or the poly-nucleotide which encodes the same, as described herein. Pharmaceutically acceptable vehicles, include, but are not limited to pharmaceutically acceptable carriers, excipients or diluents. These vehicles are generally nontoxic to subjects at the dosages and concentrations employed.

In addition to the epitopes, peptides, and chimeric peptides or the polynucleotide which encodes the same, other components, such as a vehicle for antigen delivery and immunostimulatory substances designed to enhance the protein's immunogenicity are included in the pharmaceutical composition. Examples of vehicles for antigen delivery include aluminum salts, water-in-oil emulsions, biodegradable oil vehicles, oil-in-water emulsions, biodegradable microcapsules, and liposomes. For the vaccines which comprise the chimeric peptide, a suitable vehicle for antigen delivery is a biodegradable microsphere, which may be comprised of poly (D,L-lactide-co-glycolide) (PLGA).

While any suitable vehicle may be employed in the pharmaceutical compositions of this invention, the type of carrier will vary depending on the mode of administration and whether a substantial release is desired. For parenteral administration, such as subcutaneous injection, the carrier may be water, saline, alcohol, a fat, a wax, or a buffer. Biodegradable microspheres (e.g., polylactic galactide) may also be employed as vehicles for the pharmaceutical compositions of this invention. According to some embodiments, the pharmaceutical composition comprises an adjuvant.

The VEGF and HER-2 epitopes and peptides and the polynucleotides which encode the same may be useful for enhancing or eliciting, in a subject or a cell line, a humoral response and, preferably, a cellular immune response (e.g., the generation of antigen-specific cytolytic T cells). In some examples the subject is a human. A subject may be afflicted with cancer or other cancer involving HER-2, such as breast cancer, or may be normal (i.e., free of detectable disease and infection). The pharmaceutical compositions and vaccines may be useful for treating women who have a family history of breast cancer or who have had breast tumors removed. According to some embodiments, "treating" means inhibiting or slowing or retarding the growth of the tumor. Such cancers include, but are not limited to, breast, lung, ovarian, bladder and prostate. In some examples, multiple intramuscular injections, at three week intervals, are used to administer the pharmaceutical composition.

Also provided herein are methods of treating cancers in subjects comprising administering a pharmaceutical composition to the subject, the pharmaceutical composition comprising a pharmaceutically acceptable vehicle, and at least one composition disclosed herein.

EXAMPLES

Engineered conformation-dependent VEGF mimic peptides are effective in inhibiting VEGF signaling pathways.

Angiogenesis, or formation of new blood vessels, is crucial to cancer tumor growth. Tumor growth, progression and metastasis are critically influenced by the production of the pro-angiogenic factor vascular endothelial factor (VEGF). Promising anti-angiogenic drugs are currently available; however, their susceptibility to drug resistance and long-term toxicity make the need for further development of reliable and safe angiogenic inhibitors. In this work, novel peptides were designed to mimic the VEGF binding site to its receptor VEGFR-2. The VEGF mimic peptides were evaluated as inhibitors in several assays in which VEGF dependent signaling pathways are observed. The VEGF conformational peptide mimic, VEGF-P3(CYC), include two extra cysteine residues, which upon cyclization constrains the peptide in a loop conformation, and the ends were twisted, in order to better mimic the anti-parallel structure in the VEGF. The engineered cyclic VEGF mimic peptide demonstrated the highest affinity to VEGFR-2 by surface plasmon resonance assay and when it is used as inhibitor, it prevents VEGFR-2 phosphorylation. VEGF-P3 (CYC), also shows the highest inhibitory effects when compared to unstructured peptides in several angiogenic in vitro assays such as endothelial cell proliferation, migration and network formation. These results indicate that the structure based design is important to the development of this peptidomimetic and to its anti-angiogenic effects. The VEGF-P3(CYC) is the best peptide candidate so far for the development of a peptidomimetic angiogenic inhibitor, and further evaluated in in vivo animal models is warranted.

The main goal of this work is to create molecules that would retain the structural similarity with the binding site region and demonstrate bioactivity in vivo. Peptides are excellent candidates for drug design once peptides demonstrated better target specificity and less susceptibility to drug resistance than other small molecules. They also demonstrated advantages like lower developing and manufacturing costs, improved organ or tumor penetration and higher activity per mass when compared to antibodies or large proteins.

The crystal structure of the complex between VEGF and the Fab fragment of a humanized antibody, and analysis of the contact residues on both sides of the interface was published by Muller et al. Zilberberg et al., also identified that the sequence 79-93 of VEGF is involved in the interaction with VEGF receptor-2. Although the VEGF residues critical for antibody binding are distinct from those important for high-affinity receptor binding, they occupy a common region on VEGF demonstrating that the neutralizing effect of antibody binding results from steric blocking of VEGF-receptor interactions and only a small number of the residues buried in the VEGF-Fab interface are critical for high-affinity binding and are concentrated in one continuous segment of polypeptide loop between β5-β6 (FIG. 1). Several residues are important for VEGF receptor binding, including Met 81, Ile 83, Lys 84, Pro 85, Gln 89, and Gly92. We have selected to use a peptide encompassing residues 102-122 (numbered as 76-96 in the crystal structure) which mimics the overlapping VEGF binding sites to VEGFR-2 and Avastin.

Peptide Synthesis. Peptides were synthesized on Milligen/Biosearch 9600 solid-phase peptide synthesizer (Bedford, Mass.) using Fmoc/t-But chemistry as previously described. In case of the synthesis of VEGF102-122 preloaded Fmoc-Phe-CLEAR acid resin (0.41 mmol/gm was used while VEGF-P3 and MVF-VEGF-P3 were synthesized using CLEAR amide resin (0.32 mmol/gm) (Peptides International, Louisville, Ky.). Peptide P3 were acetylated on resin, using acetyl imidazole reagent as reported earlier. The MVF-GPSL sequence ("GPSL" disclosed as SEQ ID NO: 10) was added on peptide resin of the H2N-VEGF-P3. All peptides were cleaved from the resin using the cleavage reagent B (Trifluoroacteic acid:Phenol:Water:Triisopropyl silane 90:4:4:2) and crude peptides were purified on preparative RP-HPLC (Reverse Phase-High Pressure Liquid Chromatography) using Vydac C-4 column and acetonitrile-water (0.1% TF A) gradient system. All fractions were analyzed on analytical RP-HPLC and characterized by MALDI (Matrix Assisted Laser Desorption Ionization mass spectroscopy) at CCIC (Campus Chemical Instrumentation Center, The Ohio State University, Columbus, Ohio). RP-HPLC fractions showing same mass spectrum peak were pooled together and lyophilized. RP-HPLC pure peptides MVF-VEGF-P3, VEGF-P3 containing two Cys residues in each peptide were cyclized using acetic acid-iodine method, further purified on RP-HPLC and characterized by mass spectroscopy using established protocol as reported earlier. Amino acid sequences and molecular weight of all peptides and their molecular weights are shown in Table 1 (Table 1 discloses SEQ ID NOS 39, 41 and 40, respectively, in order of appearance).

Cell lines and Reagents. All culture media, FBS, and supplements were purchased from Invitrogen Life Technologies (San Diego, Calif.). HUVEC were purchased from GlycoTech and cultivated in F-12K Nutrient Mixture-Kaighn's Modification (F-12K) supplemented with 20% FBS, heparin (100 μg/ml) and Endothelial (complement) cell growth factor supplement (ECGS) (50 μg/ml). 293/KDR cells were purchased from SibTech, Inc (Brookfield, Conn.) and cultivated in Dulbecco's Modified Eagle Medium (DMEM) supplemented with 10% FBS and puromycin (0.375 μg/mL). Cells were incubated in a 37° C. humidified 5% $CO_2$ incubator.

Surface Plasma Resonance. Binding assays were performed using a Biacore 3000 instrument (Pharmacia Biosensor, Uppsala, Sweden). The experiments were performed at room temperature using HBS-EP buffer (25 mM HEPES, pH 7.4, 150 nM NaCl, 3.4 mM EDTA, and 0.005% surfactant P20). Peptides were coupled onto CM5 chip surfaces at 10 μL/min using a standard amine coupling protocol with EDC (N-ethyl-N'-[dimethylaminopropyl]carbodiimide)/NHS (N-hydroxysuccinimide). KDR-Fc (R&D System) at several concentrations in HBS-EP buffer. Was injected at a flow rate of 10 µL/min. Data analysis was performed with BIAsimulation software version 3.1 (Pharmacia Biosensor). For competition assay KDR-Fc and rhVEGF (R&D System) were mixed in HBS-EP and incubated 30 minutes at room temperature and this mixture was injected over the chip where peptides were immobilized. To obtain measurement of anti-peptides binding affinities similar a experiment was carried out, but rhVEGF was immobilized onto CM5 chip surface and anti-peptides were injected at several concentrations.

Circular dichroism spectroscopy. Circular dichroism (CD) measurements were performed on an AVIV model 62A DS instrument. All spectral measurements were obtained at 25° C. under continuous nitrogen purging of the sample chamber, using a quartz cuvette of 0.1 cm path length. Spectral measurements of VEGF-P3(NC) and VEGF-P3 (CYC) were obtained at a concentration of 100 µM in water. Molar ellipticity values were calculated using the formula $_{M,\lambda}=(\theta \times 100 \times M_r)/(n \times c \times l)$, where θ is the recorded ellipticity, $M_r$ the molecular weight of the peptide, n the number of amino acid residues in peptide, c the peptide concentration (mg/mL) and l is the path length of cuvette.

Active immunization of rabbits. New Zealand White rabbits were immunized with 1 mg of peptide dissolved in ddH$_2$O emulsified (1:1) in Montanide ISA720 vehicle (Sepic) with 100 µg of N-acetylglucosamine-3-yl-acetyl-1-alanyl-d-isoglutamine (nor-MDP). Rabbits were boosted with the respective doses at 3 week intervals. Rabbit blood was collected via the central auricular artery and sera tested for antibody titers. Anti-peptide antibodies were purified by affinity chromatography using a Protein A/G column (Pierce) from high titer antibody sera.

ELISA for anti-VEGF antibodies. Plates were coated overnight at 4° C. with 100 µl of 2 µg/ml rhVEGF (R&D System), washed four times with 0.1% Tween 20/PBS, and blocked with of 100 µl of 1% BSA/PBS for 2 h at room temperature. Plates were washed four times with 0.1% Tween 20/PBS. Anti-peptide sera were added at several dilutions and incubated 2 hours at room temperature. Plates were washed four times with 0.1% Tween 20/PBS, a 1/500 dilution of goat-anti-rabbit IgG HRP was added and incubated 1 h. Detection was done using ABTS substrate and absorbance reading at 415 nm. Ab titers were determined as previously described and defined as the reciprocal of the highest serum dilution with an absorbance of 0.2 or greater after subtracting background.

Direct peptide-cell binding assay. The peptide VEGF-P3-CYC was biotinylated at the N-terminus during synthesis. Peptide binding to the VEGFR-22 was evaluated using both HUVECS and 293-KDR cells. 1×106 cells were incubated with the biotinylated peptide in 100 µl of 2% FCS in PBS for 2 h at 4° C. Unbound peptides were removed by washing 3 times with PBS and the cells incubated with Alexa Fluor 594-Streptavidine (Molecular Probe) for 1 h. Cells were then washed with PBS three times and fixed with 1% formaldehyde before being analyzed by phase contrast, fluorescence and confocal microscopy.

Proliferation assay. HUVEC ($1 \times 10^4$ cells/well) were plated in 96-well flat-bottom plates overnight. Growth medium was replaced with low sera (1% FCS) medium and the cells were incubated overnight. Media were removed from the wells and replaced with low sera medium containing VEGF mimic peptides at concentrations ranging from 50-50,000 ng/ml with or without rhVEGF (10 ng/ml). When using antibodies as inhibitors, low sera medium containing purified anti-VEGF peptide mimic antibodies at concentrations ranging from 0.15 to 150 µg/ml with or without rhVEGF (10 ng/ml). Plates were incubated for additional 72 h at 37° C. before adding MTT (5 mg/ml) to each well. Plates were incubated 4 h at 37° C., medium was discarded and 100 µl of extraction buffer (20% SDS, 50% dimethylformamide (pH 4.7)) was added to each well. Plates incubated overnight at 37° C. and read on an ELISA plate reader at 570 nm with 655 nm background subtraction. Inhibition percentage was calculated as 100%×(VEGF only treated cells-Peptide treated cells)/(VEGF only treated cells).

Network formation assay using Matrigel. Matrigel (60 µl) (B&D Bioscience) was added to 96 well plate and incubated 30 min at 37° C. HUVEC were kept overnight in low sera medium before cells (20,000/well) were seeded with low sera medium F-12K supplemented with 1% FBS and 10 ng/ml VEGF (R&D System) with or without inhibitor. The cells were fixed in 4% formaldehyde after overnight incubation at 37° C. Pictures from magnification 40× from light microscopy were taken and the sprout points counted using the software imageJ (NIH). Two set of experiments were combined and averaged.

Scratch Wound Assay. HUVEC were cultured on 0.1% gelatin coated 24-well plates. Confluent cells were incubated overnight with starving media, then they were scraped using sterilized 200-µl pipette tips and stimulated with 50 ng/ml of rhVEGF with or without VEGF mimic peptides for 16 h at 37° C. Cells were fixed and images were captured immediately at 40× magnification from light microscopy and cells that migrated to the scraped area were counted using imageJ software.

Phosphorylation assay. HUVEC ($5 \times 10^5$ cells/well) were grown on 6-well plates in FK-12 endothelial cell growth medium supplemented with ECGS and heparin until 80% confluence. After overnight incubation in starving medium (0.5% FBS) cells were treated with inhibitor (100 µM) for 30 min and then stimulated with 10 ng/ml rhVEGF for 5 min. When using KDR-Fc as inhibitor, it was incubated with rhVEGF for 30 min then added to the cells for 5 min. Cells were washed in cold PBS supplemented with 1 mM sodium orthovanadate, harvested into RIPA lysis buffer (Santa Cruz Biotechnology, Santa Cruz, Calif.) and incubated on ice for 30 min. Cell lysate was collected after centrifugation at 13000 rpm for 10 min and kept at −80° C. Total protein (30 µg) from cell lysate was separated in SDS-PAGE and then transferred onto PVDF membrane (Hybond-P, Amersham Pharmacia Biotech). The membrane was blocked in 5% nonfat dried milk in TBST (0.05M Tris Base, 0.9% NaCl, 0.05% Tween 20, pH 7.4) and washed 3 times (10 min.) in TBST before incubation overnight with anti-pY KDR (Santa Cruz Biotechnology, Santa Cruz, Calif.) in 2.5% milk in TBST at 4° C. Membranes were washed in TBST 4 times (15 min), incubated 1 h at room temperature with anti-rabbit IgG (Fab) monoclonal antibody HRP conjugated (Thermo Fisher Scientific Inc, Rockford, Ill.) and washed 6 times (15 min). Proteins on the Western blots were detected using the enhanced chemiluminescent detection system (Thermo Fisher Scientific Inc, Rockford, Ill.). Membranes were stripped and probed for detection of total KDR using anti-KDR HRP conjugated (Santa Cruz Biotechnology, Santa Cruz, Calif.). HUVEC lysates were also used for western blotting following the same procedure but probed for anti-phosphoro p44 and p42 MAP Kinase (Erk1 and Erk2) and re-probed with anti-CD31 for loading control.

293/KDR cells ($5 \times 10^5$ cells/well) were seeded on 6-well plates in DMEM medium supplemented with 10% FBS. After overnight incubation in starving medium (no FBS) cells were stimulated with rhVEGF for 5 min. Cells were washed in cold PBS supplemented with 1 mM sodium orthovanadate and harvested into RIPA lysis buffer (Santa Cruz Biotechnology, Santa Cruz, Calif.) and incubated on ice for 30 min and cell lysate was collected after centrifugation at 13000 rpm for 10 min. Cell lysate was kept at −80° C. until used for Western blotting detecting phosphoro-KDR and total KDR as described above.

Selection and design of VEGF mimic peptides. The strategy to create a conformational peptide consisting of an anti-parallel β-sheet is shown in Table 1 and FIG. 1, 2, where the sequence was modified in a way that the ends were twisted to generate VEGF-P3(NC). It also required two artificial cysteines to be introduced between Gln79 & Gly92, and between Ile80 & Glu93. After synthesis and purification of VEGF-P3 (NC) (non cyclized) peptide, the disulfide bond was formed by oxidation reaction enabling the formation of the twisted anti-parallel β-sheet structure in the VEGF-P3 (CYC) (cyclized).

MS analysis of the peptides. All pure peptides showed uniform peaks on analytical HPLC (purity>95%) and were further characterized using MALDI mass spectros-copy analysis to confirm the calculated and observed (Cal/Obs) molecular weight. In brief; VEGF102-122 (M+H$^+$) Cal/Obs 2482.24/2482.32, VEGF-P3(NC) (M+H$^+$) Cal/Obs 2727.27/2727.61, VEGF-3(CYC) (M+H$^+$) Cal/Obs 2725.27/2725.43, MVF-VEGF-P3(NC) (M+Cal/Obs 5023.67/5023.82, and MVF-VEGF-P3(CYC) (M+Cal/Obs 5021.62/5021.19.

Characterization. CD To verify the secondary structure of VEGF peptide mimics circular dichroism experiments were carried out. CD analyses of VEGF peptide mimics demonstrated a shift in the minimum of the non cyclized peptide (197 nm) spectrum to minima in the cyclic peptide (203, 205 and 210 nm) (data not shown). The shift in the CD spectrum is characteristic of an assumed β-turn II conformational structure, indicating that the cyclic peptide may adopt a configuration more similar of the anti-parallel β-sheet structure present in the loop of VEGF protein. This similarity in the binding region is expected to confer more binding ability to the receptor. We carried out surface plasmon resonance analysis with the purpose of evaluating the binding of VEGF peptide mimics to VEGFR-2.

Figure 3:
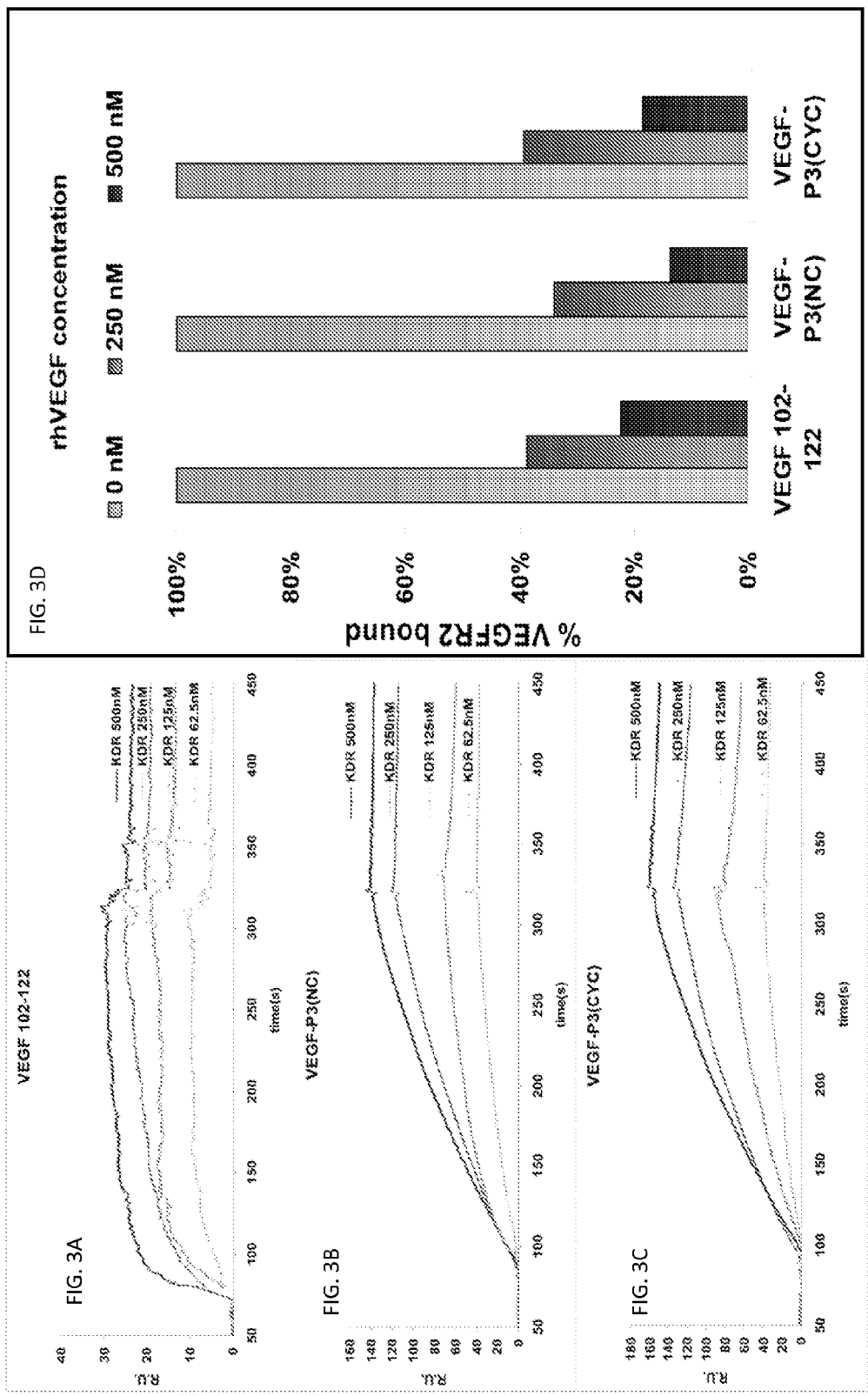
FIG. 3(A-D) show VEGF receptor 2 demonstrated dose dependent binding to the VEGF mimic peptides VEGF 102-122 (FIG. 3A), VEGF-P3(NC) (FIG. 3B) and VEGF-P3(CYC) (FIG. 3C)

Conformational VEGF mimic peptide binds to VEGFR-2. Binding assay was carried out using BIAcore 3000 instrument. Designed VEGF mimic peptide VEGF-P3 (NC) and (CYC) were immobilized onto chip CM5 and the extracellular domain of VEGFR-2(KDR-Fc) was injected as ligand. Sensograms in FIG. 3A-C show that VEGF receptor 2 demonstrated dose dependent binding to the VEGF mimic peptides VEGF-P3(CYC), VEGF-P3(NC) and VEGF 102-122. Global analysis was performed with data points fitting to a simple 1:1 (Langmuir) binding model. The values of association rate constant, Ka, and dissociation rate constant Kd are presented in Table 2. The equilibrium binding constant (KD) takes Ka and Kd values in consideration and represents the binding affinity. As can be seen in Table 2, the binding affinities for VEGF 102-122, VEGF-P3(NC) and VEGF-P3 (CYC) are 45, 49 and 11 nM, respectively. The Ka for all three peptides demonstrated similar values but the Kd for VEGF-P3(CYC) is lower, resulting in a lower KD which represents better affinity. These results confirm that the disulfide bond and cyclization confers a conformational structure in the designed VEGF mimic peptide which allows higher affinity to the receptor. Binding decrease of the extracellular domain of VEGFR-2 to VEGF mimic peptides was observed when rhVEGF was incubated with KDR-fc prior to injection (FIG. 3D), confirming that the extracellular domain of VEGFR-2 binding sites to VEGF mimic peptides and VEGF are located in the same region.

Biotinylated VEGF peptide binds to cells that express VEGFR-2. We evaluated the ability of the VEGF peptide to recognize and bind cells that express VEGFR-2. Biotinylated VEGFR-2 specific peptides as detected by streptavidin Texas red after incubation with peptide-pre-incubated cells but not on the naive ones (FIG. 4A) indicates binding and internalization in HUVEC and in a tumor cell line expressing only this receptor (293-KDR). Most interestingly, the binding of the peptide was seen unevenly distributed over HUVEC (FIGS. 4B & 4D), where the receptors are known to be expressed in clusters and reside in an endosomal population close to the plasma membrane. In the case of the 293-KDR cells, the binding could be seen all over the expressing cells (FIG. 4C) because expression is uniform throughout the cell surface. This explains the increased accumulation in some cells (193-KDR) and the clustering in others (HU-VECS). These results clearly illustrates that the VEGF peptides are specific to the VEGFR-2 and recognize cells that are known to express the receptor, in a pattern which is consistently with its known distribution.

Figure 5:
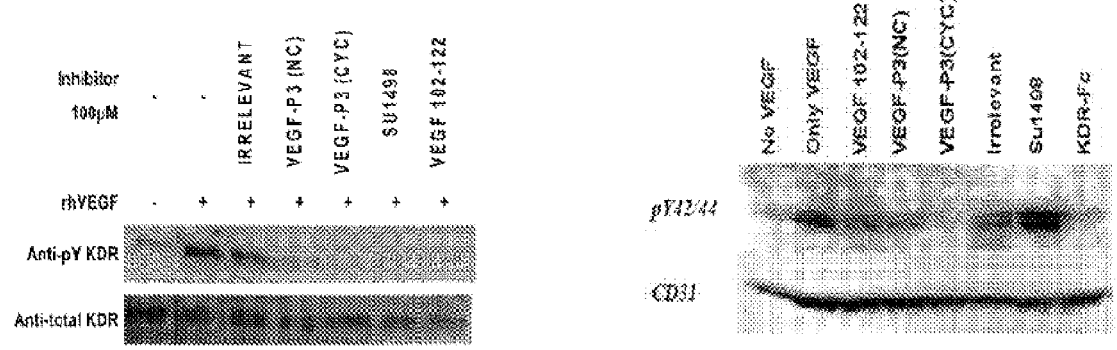
Figure 6:
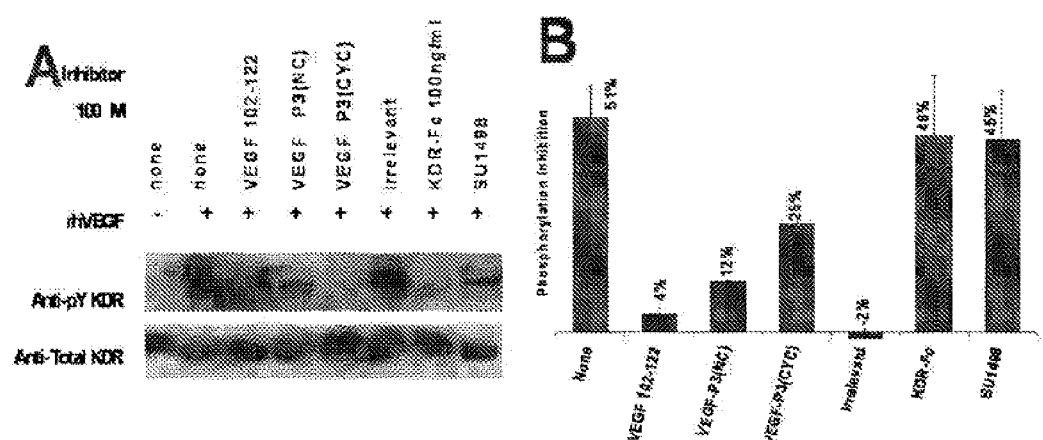

Conformational VEGF mimic peptide prevents VEGFR-2 phosphorylation. VEGFR-2 (also known as flt-1 or KDR) has been characterized as a tyrosine receptor type III. VEGFR-2 activation is promoted by dimerization upon VEGF binding. VEGFR-2 contains several tyrosine residues that can be phosphorylated, triggering several pathways such as proliferation, migration and survival in the endothelial cells. Phosphorylation assay with HUVEC (cells that expresses physiological levels of VEGFR-2) was used to explore the ability of VEGF mimic peptides to block VEGF-VEGFR-2 interaction and consequently phosphorylation. All three VEGF mimic peptides were able to decrease the level of receptor phosphorylation (FIG. 5); however, the inhibitory effect was unable to be quantified, due to the limited detection of VEGFR-2 in the Western blotting. To gauge the effect of VEGF mimic peptides on VEGFR-2 phosphorylation, we used 293/KDR cells, which have been demonstrated to be an excellent model for VEGFR-2 phosphorylation since they over-express VEGFR-2 ($2.5 \times 10^6$ receptors per cell). As seen in FIG. 6A, the degree of VEGFR-2 phosphorylation is notably increased in the presence of exogenous VEGF (10 ng/ml) and decreased when an exogenous receptor (KDR-Fc at 100 ng/ml) was used as a competitor. The level of inhibition in VEGFR-2 phosphorylation was similar with the VEGF natural sequence VEGF 102-122 or irrelevant control. When engineered peptides VEGF-P3(NC and CYC) were used as inhibitors, the level of VEGFR-2 phosphorylation was diminished, with the VEGF-P3(CYC) being the most potent inhibitor. These results were confirmed with the quantification of VEGFR-2 phosphorylation using the Human Phospho-VEGF R2/KDR DuoSet IC kit (FIG. 6B). The highest inhibition was observed with the VEGF-P3(CYC) (25%) followed by VEGF-P3(NC) (12%) while no inhibition was observed with irrelevant peptide (−2%) and a low level of inhibition with the natural sequence peptide VEGF 102-122 (4%). The percentage of inhibition was calculated assuming the phosphorylation level of control (only rhVEGF) was 100% and the results are represented in FIG. 6B.

Activation of VEGFR-2 also triggers the MAPK (mitogen-activated protein kinase) pathway as one of the downstream signaling in the endothelial cells. The level of phosphorylation of MAPK p44$^{ERK1}$ and p42$^{ERK2}$ was observed using western blotting and antibodies against phos-phoro-p44/42 (FIG. 5B). Decrease of phosphorylation level was greater when the VEGF-P3(CYC) was used as inhibitor followed by the non-cyclic peptide VEGF-P3(NC) and VEGF 102-122. The small tyrosine kinase SU1498, used as one of positive controls, has been shown to accumulate phosphorylated MAP kinases in endothelial cells because it interacts with other kinases such as ERK 1/2, affecting other pathways. Tyrosine kinase inhibitors usually act by binding the kinase active site blocking ATP binding; consequently the phosphate is not transferred to the tyrosine residue. This mechanism of action has two major drawbacks as tyrosine kinase inhibitors: low specificity and high susceptibility to resistance (enzymes often mutate themselves to recover activity. VEGF peptide mimics demonstrated the same pattern of inhibition in VEGFR-2 and MAPK phosphorylation, indicating that downstream MAPK signaling of VEGFR-2 is being inhibited by decreased VEGFR-2 activation. Next we evaluated whether inhibition of VEGFR-2 cascade signaling would be translated in inhibition of activation of endothelial cell network formation, migration and proliferation. In order to determine these effects we tested VEGF peptide mimics in several in vitro angiogenesis assays.

Figure 7:
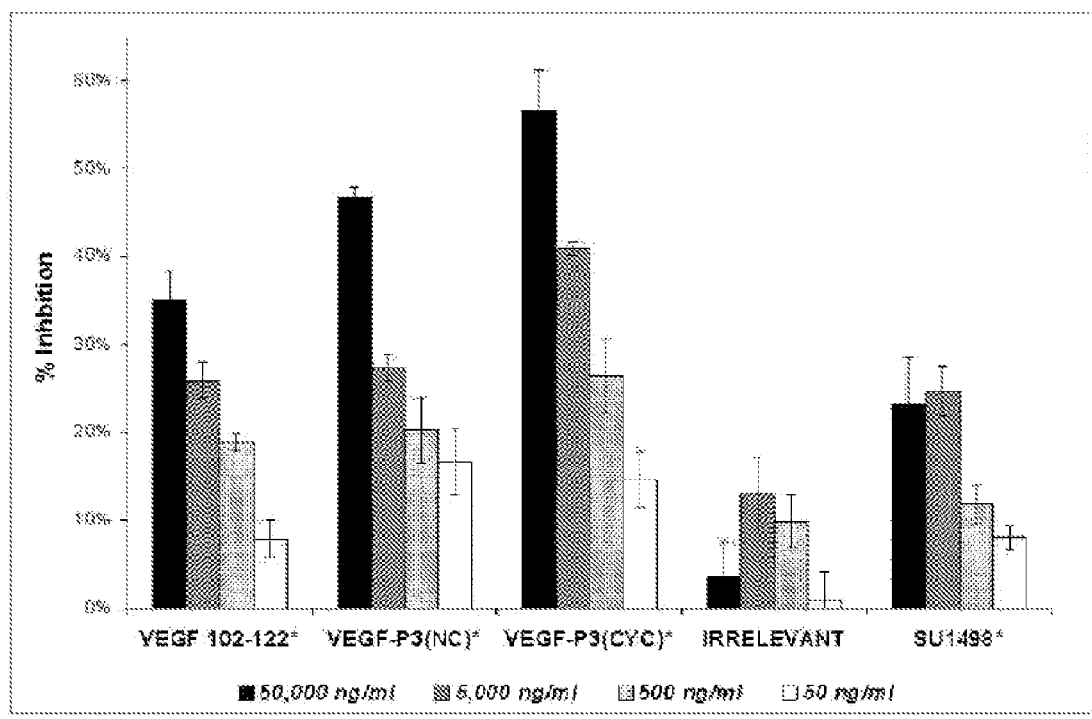

Conformational peptide inhibits HUVEC proliferation. Endothelial cell proliferation is VEGF dependent, and mostly activated by VEGFR-2 activation. Thus, angiogenesis inhibitors should inhibit HUVEC proliferation. This assay was carried out in the presence of several concentrations of VEGF mimic peptide to verify their ability to inhibit VEGF dependent proliferation. FIG. 7 shows that all VEGF mimics can inhibit HUVEC proliferation in a dose dependent way and that the conformational peptide VEGF-P3 (CYC) demonstrated the highest inhibitory effect. The toxicity of the VEGF mimic peptides was verified using HUVEC proliferation assay in the absence of VEGF where no significant differences between peptide treated and untreated cells were observed (data not shown).

Figure 8:
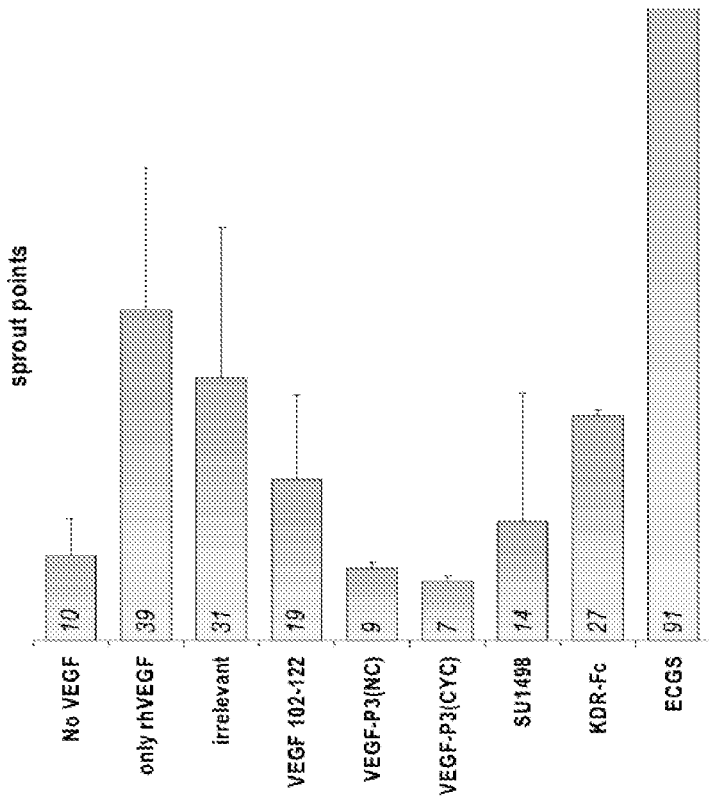
Figure 8:
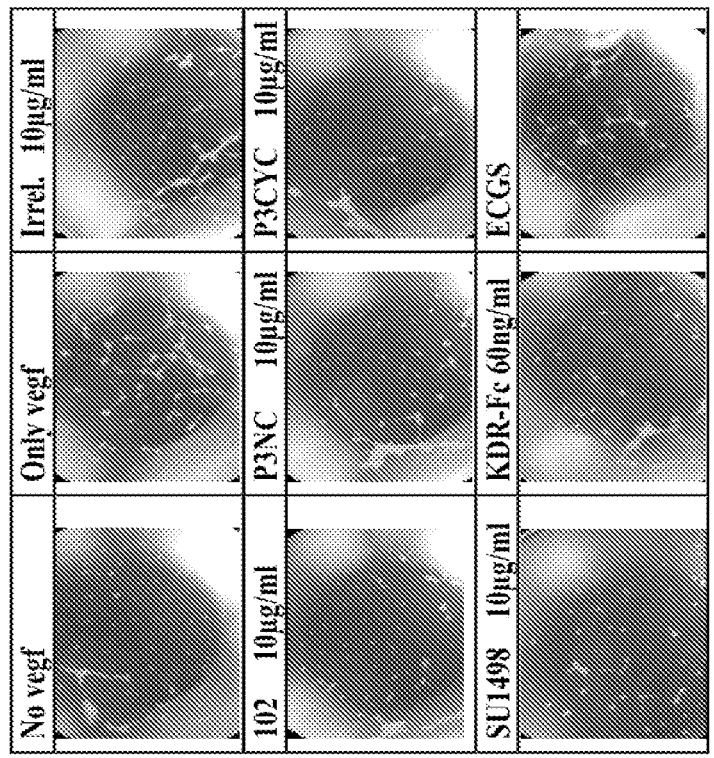

Conformational peptide decreases HUVEC network formation in Matrigel assay. Activation of VEGFR-2 also triggers the MAP Kinase pathway that leads to the formation of cell cords and tubes by the endothelial cells. In vitro Matrigel assay is an appropriated model for assessing network formation once it takes advantage of the capacity of cell cord formation by HUVEC growing in an extracellular matrix (Matrigel). Network formation is clearly VEGF dependent as can be seen in FIG. 8A, where a cell network with several sprout points is more evident in the VEGF treated HUVEC than the non-VEGF treated HUVEC. Decrease in the network branching and tube formation was observed in VEGF treated HUVEC in the presence of VEGF mimic peptides and no significant effect was seen with the irrelevant control (FIG. 8B). The best inhibitory effect was demonstrated by engineered mimic peptides VEGF-P3 (NC and CYC). These results are in agreement with VEGFR-2 phosphorylation and HUVEC proliferation assay, indicating that VEGF mimic peptides can block VEGF and VEGFR-2 interaction.

VEGF mimic peptides inhibit cell migration in a Scratch Wound Assay. New blood vessel formation requires that the endothelial cells migrate towards the sources of growth factor. This process has similar characteristics with wound healing in which VEGF has been shown to play an important role throughout VEGFR-2 activation. We used the scratch wound assay with HUVEC to observe the ability of the VEGF mimic peptides in inhibiting endothelial cell migration. As can be seen in FIG. 9A, cells were able to migrate towards the scratched area in higher number when exogenous rhVEGF was added compared to the absence VEGF. Growth conditions (medium supplemented with 20% FBS and endothelial cell growth supplements). (FIG. 6), shows a slight increase in percentage of migrated cells, probably due to the complexity provided by the supplements. Irrelevant peptide control had a comparable number of migrated cells when compared to rhVEGF control, indicating no inhibition. All three VEGF mimic peptides demonstrated ability of inhibiting HUVEC migration at similar levels (approximately 50%) of the small VEGFR-2 tyrosine kinase inhibitor (SU1498) at a standard concentration (FIG. 9B), indicating that VEGF mimic peptides are capable of blocking the VEGF dependent migration in endothelial cells.

Figure 10:
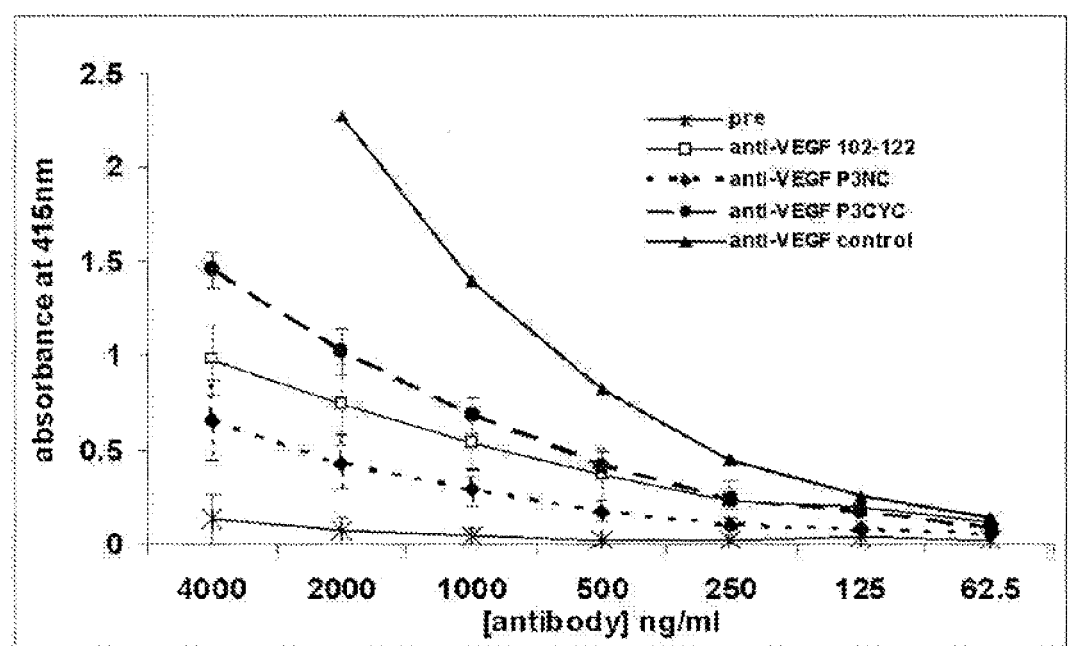
Figure 11:
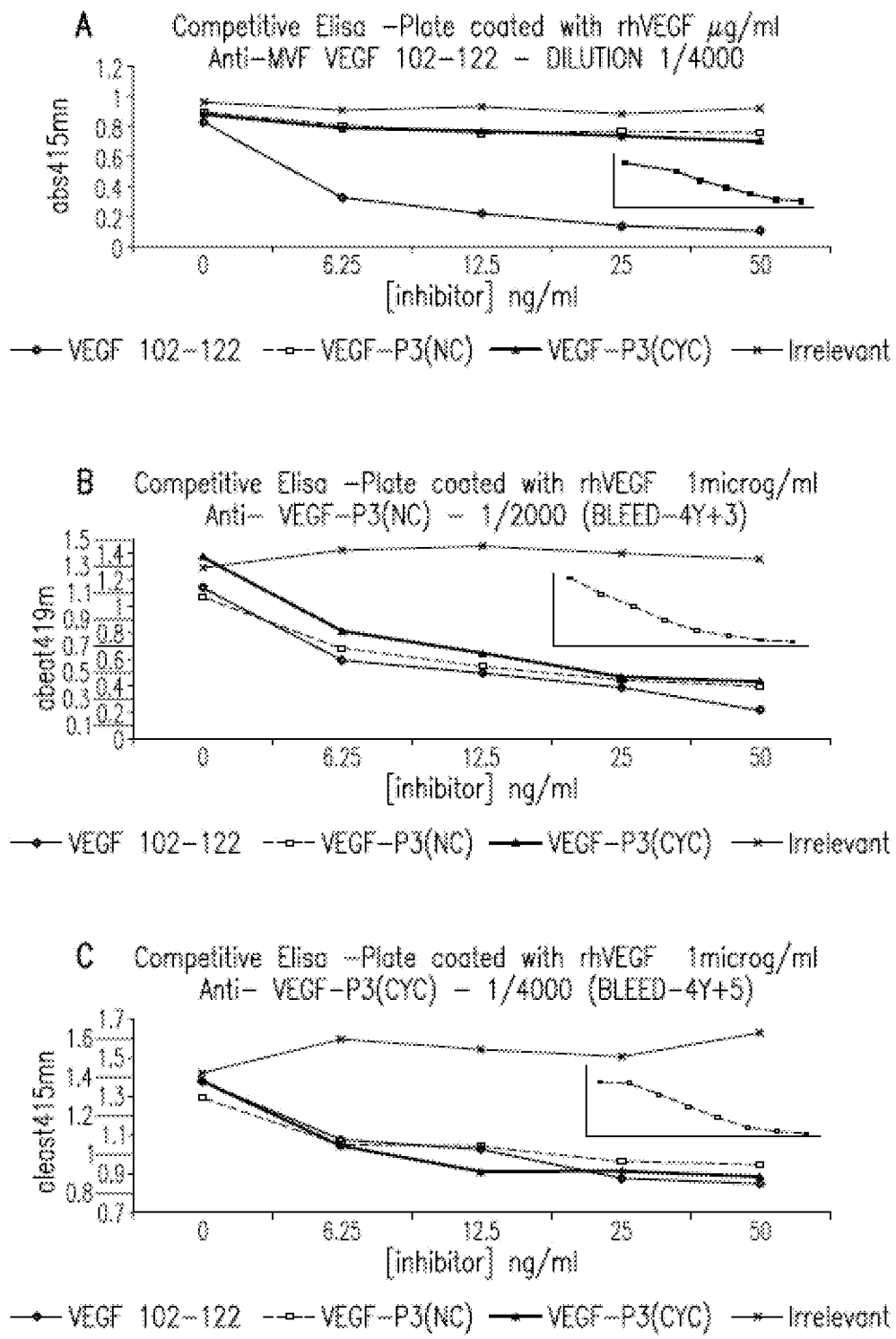

Antibodies raised against VEGF mimic peptides recognize rhVEGF. Epitope-based peptides have been widely used to generate antibodies with better affinity and specificity. Previously we successfully predicted conformational epitopes and developed conformational peptides for cancer vaccine approach. Here we explored the ability of VEGF mimic peptides to generate antibodies that will recognize the whole protein. VEGF sequence 102-122 (76-96) comprises the region containing some residues important for antibody neutralization of VEGF and we predicted that anti-peptides generated against our engineered peptides VEGF-P3(NC and CYC) would retain or enhance the specificity for VEGF protein. A promiscuous T cell epitope MVF 288-302, which has been demonstrated to enhance immune response, was incorporated into VEGF mimic peptides and used for raising antibodies in rabbits. All three constructions of VEGF mimic peptides demonstrated high immunogenicity (data not show) and were able to recognize the entire protein when the rhVEGF was used as an antigen in an ELISA assay (FIG. 10) as well as in the resonance plasma surface analysis (Table 3). Rabbit pre-immune sera (FIG. 10) and anti-peptide raised against an unrelated peptide sequence were unable to recognize rhVEGF in the same assay (data not shown). To confirm their specificity to the immunogen VEGF, we carried out competitive ELISA assay using rhVEGF as antigen and VEGF mimic peptides as competitors. FIG. 11 shows the Competitive ELISA results for anti-MVF-VEGF 102-122 (FIG. 11A), anti-MVF-VEGF-P3(NC) (FIG. 11B) and anti-MVF-VEGF-P3(CYC) (FIG. 11C). VEGF 102-122 peptide was able to compete only for the binding site in the anti-VEGF 102-122. Both engineered VEGF-P3 peptides, in the linear and cyclic form, were able to compete for the binding site in the anti-VEGF-P3(NC and CYC) but not to the antibodies generated against the natural sequence. This indicates that the engineered peptides did not generate antibodies against the linear sequence of VEGF but most importantly that they reassemble the conformational epitope in the VEGF protein. Kinetic parameters of antibodies raised against VEGF mimic peptides were obtained by surface plasma resonance using direct binding assay in BIAcore 3000. Anti-peptide antibodies were injected as ligands over rhVEGF immobilized onto CM5 chip. The binding affinity to the whole protein was higher for the antibody raised against the conformational epitope, anti-VEGF-P3(CYC) (KD=146 nM), followed by the anti-VEGF-P3(NC) (KD=251 nM) and the antibody raised against the natural sequence anti-VEGF 102-122 (KD=552 nM). As can be seen in Table 3, the Ka for the anti-VEGF mimic peptides demonstrated only 10 fold decrease in association rate constant, Ka and comparable dissociation constant rate Kd when compared to a commercially available monoclonal antibody against VEGF.

Figure 12:
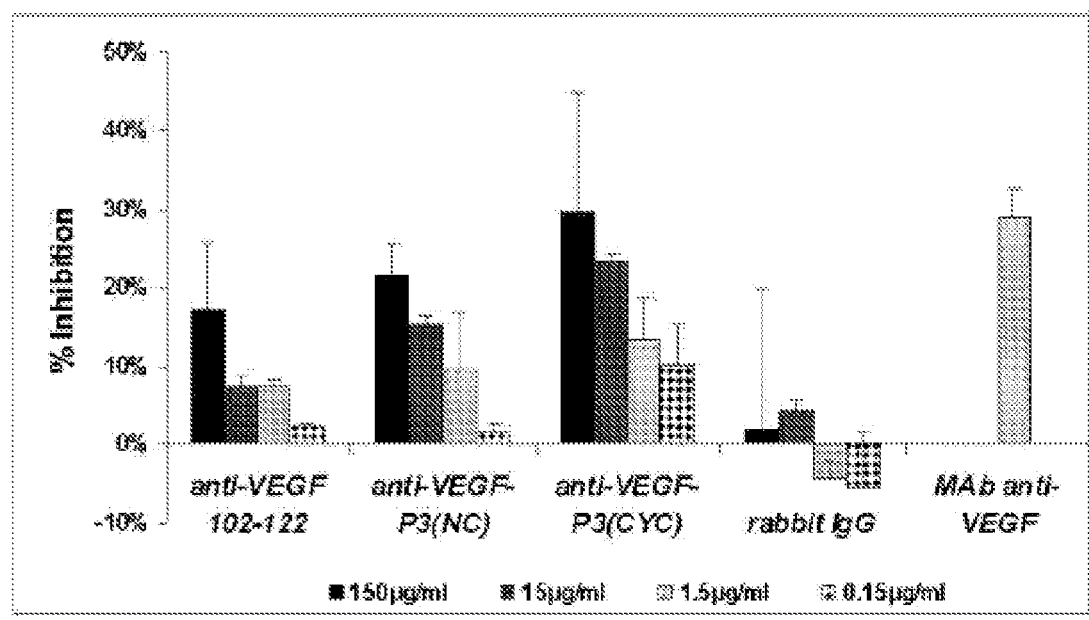

Anti-VEGF peptide antibodies used as inhibitors of HUVEC proliferation. VEGF neutralizing antibodies blocks the interaction of VEGF and VEGF receptors by binding to and occluding VEGF binding sites. Since our anti-VEGF mimic peptide antibodies were able to bind VEGF, we tested their ability of inhibiting VEGF dependent HUVEC proliferation assay. All three anti-VEGF peptide antibodies were able to inhibit HUVEC proliferation in a dose dependent way when compared to the pre-immune-serum control. Anti-VEGF-P3(CYC) demonstrated the highest inhibition and anti-VEGF-P3(NC) seems to be slightly more efficient than the natural sequence (FIG. 12). In this model the proliferation inhibition is believed to be due to blockage of interaction between VEGF and VEGFR-2, indicating that the engineered VEGF-P3(CYC) which contains twisted ends and the disulfide bond to mimic the binding region of VEGF can generate antibodies against the conformational epitope which resulted in the highest neutralization effects.

Protein-protein interactions trigger a wide variety of cellular pathways, representing a target for drug development. The active or passive binding sites of a protein are confined to a small set of amino acids; therefore smaller sequence like peptides can be designed to simulate these regions, potentially acting as an agonist or antagonist. Synthesis of peptides is easier and cheaper than proteins and recent approaches have brought many new improvements to the delivery and stability of peptide in vivo. Peptides which mimic the VEGFR-2 binding site of VEGF were designed to block VEGF:VEGFR-2 interaction, which has been characterized as the most important for angiogenesis activation.

Figure 2:
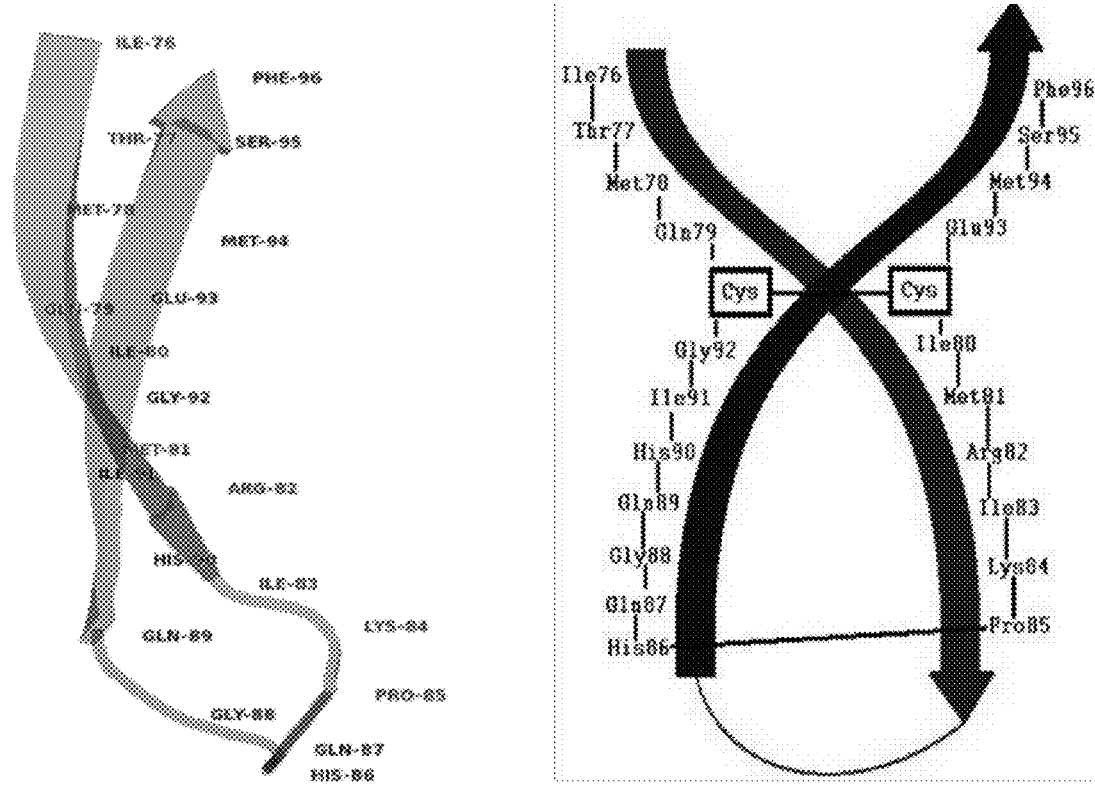
FIG. 2 shows a conformational peptide consisting of an anti-parallel β-sheet.

Here we report that peptides corresponding to the natural VEGF amino acid sequence 102-122 (76-96) (FIG. 1) which comprises the loop region with the important binding residues of VEGF to its receptor was successfully synthesized. In an attempt to better mimic the conformational structure of this sequence in the protein VEGF-P3(NC) and (CYC) were synthesized, in which the ends were twisted and cysteines were inserted to enable cyclization (FIG. 2). CD analysis confirmed that the VEGF-P3(CYC) assumes more characteristics of β-turn II and, surface plasmon resonance analysis demonstrate that VEGFR-2 had a higher binding affinity for this cyclic peptide than to the non-cyclized version (VEGF-P3(CYC)) and the natural sequence (VEGF 102-122), indicating the importance of the constrained structure for the binding of the peptide. Competition assay showed that VEGF peptide mimics and VEGF are binding to VEGFR-2 in the same region, indicating the peptide mimics could act as antagonist to VEGF. The conformational peptide VEGF-P3(CYC) also demonstrated to be the best competitor in the BIAcore experiments indicating that the designed peptide would interfere more with the VEGF-VEGFR-2 interaction. Antibodies raised in rabbits against VEGF mimic peptides showed to be specific for each peptide and also recognize the native protein rhVEGF. Anti-VEGF-MVF-P3 (CYC) demonstrated better affinity for rhVEGF in SPR experiments, indicating that the conformational peptide construction is mimicking better the portion comprising the loop in VEGF.

Several in vitro assays have been established to explore VEGF-depend angiogenesis and we carried out them to test whether the antagonist effect of VEGF peptide mimics could block VEGF action in these assays. Upon VEGF binding, VEGFR-2 dimerizes leading to phosphorylation of tyrosines in the kinase domain which triggers several pathways including endothelial cell proliferation, migration and survival. The inhibitory effects of VEGF peptide mimics on VEGFR-2 phosphorylation were evaluated indicating that they were able to inhibit VEGFR-2 phosphorylation in a cell line (HUVEC) physiologically expressing VEGFR-2, as well as in the over-expressing cell line (293/KDR). We also observed a decrease in p44/42 MAPK phosphorylation which is one of the downstream signaling resulting from VEGFR-2 activation. The designed peptide VEGF-P3 (CYC) displayed the best inhibitory effect on phosphorylation assay following the pattern observed with surface plasmon resonance (SPR) experiment, indicating that the design to better mimic conformational structure of VEGF binding site confers better inhibitory effects on VEGF activated signaling. The biotinylated VEGF-P3-CYC peptide was also shown to specifically bind to cells that have different expression of the VEGFR-2 and the pattern of binding was coherent with the receptor expression.

To confirm the effect of the VEGF peptide mimics as angiogenesis inhibitors we used several in vitro angiogenic assays which such as scratch wound (migration), Matrigel (network formation) and HUVEC proliferation assay (proliferation). All three VEGF peptide mimics were able to inhibit cell migration in the presence of exogenous rhVEGF at the wound assay, showing that they can block migration induced by rhVEGF, throughout blocking VEGF:VEGFR-2 interaction. When testing whether the VEGF peptide mimics could inhibit the network formation in Matrigel which is a VEGF dependent process, all three peptide mimics were able to inhibit this with VEGF-P3(CYC) displaying the largest inhibition. Proliferation of endothelial cells is essential to formation of the new wall vessels and inhibition of HUVEC proliferation was observed in a dose dependent manner with VEGF-P3(CYC) as the most potent inhibitor. The conformational peptide VEGF-P3(CYC) demonstrated the best inhibitory effects, the highest binding affinity, and is most likely due to the loop stabilization by the disulfide bond between the extra cysteines. Our biochemical and in vitro experiment results were in agreement and established that VEGF-P3 (CYC) had the best potential of inhibiting angiogenesis.

Peptides can be used as antigen to generate high affinity antibodies specific for an entire protein. These peptides must include the antigenic determinant residues which usually are hydrophilic and are exposed in the protein. These can be achieved by rational design of peptides that may include few modifications in order to obtain similar conformational structure of the protein. Our primary goal was to evaluate VEGF peptide mimic as angiogenesis inhibitors. However, the VEGF peptide mimic was designed to mimic the binding region of VEGF to VGFR-2 which overlap with a B-cell predicted epitope. We also tested if synthetic VEGF peptide mimics could be used to generated antibodies against native VEGF protein. Since combining the B-cell and the T-cell epitope have allowed us to increase the immunogenicity of peptides, we linked VEGF peptides to a promiscuous T-cell epitope from MVF. These peptides were highly immunogenic in outbred rabbits and purified antibodies against all three VEGF peptide mimics recognized rhVEGF. We quantified the binding affinity of these antibodies by using the SPR experiments. Among anti-VEGF peptide mimics antibodies, anti-MVF-VEGF-P3(CYC) has the highest binding affinity, suggesting that the structural arrangement of VEGF-P3 (CYC) were able to generate antibody that can bind tighter to the VEGF. Competitive ELISA results showed that the epitope recognized in VEGF by anti-VEGF peptide mimics are not the same, indicating that the anti-MVF-VEGF-P3 (NC) and (CYC) bind to VEGF by recognition of conformational instead of the linear epitopes.

VEGF neutralizing monoclonal antibodies, such as Avastin, binds to VEGF preventing VEGF-VEGFR-2 interaction and as consequence inhibits angiogenesis. Anti-peptide generated against VEGF peptide mimics were able to specifically recognize the native protein and anti-MVF-VEGF-P3

(CYC) demonstrated better affinity to rhVEGF. We further evaluated if these anti-peptide antibodies would block VEGF-VEGFR-2 interaction and as expected, the inhibitory effect on HUVEC proliferation of anti-MVF-VEGF-P3 (CYC) was slightly better than the other anti-VEGF peptide mimic antibodies.

The design of the peptide, VEGF-P3(CYC) that would mimic a structural binding site of VEGF to its receptor was shown to be important in obtaining a better inhibitory molecule in several in vitro assays. These findings motivate the development and potential of using VEGF-P3(CYC) as an alternative of peptide therapeutic drug to inhibit angiogenesis. Still, future analysis involving animal models of angiogenesis-dependent tumor formation will give insight into the efficacy of these peptides in inhibiting angiogenesis given the complexity of the tumor microenvironment. In the tumor vicinity stromal cells are involved in angiogenesis and they also can activated other processes like neovascularization in which endothelial progenitor cells (EPC) can initiate the formation of completely new blood vessels.

It also will be interesting to observe whether this peptide would have an effect on other important aspects of VEGF signaling via VEGFR-1 in other cells like macrophage or EPC. VEGF-P3(CYC) is not expected to interact with VEGFR-1 once it does not include the VEGF residues responsible for binding to VEGFR-1. However, VEGF-P3 (CYC) may interfere with signaling activated by the heterodimer VEGFR-1NEGFR-2 which can also activate angiogenesis. VEGF-P3(CYC) may also be relevant in inhibiting autocrine activation in cancer cells once cells lines derived from breast cancer had been shown to overexpress VEGFR-2 that can be activated in an autocrine loop via upregulation of VEGF.

In conclusion, we showed that VEGF receptor-specific peptides can interfere with the interaction between VEGF and VEGFR-2 inhibiting several VEGF dependent pathways and indicating that VEGF mimic peptide have the a clear potential as candidate in preclinical studies using animal models as alternatives to the development of new anti-angiogenesis therapeutic approaches.

Combination treatment with HER-2 and VEGF peptide mimics induces potent anti-tumor and anti angiogenic responses in vitro and in vivo.

HER-2 is a member of the EGFR family and is overexpressed in 20-30% of breast cancers. HER-2 overexpression causes increased expression of VEGF at both the RNA and protein level. These two proteins HER-2 and VEGF are therefore considered good targets for cancer treatment which has led to the development of two humanized monoclonal antibodies (mAb) Pertuzumab and Bevacizumab that target HER-2 and VEGF respectively. Exposure of HER-2 overexpressing cells to trastuzumab/herceptin another mAb that targets HER-2 significantly decreases VEGF expression. Although passive immunotherapy with these Abs has been approved for treatment of advanced breast cancer, a number of concerns exist with passive immunotherapy. Treatment is expensive, and has a limited duration of action, necessitating repeated administrations of the mAb. Peptide therapy with conformational B-cell epitope mimics can be cheaper with a longer half-life with greater penetrating abilities. The goal of the present study was to show that combination treatment with HER-2 and VEGF peptide mimics provides greater efficacy than single treatment. We designed and synthesized peptides based on the binding of (i) HER-2 with Pertuzumab and (ii) VEGF with VEGFR-2. We show that combination treatment with these peptides induces potent anti-tumor and anti-angiogenic responses in vitro and in vivo. The major drawback with peptides is the fact that they are easily degraded by proteases in vivo. To address this problem, we synthesized the retro-inverso peptide using D-amino acids which cannot be degraded by proteases. We have also shown that combination treatment with the D-amino acid peptide is more potent than the L-amino acid counterpart.

In this study, we report on the activity of the HER-2-266-296 peptide mimic in combination with two VEGF peptide mimics that were synthesized using L and D amino acids. The VEGF peptides were shown to mimic the binding site of VEGF to its receptor VEGFR-2. Combination treatments with both peptides were able to caused superior anti-tumor and anti-angiogenic effects in vitro and in vivo. This was clearly demonstrated by increased in proliferation and phosphorylation inhibition and a decrease in cell viability. Combination treatment also caused a greater delay in tumor growth and development in a transplantable tumor model. These results demonstrates that B-cell epitope peptides can have great therapeutic effects and targeting both HER-2 and VEGF will produces potent anti-tumor and anti-angiogenic effects.

Synthesis and characterization of conformational peptides. Peptide synthesis was performed on a Milligen/Biosearch 9600 peptide solid phase synthesizer (Bedford, Mass.) using Fmoc/t-But chemistry. Preloaded Fmoc-Val-CLEAR ACID resin (0.35 mmol/g) for the 266-296 and CLEAR AMIDE RESIN for the VEGF peptides (0.32 mmol/gm) (Peptides International, Louisville, Ky.) were used for synthesis. The 266-296 cyclized epitope was assembled by choosing the regioselective side chain protector Trt on Cys residues 268 and 295 (20), and in the VEGF peptides two cysteines were inserted between amino acid Gln79 and Gly92 and between Ile80 and Glu93. Peptides were cleaved from the resin using cleavage reagent B (trifluoroacetic acid:phenol:water:TIS, 90:4:4:2), and crude peptides purified by semi preparative reversed-phase-HPLC and characterized by electrospray ionization mass spectroscopy. Intramolecular disulphide bonds were formed using iodine oxidation as described and disulphide bridge formation was further confirmed by maleimide-$PEO_2$-biotin reaction and subsequent analysis using electrospray ionization mass spectroscopy.

Circular Dichroism was done as previously described.

Animals. Female BALB/c mice were purchased from the Jackson Laboratory (Bar Harbor, Me.). Animal care and use was in accordance with institutional guidelines.

Cell lines and Antibodies. All culture media, FBS, and supplements were purchased from Invitrogen Life Technologies (San Diego, Calif.). The human breast tumor cell lines BT-474, SK-BR-3, and MDA-468 were purchased from American Type Culture Collection (Rockville, Md.) and maintained according to supplier's guidelines. TUBO cells were a cloned cell line established in vitro from a lobular carcinoma that arose spontaneously in BALB-neuT mouse. Humanized mouse mAb Trastuzumab was generously provided by Genentech, Inc. (South San Francisco, Calif.).

Peptide treatment in transplantable mouse model. Balb/c mice (n=5) 5 to 6 weeks of age were challenged subcutaneously with $1 \times 10^5$ TUBO cells and after challenge, mice were treated intravenously with 100 μg of either HER-2 or VEGF peptide mimics or a combination of both as inhibitors. Mice were euthanized at week 10 and tumors removed. Tumors were measured for tumor volume twice a week using calipers and calculated using the formula (length× width)/2.

Statistical analysis. Tumor growth over time was analyzed using Stata's XTGEE (cross-sectional generalized estimating equations) model which fits general linear models that allow you to specify within animal correlation structure in data involving repeated measurements. For other experiments t-test was carried out to observe the statistical relevancy in between different sets of experiments as well as the significant difference between treated and non treated cells.

Proliferation assay. BT-474, SK-BR-3, MDA-468 and TS/A cells (1×10$^4$ were plated in 96-well flat-bottom plates overnight. Growth medium was replaced with low sera (1% FCS) medium and the cells were incubated overnight. Media were removed from the wells and replaced with low sera medium containing HER-2 and VEGF mimic peptides at concentrations ranging from 25-150 ug/ml and plates were incubated an additional 1 h at 37° C. before adding 10 ng/ml HRG in 1% medium. Plates were incubated for an additional 72 h at 37° C. before adding MTT (5 mg/ml) to each well. Plates were incubated 2 h at 37° C., and 1000 of extraction buffer (20% SDS, 50% dimethylformamide (pH 4.7)) was added to each well. Plates incubated overnight at 37° C. and read on an ELISA reader at 570 nm with 655 nm background subtraction Inhibition percentage was calculated as 100%× (Untreated cells-Peptide treated cells)/(Untreated cells).

Phosphorylation assay. 1×10$^6$ BT-474 cells were plated in each well of a six well plate and incubated overnight at 37° C. Culture medium was removed and the cell layer washed once with PBS low score (1% FCS). Culture medium was added to the wells and plates incubated overnight. Cells were washed and 50 ug of peptides, anti-peptide Abs and controls in binding buffer (0.2% w/v BSA, RPMI 1640 medium with 10 mM HEPES (pH 7.2) was added to the wells and incubated at room temperature for 1 h. HRG (5 nM/well) was added and the incubation continued for 10 min. Binding buffer was removed and the cell layer washed once with PBS before adding 1 ml of RIPA lysis buffer (Santa Cruz Biotechnology, Santa Cruz, Calif.). Plates were rocked at 4° C. for 2 h. Lysates were removed, spun at 13000×g and supernatants collected. Protein concentration of each sample was measured by Coomassie plus protein assay reagent kit and lysates were stored at −80° C. Phosphorylation was determined by Duoset IC for human phosphor-ErbB2 according to the manufacturer's directions (RSD Systems).

Viability assay. This assay was performed just like the proliferation assay but after treatment with the peptide inhibitors, the aCella-TOX reagent was used to estimate the amount of dead cells. After peptide treatment for 72 h, the plate was removed and equilibrated to room for 15 mins before adding 10 µl of lytic agent to the control wells for maximum lysis and incubated for 15 min at room temperature. 100 µl of the Enzyme Assay reagent containing G3P was then added to all wells followed by 50 µl of the detection reagent. The plate was immediately read using a luminometer.

Selection, design and characterization of peptides. The crystal structure of the complex between VEGF and the Fab fragment of a humanized antibody, and analysis of the contact residues on both sides of the interface was published by Muller et al. Zilberberg et al. also identified that the sequence 79-93 of VEGF is involved in the interaction with VEGF receptor-2. Although the VEGF residues critical for antibody binding are distinct from those important for high-affinity receptor binding, they occupy a common region on VEGF demonstrating that the neutralizing effect of antibody binding results from steric blocking of VEGF-receptor interactions and only a small number of the residues buried in the VEGF-Fab interface are critical for high-affinity binding and are concentrated in one continuous segment of polypeptide loop between β5-β6. Several residues are important for VEGF receptor binding, including Met 81, Ile 83, Lys 84, Pro85, Gln 89, and Gly92. We have selected to use a peptide encompassing residues 102-122 (numbered as 76-96 in the crystal structure) which mimics the overlapping VEGF binding sites to VEGFR-F2 and Avastin. The strategy to create a conformational peptide consisting of an anti-parallel β-sheet is shown in Table 4, where the sequence was modified in a way that the ends were twisted to generate VEGF-P3(NC). It also required two artificial cysteines to be introduced between Gln79 & Gly92, and between Ile80 & Glu 93. After synthesis and purification of VEGF-P3 (NC) (non-cyclized peptide, the disulfide bond was formed by oxidation reaction enabling the formation of the twisted anti-parallel β-sheet structure in the VEGF-PE (CYC) (cyclized). The retro-inverso (RI) peptide analog VEGF-RI-P4 was synthesized using D-amino acids with the amino acid sequence in reverse order, such that the resulting peptide mimic has a reversal of the peptide backbone but a topochemical equivalence to the parent peptide in terms of side-chain orientation. The rationale behind the retro-inverso peptidomimetic is that it should present similar activity with the advantage of higher bioavailability.

HER-2-266-296 peptide (Table 4) was synthesized based on the crystal structure of the Fab of pertuzumab bound to the ECD of HER-2/neu. This reveals that pertuzumab binds to subdomain II of the HER-2 ECD. The 266-333 region of HER-2 was selected for the design of the peptides with the objective of eliciting abs against the peptide capable of inhibiting dimerization of HER-2 with other members of the EGFR family. The peptide can also be used to directly block dimerization due to its ability to bind and recognize the HER-2 ECD.

Figure 13E:
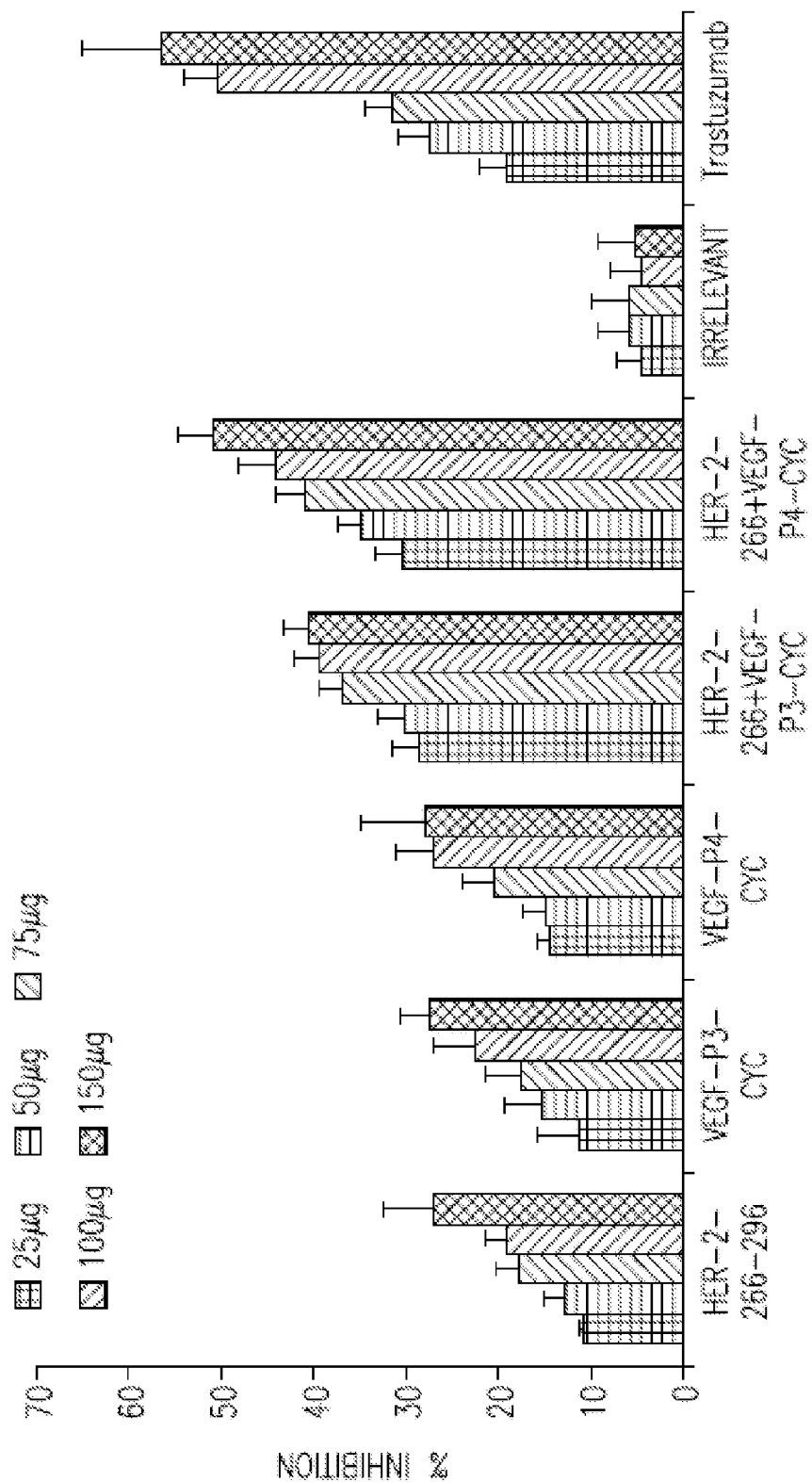

Antiproliferative effects of peptides. The antiproliferative effects of the peptides were tested using four different cell lines (Bt-474 and SK-BR-3: HER-2$^{high}$, MDA-468: HER-2$^{low}$ and TS/A: HER-2$^{negative}$) (FIGS. 13A-13D) in the presence of HRG to activate the HER-3 receptor. Unlike trastuzumab that is specific to HER-2 positive cells, pertuzumab is known to act on cells by disrupting ligand dependent receptor complexes independent of HER-2/neu expression. The cells were incubated with the peptides before being exposed to HRG. We found that both the HER-2 and VEGF peptides were able to inhibit tumor growth and the effect was concentration dependent (FIGS. 13A-13D). We used four different cell lines to show that the effects of the peptide was dependent on HER-2 expression since higher inhibition was observed in cases of high HER-2 expression. BT-474 and SK-BR-3 both have high HER-2 expression but the level of HER-1 and HER-3 (HER-2 dimerization partners) in SK-BR-3 are respectively ten times and two times higher than in BT-474. This probably explains why the % inhibition is by far greater in SK-BR-3 cells than in BT-474 cells (FIGS. 13A and 13B). The HER-2-266-296 also showed inhibitory effects on HER-2 negative cells (TS/A cells which originated from a mammary adenocarcinoma that arose spontaneously in a BALB/c female retired breeder. This is because the peptide was designed based on the binding of HER-2 to pertuzumab which has been shown to inhibit HER-2 negative cells (36). We also tested the effects of combination treatment with both HER-2 and VEGF peptide mimics and we observed an increase in rate of inhibition when both peptides were used as compared to single treatments (FIG. 13E). Statistical analysis showed a significant difference between the treated and untreated cells in all five concentrations (25, 50, 75, 100 and 150 µg) with P* values of <0.001 using the 95% confidence intervals.

Irrelevant peptide did not show antiproliferative effects while Trastuzumab (positive control) showed antiproliferative effects only on cells that express the HER-2 receptor (FIGS. 13A & 13E).

Figure 14A:
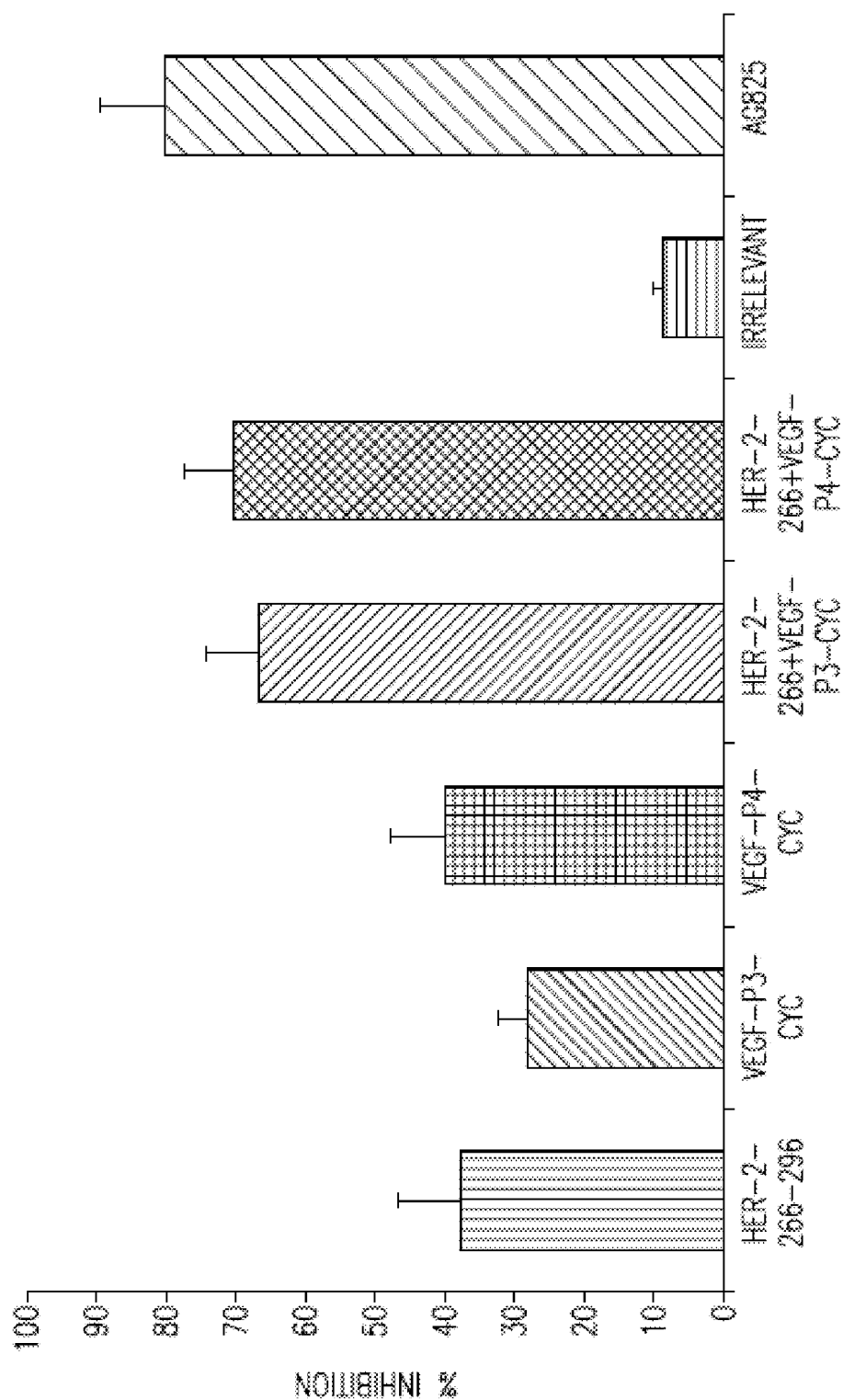

Effects of peptide treatment on breast cancer cell viability. We next evaluated the effects of combination treatment on tumor cell survival in vitro. The MTT proliferation assay simply shows that the peptides are able to prevent the cells from growing but does not tell if the cells are being killed by the peptide. This was tested using the acella-TOX reagent kit where dead or dying cells released the enzyme GAPDH and measuring the activity of this enzyme will give an estimate of the cell viability after treatment. The results showed that the peptide treatment was able to cause a decrease in cell viability and combination treatment caused a further decrease in viability of at least 40% compared to single treatment (FIG. 14A). There was a statistically significant difference between treatment with HER-2 or VEGF peptides and the untreated group with P* values<0.05 using the 95% confidence interval. The difference was most significant in the case of the combination treatment with both HER-2 and VEGF peptide mimics with P* values<0.001 when using the 95% confidence interval when compared to the untreated. Finally, when comparing the single and combination treatment, we also obtained a significant difference with P** values<0.001 using the same confidence interval. Treatment with Irrelevant peptide showed no statistical difference with untreated cells.

Peptide inhibition of Phosphorylation. The main mode of action of Pertuzumab is to inhibit phosphorylation. This is due to the fact that it sterically blocks the dimerization domain of HER-2 thereby preventing the formation of dimers with other HER receptors and thus interrupting downstream signaling. We have showed that the peptides were able to prevent phosphorylation of the HER-2 protein and single treatment with the HER-2 peptide alone caused a 38% inhibition rate while the VEGF peptide with L and D amino acids caused an inhibition rate of 28% and 39%, respectively (FIG. 14B). Combination treatments led to dramatic increases in rate of inhibition of 67% and 70% for combining HER-2+VEGF-P3-CYC and HER-2+VEGF P4-CYC respectively (FIG. 14B). All peptide treatments were compared to the positive control AG825 (Calbiochem), a HER-2 specific phosphorylation inhibitor. Statistical analysis also showed a significant difference between the treated and untreated groups with P* values of <0.001 using the 95% confidence intervals. Also, comparing the single and combination treatments also showed a statistical significant difference between the two treatments with P** values of <0.001. The cells treated with the irrelevant peptide were similar to untreated cells.

Figure 15A:
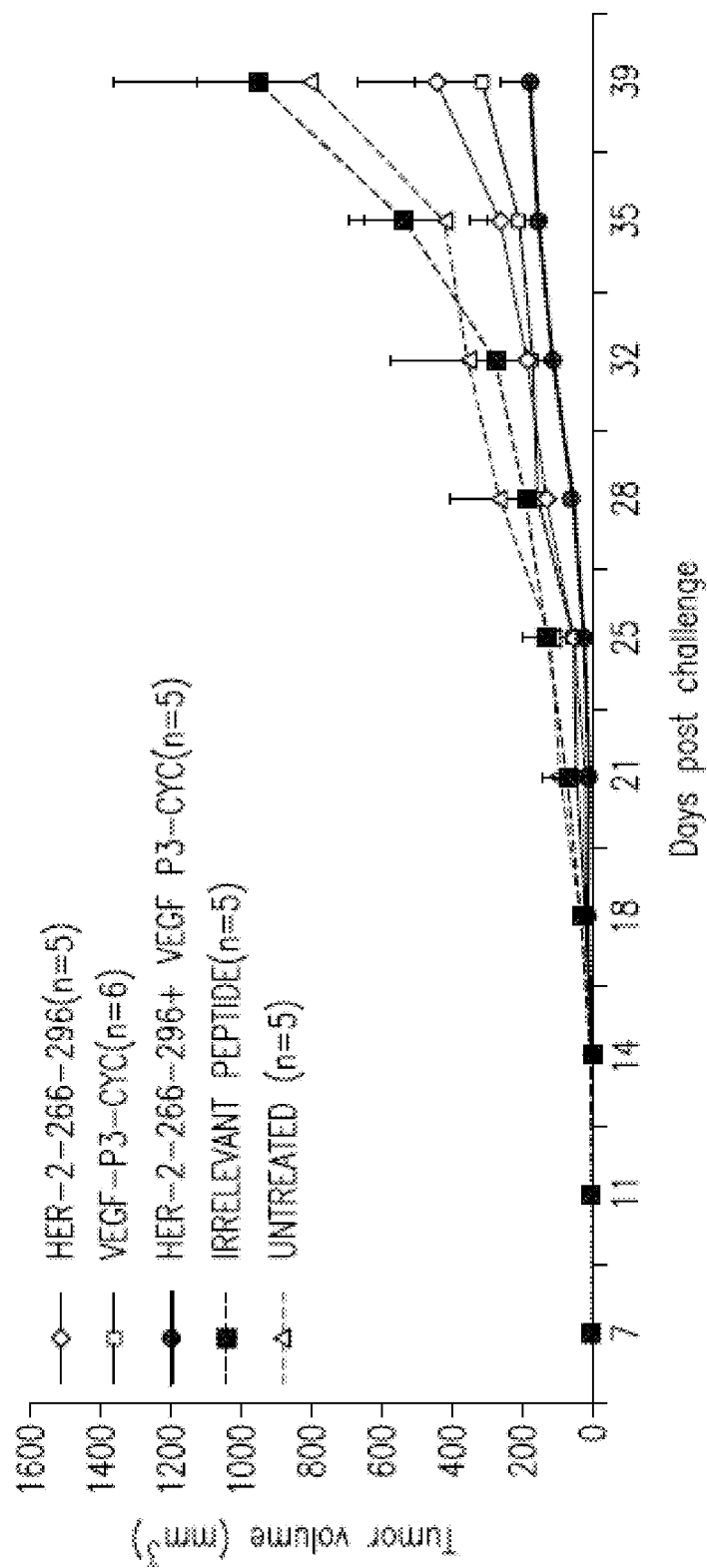
Figure 15B:
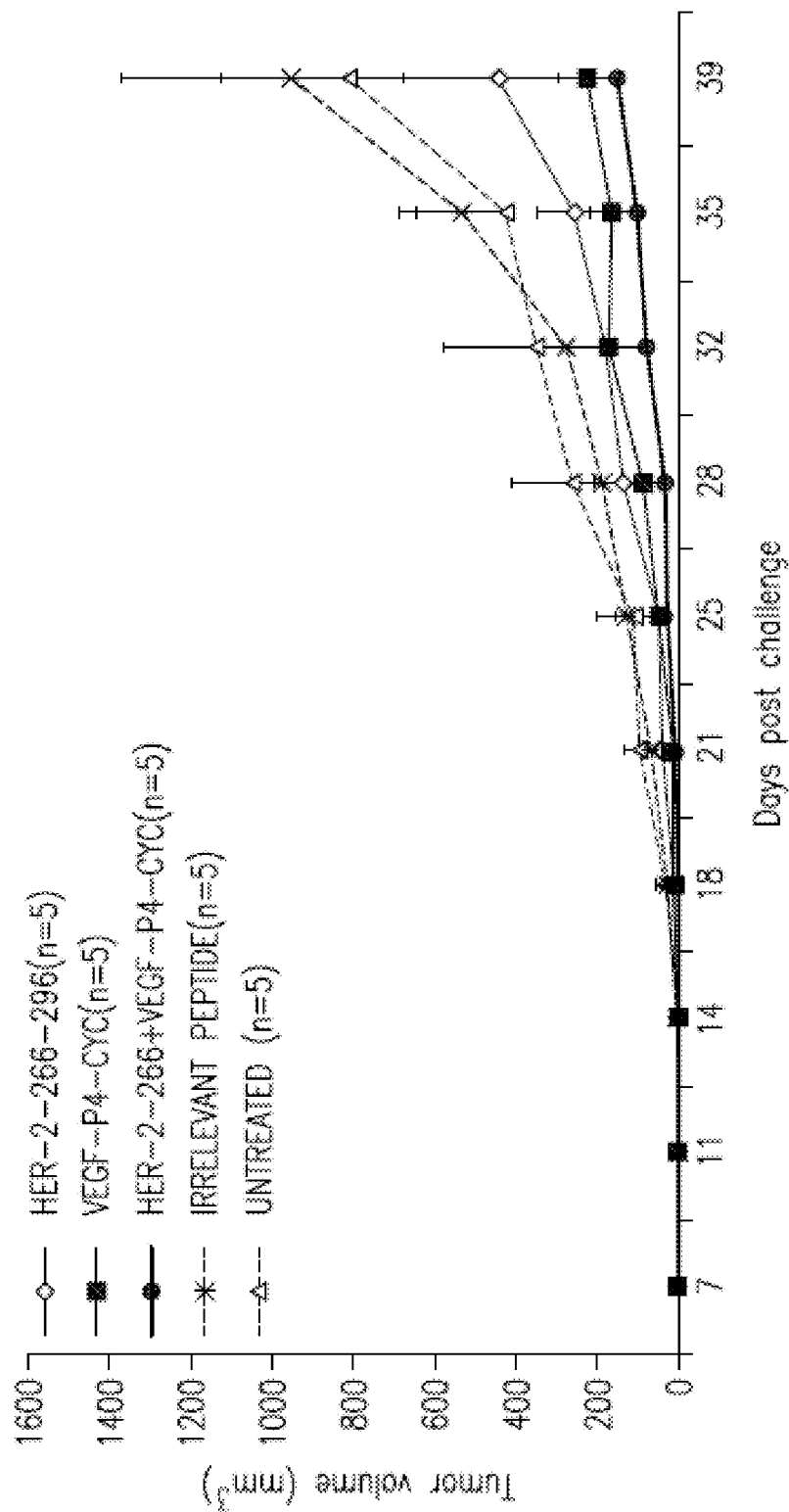
Figure 15C:
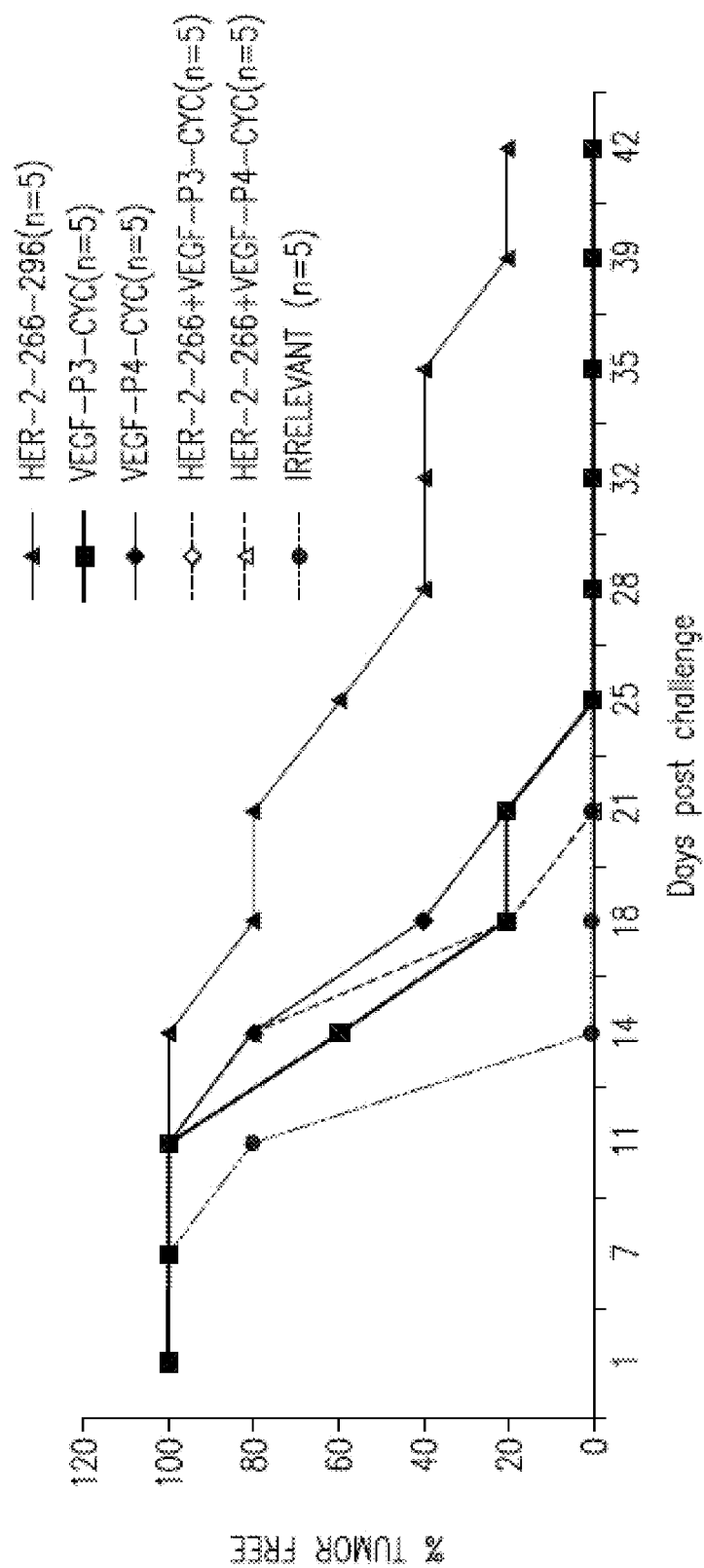
Figure 15D:
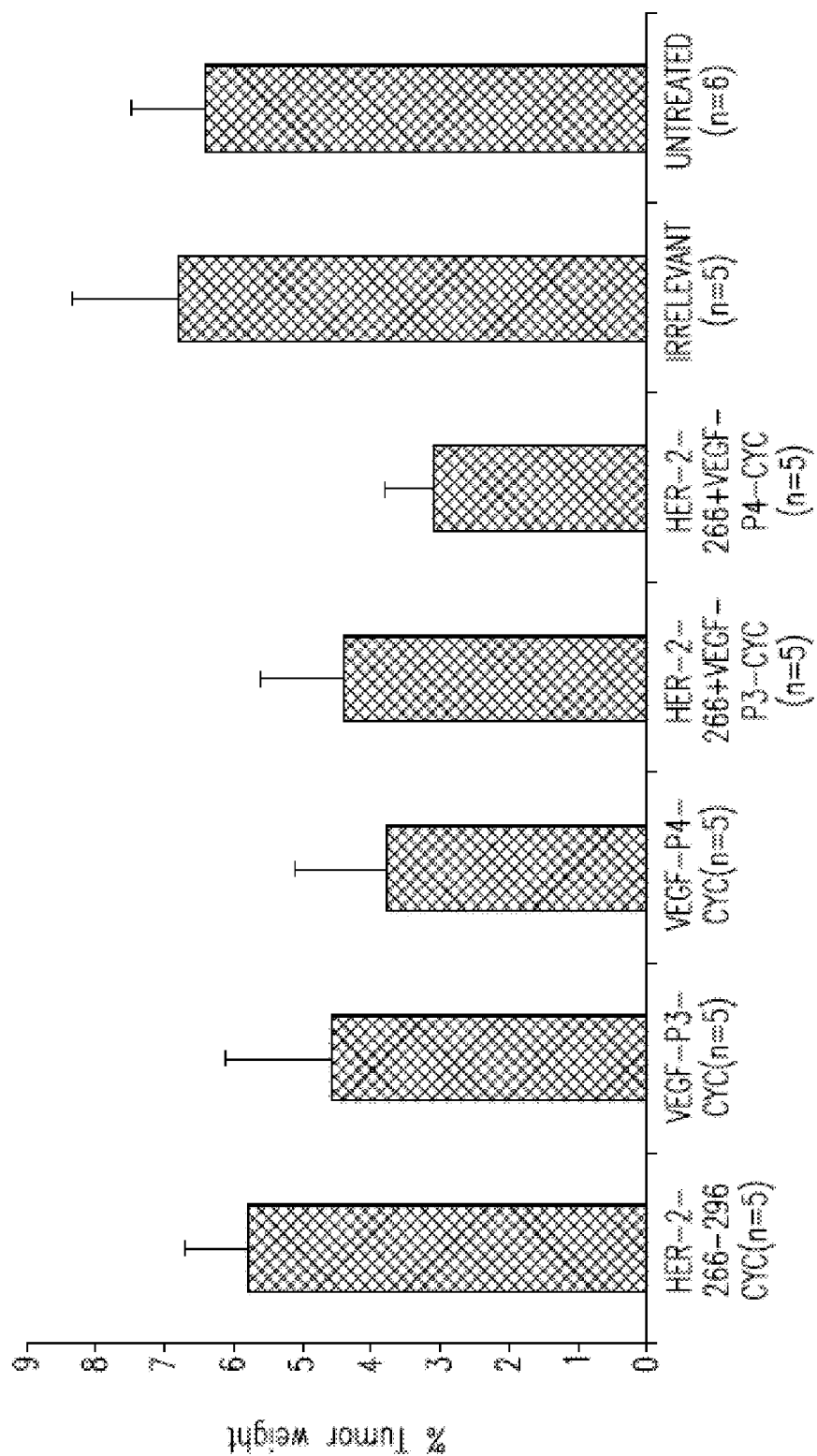

Transplantable tumor challenge models. In order to determine the ability of the peptides to inhibit tumor growth in vivo, we used a rat neu-expressing tumor challenge model. The rat neu has a 97% similarity to that of the human HER-2 266-296 sequence with only one disparate amino acid (20). To investigate the efficacy of peptide treatment, we challenged BALB/c mice with TUBO cells derived from tumors of BALB-neuT transgenic mice (23). Groups of mice (n=5) were treated with either HER-2 or VEGF peptides or a combination of both. The results indicates that combination treatment with HER-2 and VEGF peptide mimics caused greater delay in tumor growth and development (FIGS. 15A & 15B) and a significant delay in tumor growth (p* 0.003) was observed in the group treated with both HER-2 and the D-amino acid VEGF peptide (FIG. 15B). This group also produced a delay in tumor burden since it had 20% tumor free at the end of the experiment (FIG. 15C). The same combination treatment group using the D-amino acid VEGF peptide and HER-2 peptide produced a statistical significant reduction in the percent tumor weight (P#=0.05) using ANOVA analysis (FIG. 15D). There was no significant difference or delay in tumor growth between the untreated and the irrelevant peptide and tumor growth and development followed a similar pattern.

This strongly indicates that combination treatment with HER-2 and VEGF peptide mimics produced statistically significant reduction in tumor growth and development in vivo and also showed more potent anti-tumor effects in in vitro assays indicating that targeting both HER-2 and VEGF is a more attractive strategy than targeting only one of the pathway. Also, the retro inverso D-amino acid peptide produced better results than the L-amino acid peptide in both the cases of single and combination treatments as illustrated in FIG. 15C.

The receptor HER-2 has been shown to be upregulated in many types of cancers especially breast (2, 41). Weak immune responses has been detected in patients with HER-2 positive cancers indicating that the receptor is weakly immunogenic. Humanized monoclonal antibodies like Trastuzumab, Pertuzumab and Bevacizumab have been developed to treat different types of cancers. Despite their approval by the FDA, a lot of concerns still exist with passive immunotherapy using these antibodies. There is the requirement of repeated treatment with high dosing and also high cost, the immunogenicity of these antibodies resulting to production of anti-idiotypic antibodies and the development of resistance due to loss of immunodominant epitopes. Above all there is high level of toxic side effects like cardiotoxicity associated with these treatments. Immunization or treatment with peptides offers the opportunity of stimulating the body's immune response leading to immunological memory. Peptides are relatively safe, non toxic, cheaper and highly specific. The only drawback associated with peptides is their ability to be degraded by proteases in the body. This can however be overcome by using D-amino acids that cannot be recognized by proteases. The peptide can be synthesized with a reversal of the peptide chirality and using D-amino acids resulting to a topographical equivalent of the parent peptide.

The overexpression of HER-2 is associated with increased expression of VEGF at both the RNA and protein levels in human breast cancer cells and exposure of HER-2 positive cells to trastuzumab significantly decreases VEGF. Shc, a downstream adaptor protein of the HER-2 signaling pathway, has been identified as a critical angiogenic switch for VEGF production showing that VEGF is a downstream target of the HER-2 signaling pathway. This shows that, the effects of HER-2 on tumor cell behavior may be mediated in part through stimulation of angiogenesis. A two pronged approach to target cancer cells by co-immunizing with defined tumor associated antigens and angiogenesis associated antigens have been shown to have synergistic effects. All of these show that, combination therapy targeting both HER-2 and VEGF is a very promising strategy since anti-angiogenic therapy alone will only delay tumor growth and targeting HER-2 and VEGF will destroy two different tumor dependent pathways.

Work in our laboratory is mainly focused on the development of B-cell vaccines and the production of peptides for therapeutic purposes. We have designed several peptides based on the binding of the ECD of HER-2 with pertuzumab and after several in vitro and in vivo studies, the HER-2 266-296 was shown to produce superior anti-tumor effects.

Abs raised against this peptide was also able to recognize HER-2 and also inhibit tumor growth both in vitro and in vivo. Another set of peptides were also synthesized based on the binding of VEGF to its receptor VEGFR-2 and after several studies using cancer cells, HUVECs and animal models, the VEGF-P3-CYC was selected for further studies. The retro-inverso analog of the VEGF peptide was synthesized using D-amino acids.

We evaluated the antiproliferative effects of the peptides or their combinations on different cell lines. Trastuzumab has been shown to be specific to only HER-2 positive cells (36) and this was observed in our results (FIG. 13A) were no inhibition was observed with the TS/A (HER-2 negative) cell line. There was also a reduction in % inhibition in the case of MDA-468 (HER-2 low) as compared to BT-474 and SK-BR-3 (HER-2 high) cells. This indicates that the peptides were effective in inhibiting HER-2 cancer cells. The HER-2-266 peptide showed inhibitory effects also on the HER-2 negative cell line (TS/A) and this is because it is the pertuzumab-like peptide and pertuzumab is also effective in cells that are independent of HER-2 (36). After showing some level of specificity to the HER-2 receptor, we tested the effects of combination treatment with both HER-2 and VEGF peptides. We noticed that there was an increase in proliferation inhibition when combination treatment was used and the treated groups were statistically different from the untreated while the irrelevant peptide had no statistical effects on the cells (FIG. 13B).

We also evaluated the effects of combination treatment on cell viability and the results obtained showed that single treatment with HER-2 or VEGF peptides gives a viability of about 70% while combination treatment with both peptides reduces the viability to less than 25% (FIG. 14A). The difference was statistically significant between the single and combination treatment with P values of <0.001. HER-2 is known to dimerize with its partner HER-1 and HER-3 leading to receptor phosphorylation and intracellular signaling and pertuzumab mainly functions by sterically blocking this receptor from binding to its partners and is therefore classified as a dimerization inhibitor. We therefore wanted to investigate the effects of peptide treatment on phosphorylation and the results also indicated and increased in phosphorylation inhibition from less than 40% in the case of single treatments to about 70% in the case of combination treatment and the difference between these two treatments were statistically significant with P values of <0.001 (FIG. 14B).

In order to evaluate the effects of peptide treatment in vivo, we used a transplantable mouse model. BALB/c mice were challenged with TUBO cells and treated with peptides and their combinations. The results obtained indicated a statistical significance of *p<0.003 between the group treated with both HER-2 and the D-amino acid VEGF peptide (VEGF-P4-CYC) and the group treated with the Irrelevant peptide (FIG. 15B). The group treated with both the HER-2 and VEGF-P3-CYC also showed a reasonable delay in tumor growth (FIG. 15A). The group treated with the D-amino acid VEGF peptide and HER-2 peptide also had a significant difference in % tumor weight of #p=0.05 as compared to the Irrelevant peptide (FIG. 15D).

Results from our studies greatly illustrates that the peptides have potent anti-tumor activity and combination treatment with both HER-2 and VEGF peptides mimics produces additive effects. This shows that, targeting the two different proteins will produce greater antitumor and anti-angiogenic effects both in vitro and in vivo. Also from the in vivo studies, the best result was obtained in the case of combination of HER-2 with the D-amino VEGF peptide mimics. This shows that the D-amino peptide probably had a greater stability to in vitro since it cannot be degraded by proteases in the blood.

Active immunization with HER-2 peptide epitope and treatment with VEGF peptide mimics induces additive antitumor effects in vitro and in vivo.

HER-2 (human epidermal growth factor receptor-2) is an attractive target for immunotherapy given its key role in the development and metastasis of several human cancers including breast, ovarian, colon, renal, lung and gastrointestinal cancers. This receptor is overexpressed in 30% of many cancers and this overexpression results to formation of homo- and heterodimers with other members of the HER family. Dimerization leads to the transduction of positive growth signals in a ligand independent manner. HER-2 overexpression causes increased expression of VEGF at both the RNA and protein level. These two proteins HER-2 and VEGF are therefore considered good targets for cancer treatment which has led to the development of two humanized monoclonal antibodies (mAb) Pertuzumab and Bevacizumab that target HER-2 and VEGF respectively. Exposure of HER-2 overexpressing cells to trastuzumab/herceptin another mAb that targets HER-2 significantly decreases VEGF expression. Although passive immunotherapy with these Abs has been approved for treatment of advanced breast cancer, a number of concerns exist with passive immunotherapy. Treatment is expensive, and has a limited duration of action, necessitating repeated administrations of the mAb. The goal of the present study was to show that active immunization with HER-2 and treatment with VEGF peptide mimics provides greater efficacy than just immunization alone. We designed and synthesized peptides based on the binding of (i) HER-2 with Pertuzumab and (ii) VEGF with VEGFR-2 and the HER-2 peptide was collinearly synthesized with a promiscuous $T_H$ helper epitope (MVF). We show that combination treatment with antibodies raised against peptides induces potent anti-tumor and anti-angiogenic responses in vitro and in vivo. The major drawback with peptides is the fact that they are easily degraded by proteases in vivo. To address this problem, we synthesized the retro-inverso peptide using D-amino acids which cannot be degraded by proteases. We have also shown that immunization with MVF-HER-2 and treatment with the D-amino acid peptide is more potent than with the L-amino acid counterpart.

In this study, we used the MVF-HER-2 266 peptide which has been shown to be immunogenic in both rabbits and mice and also have potent anti-tumor effects in vitro and in vivo. We therefore report the in vitro effects of combination treatment with both HER-2 and VEGF anti-peptide abs that were raised in rabbits and also the anti-tumoreffects in vivo of active immunization with MVF-HER-2-266 and treatment with VEGF peptide mimics. Immunization with the HER-2 peptide epitope and treatment with the D-amino acid VEGF peptide mimic produced superior anti-tumor and anti-angiogenic effects in vivo.

Synthesis and characterization of conformational peptides. Peptide synthesis was performed on a Milligen/Biosearch 9600 peptide solid phase synthesizer (Bedford, Mass.) using Fmoc/t-But chemistry. Preloaded Fmoc-Val-CLEAR ACID resin (0.35 mmol/g) for the 266-296 and clear amide resin for the VEGF peptides (0.32 mmol/gm) (Peptides International, Louisville, Ky.) were used for synthesis. The 266-296 cyclized epitope was collinearly synthesized with the promiscuous $T_H$ epitope MVF and assembled by choosing the regioselective side chain protector Trt on Cys residues 268 and 295, and in the VEGF peptides two cysteines were inserted between amino acid Gln79 and Gly92 and between Ile80 and Glu93. Peptides were cleaved from the resin using cleavage reagent B (trifluoroacetic acid:phenol:water:TIS, 90:4:4:2), and crude peptides purified by semi preparative reversed-phase-HPLC and characterized by electrospray ionization mass spectroscopy. Intramolecular disulphide bonds were formed using iodine oxidation as described and disulphide bridge formation was further confirmed by maleimide-$PEO_2$-biotin reaction and subsequent analysis using electro-spray ionization mass spectroscopy. Peptides that were used for immunization both in rabbits and mice were collinearly synthesized with the promiscuous TH epitope MVF (MVF-HER-2-266-296, MVF-VEGF-P3-CYC and MVF-P4-CYC) (Table 4) while those that were used for intravenous treatment of mice after vaccination was synthesized without any MVF (VEGF-P3-CYC and VEGF-P4-CYC).

Circular Dichroism was done as previously described.

Animals. Female New Zealand white outbred rabbits were purchased from Harlan (Indiana, Ind.). Female BALB/c mice were purchased from the Jackson Laboratory (Bar Harbor, Me.). Animal care and use was in accordance with institutional guidelines.

Cell lines and Antibodies. All culture media, FBS, and supplements were purchased from Invitrogen Life Technologies (San Diego, Calif.). The human breast tumor cell lines BT-474 and MDA-468 were purchased from American Type Culture Collection (Rockville, Md.) and maintained according to supplier's guidelines. TUBO cells were a cloned cell line established in vitro from a lobular carcinoma that arose spontaneously in BALB-neuT mouse. Humanized mouse mAb Trastuzumab was generously provided by Genentech, Inc (South San Francisco, Calif.).

Active immunization and Ab purification. Mice and rabbits were immunized subcutaneously at multiple sites with a total of 1 mg (rabbits) or 100 μg (mice) of peptide dissolved in $ddH_2O$ emulsified (1:1) in Montanide ISA720 vehicle (Seppic) with 100 μg of N-acetylglucosamine-3-yl-acetyl-1-alanyl-d-isoglutamine (nor-MDP). Balb/c mice. Rabbits and mice were boosted with the respective doses at 3 week intervals. Rabbit blood was collected via the central auricular artery and sera tested for antibody titers. Anti-peptide antibodies were purified by affinity chromatography using a Protein A/G column (Pierce) from high titer antibody sera.

ELISA. Antibody titers were determined as previously described and it is defined as the reciprocal of the highest serum dilution with an absorbance of 0.2 or greater after subtracting the background.

Peptide treatment in transplantable mouse model. Balb/c mice 5 to 6 weeks of age were immunized with 100 μg of MVF-HER-2-266 three times at three weeks intervals. Two weeks after the third immunization, the mice were challenged with $1 \times 10^5$ TUBO cells and after challenge, mice were treated intravenously with 100 μg of either VEGF-P3-CYC, VEGF-P4-CYC or irrelevant peptide as inhibitors. Treatment was done weekly for six consecutive weeks. Mice were euthanized at week 10 and tumors removed. Tumors were measured for tumor volume twice a week using calipers and calculated using the formula (length×width)/2.

Statistical analysis. Tumor growth over time was analyzed using Stata's XTGEE (cross-sectional generalized estimating equations) model which fits general linear models that allow you to specify within animal correlation structure in data involving repeated measurements. For other experiments t-test was carried out to observe the statistical relevancy in between different sets of experiments as well as the significant difference between treated and non treated cells.

Proliferation assay. BT-474 and MDA-468 ($1 \times 10^4$) were plated in 96-well flat-bottom plates overnight. Growth medium was replaced with low sera (1% FCS) medium and the cells were incubated overnight. Media were removed from the wells and replaced with low sera medium containing anti-HER-2 peptide and anti-VEGF mimic peptides antibodies at concentrations ranging from 25-100 ug/ml and plates were incubated an additional 1 h at 37° C. before adding 10 ng/ml HRG in 1% medium. Plates were incubated for an additional 72 h at 37° C. before adding MTT (5 mg/ml) to each well. Plates were incubated 2 h at 37° C., and 100 μl of extraction buffer (20% SDS, 50% dimethylformamide (pH 4.7)) was added to each well. Plates incubated overnight at 37° C. and read on an ELISA reader at 570 nm with 655 nm background subtraction Inhibition percentage was calculated as 100%×(Untreated cells-Peptide treated cells)/(Untreated cells).

Phosphorylation assay. $1 \times 10^6$ BT-474 cells were plated in each well of a six well plate and incubated overnight at 37° C. Culture medium was removed and the cell layer washed once with PBS low score (1% FCS). Culture medium was added to the wells and plates incubated overnight. Cells were washed and 50 ug of anti-peptide Abs and controls in binding buffer (0.2% w/v BSA, RPMI 1640 medium with 10 mM HEPES (pH 7.2) was added to the wells and incubated at room temperature for 1 h. HRG (5 nM/well) was added and the incubation continued for 10 min. Binding buffer was removed and the cell layer washed once with PBS before adding 1 ml of RIPA lysis buffer (Santa Cruz Biotechnology, Santa Cruz, Calif.). Plates were rocked at 4° C. for 2 h. Lysates were removed, spun at 13000×g and supernatants collected. Protein concentration of each sample was measured by Coomassie plus protein assay reagent kit and lysates were stored at −80° C. Phosphorylation was determined by Duoset IC for human phosphor-ErbB2 according to the manufacturer's directions (RSD Systems).

ADCC. To study this, we used the bioluminescence cytotoxicity assay (aCella-TOX™ Mountain View, Calif.) and all procedures were performed according to the manufacturer's instructions. Briefly, The BT-474 target cells ($1 \times 10^4$/well) were plated on a 96 well plate and anti-peptide abs were added to the wells containing the target cells. The plate was incubated at 37° C. for 15 min to allow opsonization of antibody to occur. Effectors cells (hPBMCs from red cross) were then added to the wells at three different E:T ratios (100:1, 20:1 and 4:1) and the plate incubated at 37° C. for 3 h. The plate was then removed and equilibrated to room temperature for 15 mins before adding 10 μl of lytic agent to the control wells for maximum lysis and incubated for 15 min at room temperature. 100 μl of the Enzyme Assay reagent containing G3P was then added to all wells followed by 50 μl of the detection reagent. The plate was immediately read using a luminometer.

Viability assay. This assay was performed just like the proliferation assay but after treatment with the anti-peptide antibodies as inhibitors, the aCella-TOX reagent was used to estimate the amount of dead cells. After peptide treatment for 72 h, the plate was removed and equilibrated to room temperature for 15 mins before adding 10 μl of lytic agent to the control wells for maximum lysis and incubated for 15 min at room temperature. 100 μl of the Enzyme Assay reagent containing G3P was then added to all wells followed by 50 μl of the detection reagent. The plate was immediately read using a luminometer.

Selection, design and characterization of peptides. The crystal structure of the complex between VEGF and the Fab fragment of a humanized antibody, and analysis of the contact residues on both sides of the interface was published by Muller et al. Zilberberg et al., also identified that the sequence 79-93 of VEGF is involved in the interaction with VEGF receptor-2. Although the VEGF residues critical for antibody binding are distinct from those important for high-affinity receptor binding, they occupy a common region on VEGF demonstrating that the neutralizing effect of antibody binding results from steric blocking of VEGF-receptor interactions and only a small number of the residues buried in the VEGF-Fab interface are critical for high-affinity binding and are concentrated in one continuous segment of polypeptide loop between β5-β6. Several residues are important for VEGF receptor binding, including Met 81, Ile 83, Lys 84, Pro 85, Gln 89, and Gly92. We have selected to use a peptide encompassing residues 102-122 (numbered as 76-96 in the crystal structure) which mimics the overlapping VEGF binding sites to VEGFR-2 and Avastin. The strategy to create a conformational peptide consisting of an anti-parallel β-sheet is shown in Table 4, where the sequence was modified in a way that the ends were twisted to generate VEGF-P3(NC). It also required two artificial cysteines to be introduced between Gln79 & Gly92, and between Ile80 & Glu93. After synthesis and purification of VEGF-P3 (NC) (non cyclized) peptide, the disulfide bond was formed by oxidation reaction enabling the formation of the twisted anti-parallel β-sheet structure in the VEGF-P3 (CYC) (cyclized). The retro-inverso (RI) peptide analog VEGF-RI-P4 was synthesized using D-amino acids with the amino acid sequence in reverse order, such that the resulting peptide mimic has a reversal of the peptide backbone but a topochemical equivalence to the parent peptide in terms of side-chain orientation. The rationale behind the retro-inverso peptidomimetic is that it should present similar activity with the advantage of higher bioavailability.

HER-2-266-296 peptide (Table 4) was synthesized based on the crystal structure of the Fab of pertuzumab bound to the ECD of HER-2/neu. This reveals that pertuzumab binds to subdomain II of the HER-2 ECD. The 266-333 region of HER-2 was selected for the design of the peptides with the objective of eliciting abs against the peptide capable of inhibiting dimerization of HER-2 with other members of the EGFR family. The peptide can also be use to directly block dimerization due to its ability to bind and recognize the HER-2 ECD. Peptides that were used for immunization both in rabbits and mice were collinearly synthesized with the promiscuous T H epitope MVF while those that were used for intravenous treatment of mice after vaccination was synthesized without any MVF (Table 4). Table 4 discloses SEQ ID NOS 27 and 40, respectively, in order of appearance.

Antigenicity and Immunogenicity of Peptides. Earlier studies in our lab have shown that the MVF-HER-2-266 was highly immunogenic in both rabbits and mice. We also observed high antibody titers with the MVF-VEGF-P3 peptide (Vicar et al, unpublished) and in our present study we showed that the D-amino acid VEGF peptide (VEGF-P4-CYC) is also immunogenic though not as the L-amino acid counterparts which is probably due to the fact that D-amino acids are not natural so not easily recognized by the body. We had to do up to six immunizations with the D-amino acid peptide before we could obtain higher abs titers while with the L-amino acids only four immunization are enough to produce higher titers. We therefore used the abs raised against these peptides to test their effects on cancer cells in vitro.

Figure 16A:
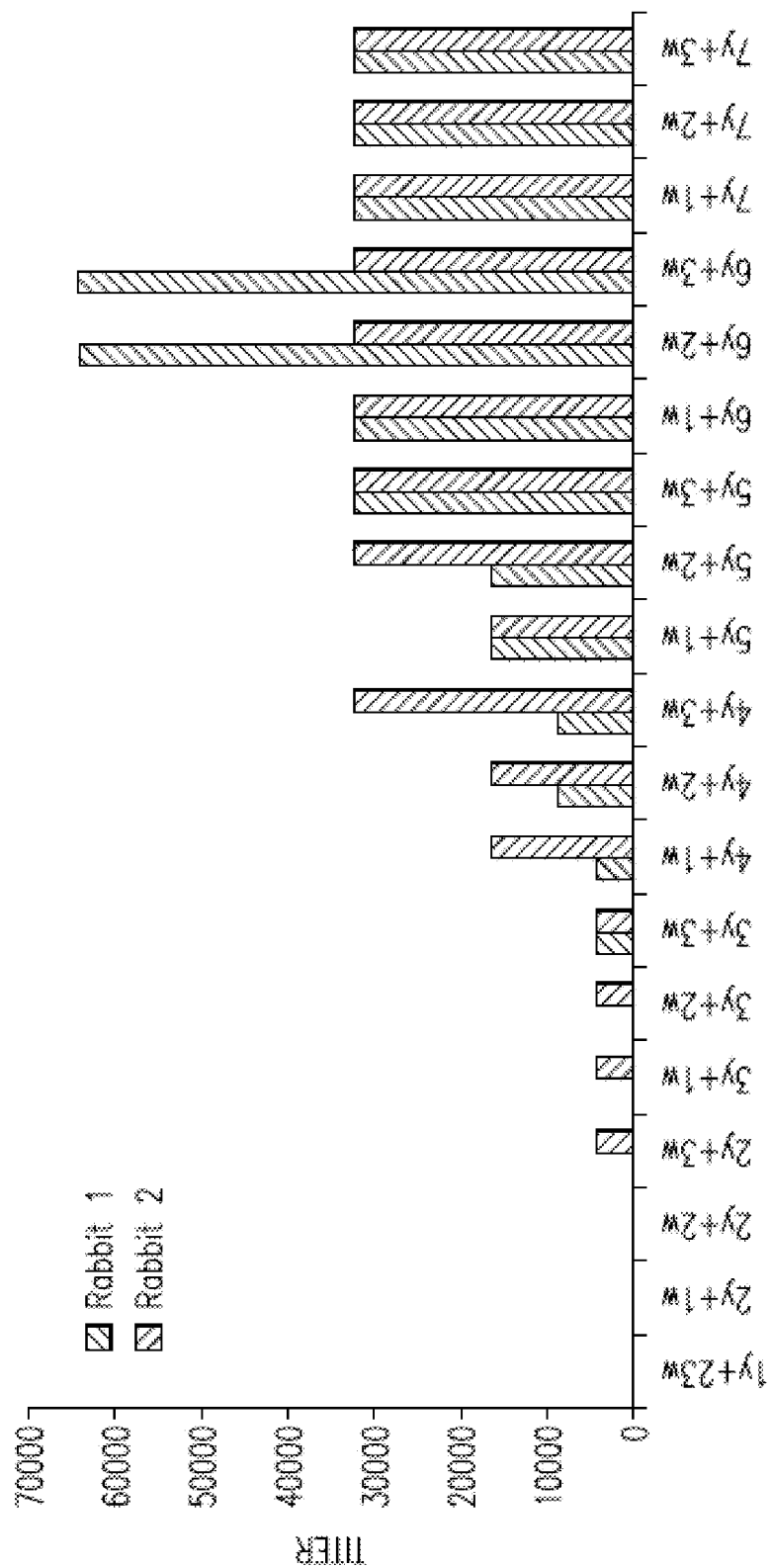
In FIG. 16A, Two rabbits were each immunized with MVF-VEGF-P4-CYC peptides. Blood was drawn weekly, and sera surveyed for peptide specific antibodies by ELISA. The results of each individual rabbit are shown and titers are defined as the reciprocal of the highest serum dilution with an absorbance of 0.2 or greater after subtracting the background. 2y+3w indicate the antibody titer in blood drawn three weeks after the second immunization.

Antiproliferative effects of anti-peptide Abs. The antiproliferative effects of the antibodies raised against the peptides in rabbits were tested using two different cell lines (Bt-474, HER-2$^{high}$ and MDA-468, HER-2$^{low}$ (FIG. 16A) in the presence of HRG to activate the HER-3 receptor. Unlike trastuzumab that is specific to HER-2 positive cells, pertuzumab is known to act on cells by disrupting ligand dependent receptor complexes independent of HER-2/neu expression. The cells were incubated with the anti-peptide antibodies followed by exposure to HRG. Results indicate that the antibodies raised against both the HER-2 peptides and VEGF peptides were able to inhibit tumor growth in a concentration dependent manner (FIG. 16A). We used two different cell lines to show that the effects of the anti peptide Abs was dependent on HER-2 expression since higher inhibition was observed in cases of high HER-2 expression (FIG. 16A). We also tested the effects of combination treatment with both HER-2 and VEGF anti-peptide Abs and the results showed an increase in rate of inhibition when both anti-peptide Abs were used as compared to single treatments (FIGS. 16B and 16C). Normal rabbit IgG did not show antiproliferative effects while Trastuzumab (positive control) showed antiproliferative effects only on cells that express the HER-2 receptor (FIG. 16A).

Figure 17A:
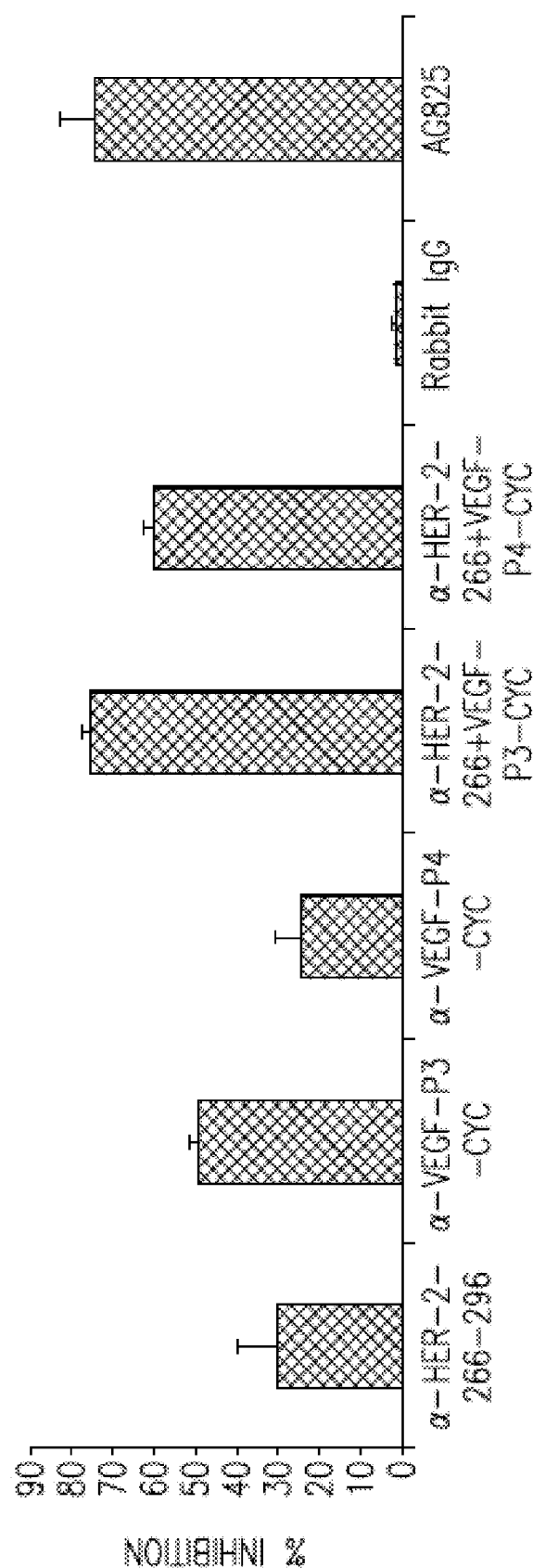
FIG. 17A shows BT474 cells were incubated with media alone, HER-2 peptide, VEGF peptides, trastuzumab, and irrelevant peptide. The number of viable cells remaining after three days was determined using the aCella-TOX reagent kit and all instructions were done according to manufacturer's instructions. Cell viability is given as a percentage of untreated cells. Data points represent the mean of three independent experiments. Error bars represent SD. Results represent average of three different experiments.

Effects of anti-peptide Abs on breast cancer cell viability. We next evaluated the effects of combination treatment with both HER-2 and VEGF anti-peptide Abs on tumor cell survival in vitro. This was done using the acella-TOX reagent kit where dead or dying cells released the enzyme GAPDH and measuring the activity of this enzyme will give an estimate of the cell viability after treatment. The results obtained showed that the Abs were able to cause a decrease in cell viability and combination treatment caused a further decrease in viability of at about 25% compared to single treatment (FIG. 17A).

Figure 17B:
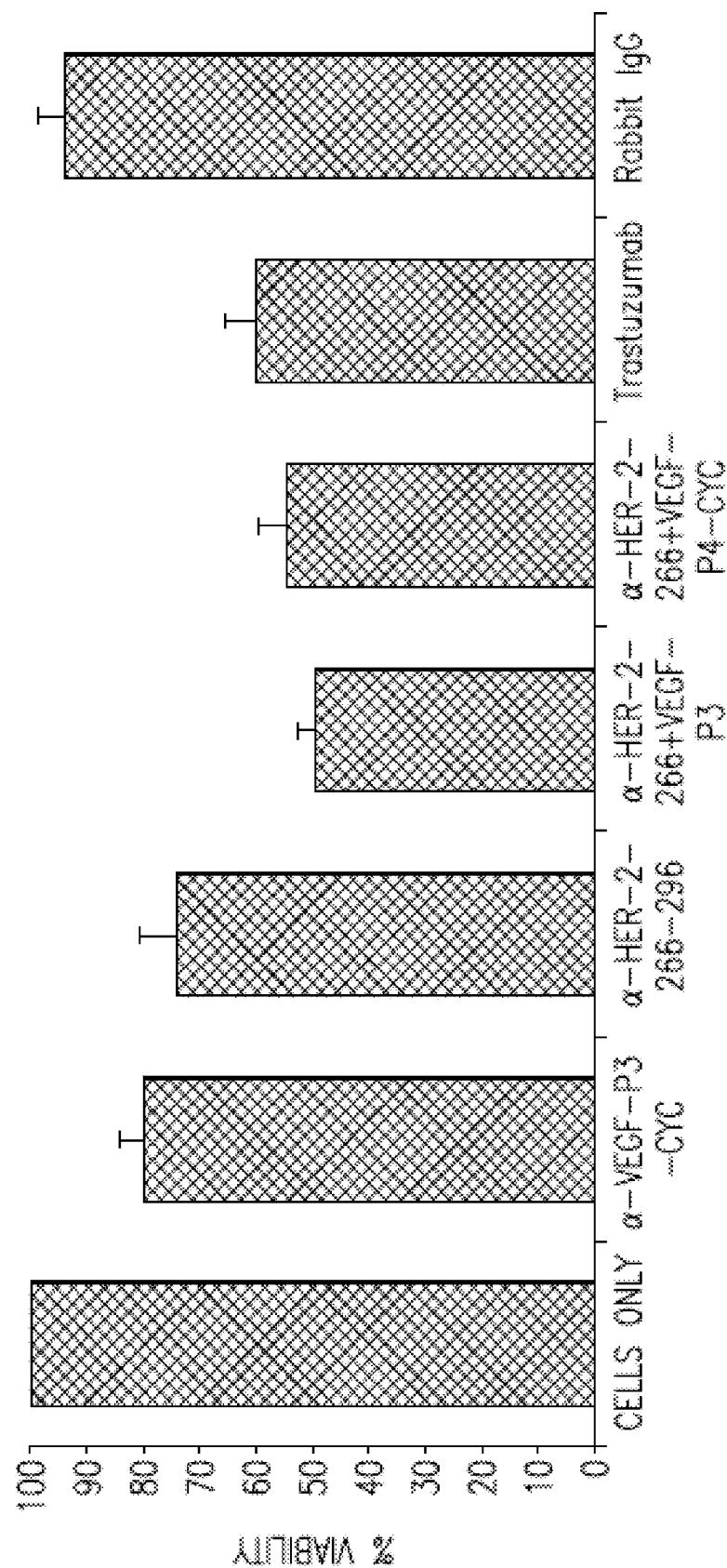
FIG. 17B shows BT-474 cells were incubated with 100 ug of HER-2 and VEGF peptides before being exposed to HRG (HER-3 activating ligand) for 10 minutes and lysed. Phosphorylated HER-2/neu was determined by indirect ELISA and percent inhibition was calculated as in FIG. 17A above. AG825 (Calbiochem) a potent HER-2 phosphorylation inhibitor was used as a positive control. Results represent average data from three different experiments. Error bars represent SD of the mean. Results represent average of three different experiments.

Effects of anti-peptide Abs on HER-2 specific Phosphorylation. The main mode of action of Pertuzumab is to inhibit phosphorylation. This is due to the fact that it sterically blocks the dimerization domain of HER-2 thereby preventing the formation of dimers with other HER receptors and thus interrupting downstream signaling. We have tested the effects of the anti-peptide Abs on HER-2 phosphorylation and the results obtained showed that these anti-peptide Abs were able to prevent phosphorylation of the HER-2 protein and single treatment with the HER-2 anti-peptide Abs alone caused a 30% inhibition rate while combination with the VEGF anti-peptide Abs increased the inhibition from 30% to about 75% (FIG. 17B). All treatments were compared to the positive control AG825 (Calbiochem), a HER-2 specific phosphorylation inhibitor. The negative control (normal rabbit IgG) showed no meaningful inhibitory effects on HER-2 phosphorylation.

Figure 18:
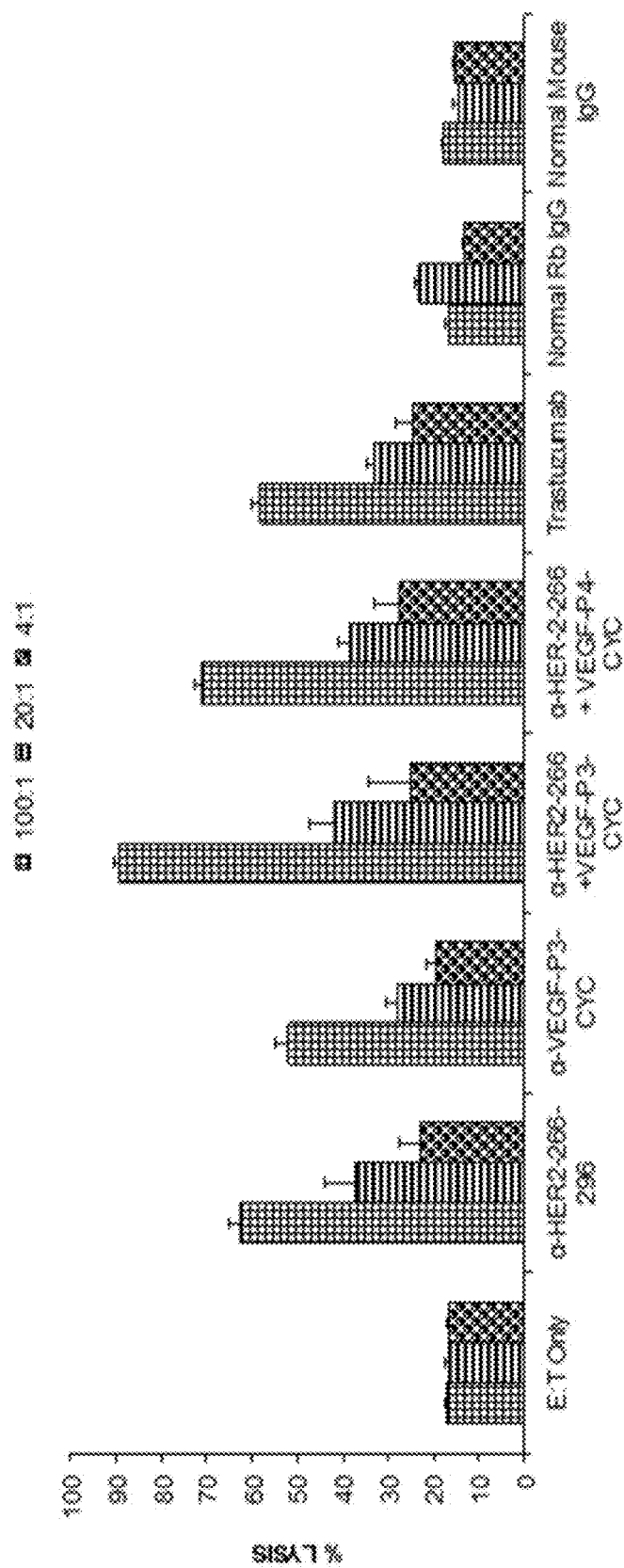
FIG. 18 shows that anti-peptide antibodies induce ADCC. Anti-peptide Abs raised in rabbits are capable of mediating antibody-dependent cell-mediated cytotoxicity (ADCC). Target cell line BT474 was coated with 50 μg of purified anti-peptide antibodies from rabbits, normal rabbit IgG, normal mouse IgG or trastuzumab and then cultured in the presence of human PBMC effector cells to give an effector: target ratio of 100:1, 20:1, and 4:1 in triplicates. Bars represent SD of mean. Results represent average data from three different experiments with each treatment performed in triplicate.

Ability of anti-peptide antibodies to mediate ADCC. It has been well documented that in vivo the Fc portions of antibodies can be of foremost importance for efficacy against tumor targets. When Fc binding is reduced or completely removed, Trastuzumab loses virtually all in vivo efficacy. We have therefore measured the ability of anti-peptide antibodies to mediate ADCC in vitro. Anti-peptide antibodies elicited in rabbits against the HER-2 and VEGF peptides were tested. To study this, we used the bioluminescence cytotoxicity assay (aCella-TOX) and all procedures were done according to the manufacturer's instructions. This method is very advantageous in that non radioactive reagents are used and is very sensitive in measuring the GAPDH enzyme released by dead or dying cells. The effector cells are normal human PBMCs from healthy donors while the target cells are BT-474 cells that overexpress HER-2. The results from these assays showed that combination treatments with peptide mimics induced a more potent response than just single treatments (FIG. 18). Trastuzumab was used as a positive control while Normal mouse and rabbit IgG were used as negative controls.

Figure 19A:
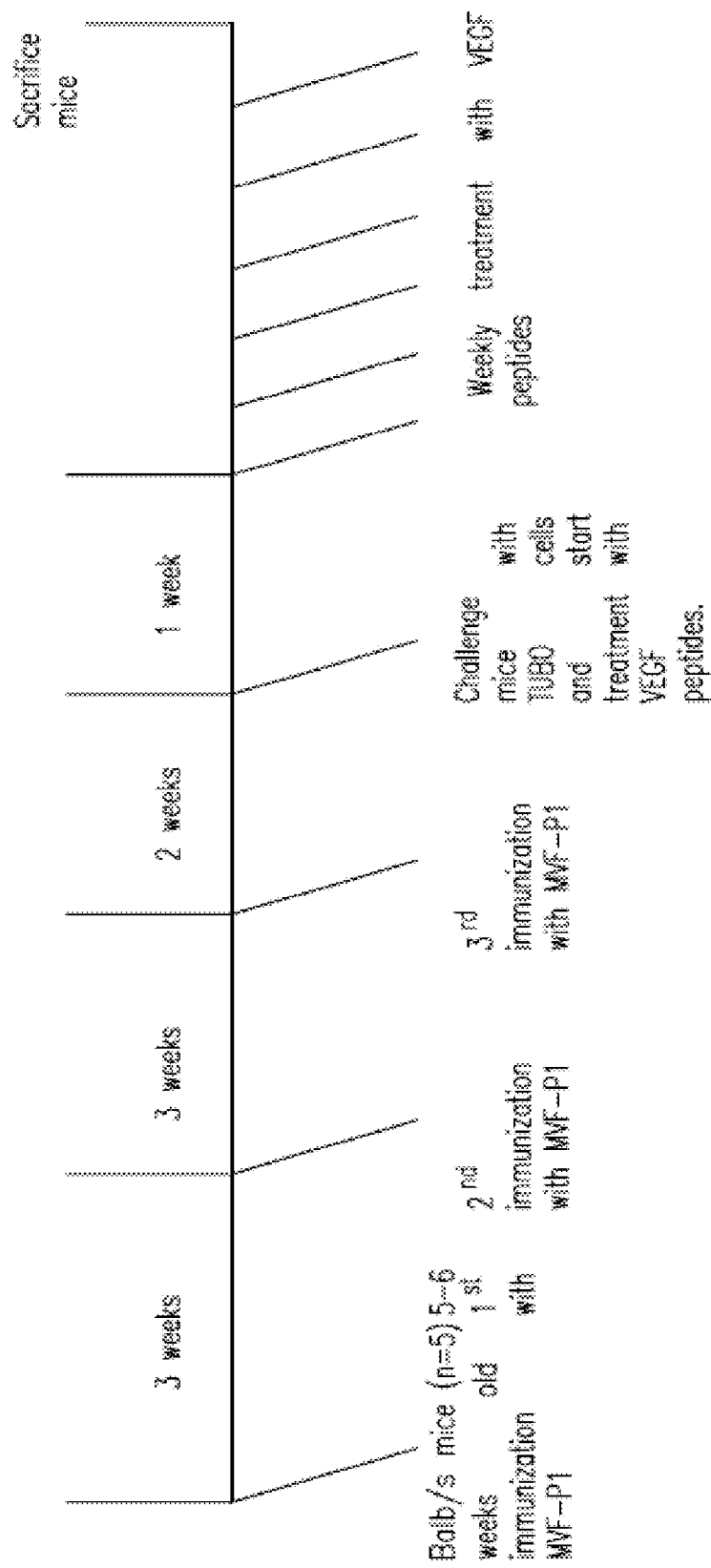
FIG. 19A: Immunization scheme for Balb/c mice. Mice were immunized subcutaneously with 100 μg of MVF-HER-2-266 three times at three weeks intervals. 2 weeks after the third immunization, mice were challenged with TUBO cells and treated weekly with VEGF peptide mimics and irrelevant peptide for 6 weeks.
Figure 19B:
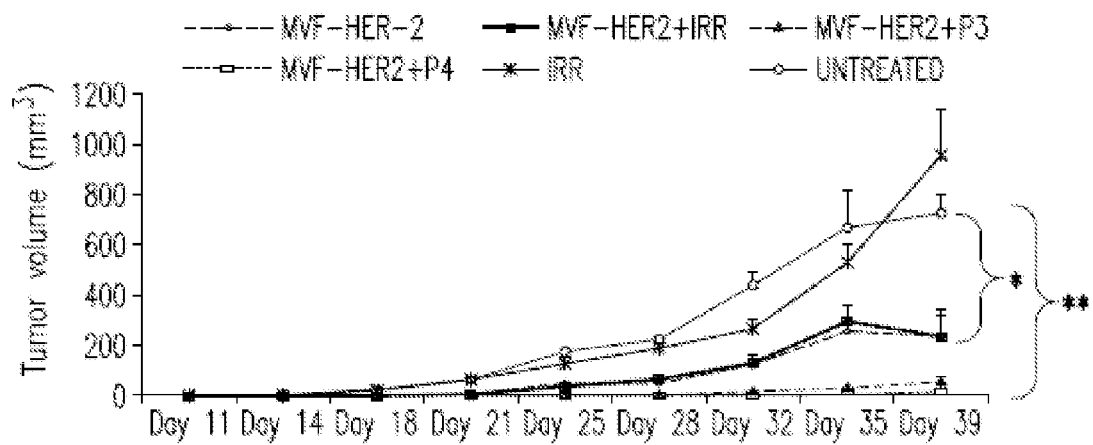
FIG. 19B: Wild type BALB/c mice (n=5), at the age of 5-7 weeks were immunized subcutaneously three times at three weeks intervals with 100 μg of MVF-HER-2-266-296 emulsified in ISA720. After immunization, mice were then challenged with TUBO cells that were derived from BALB-neuT mice which are transgenic for the rat HER-2/neu oncogene, and were treated intravenously with VEGF peptide mimics and scrambled irrelevant peptide, Tumor measurements were performed twice a week using calipers. The data are presented as the average tumor size per group and are reported as mm³ for immunization with MVF-HER-2 and treatment with VEGF peptides and Irrelevant. Results show a statistical significant difference between the group immunized with MVF-HER-2 and treated with the VEGF peptide mimics (**P<0.001) while the group that was immunized and treated with the irrelevant peptide showed a significant P value of 0.082 when compared to the untreated.
Figure 19C:
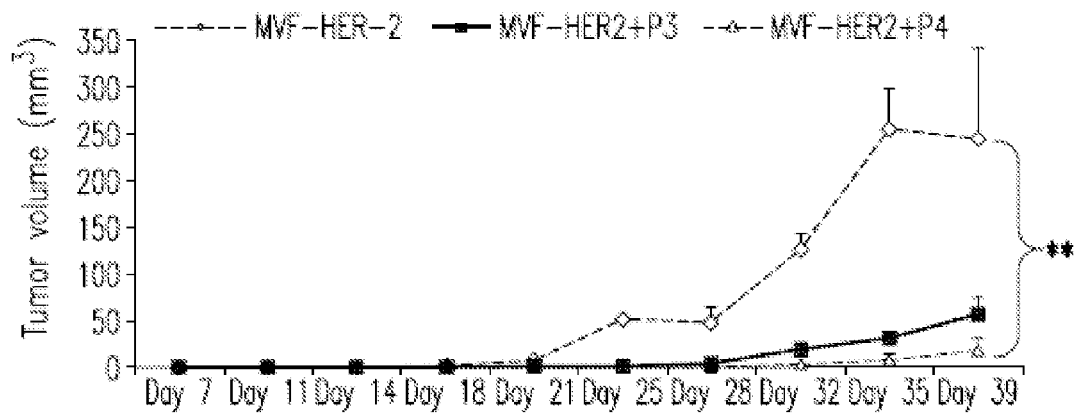
FIG. 19C: Comparison of the effects of immunization with MVF-HER-2 alone with that of immunization with MVF-HER-2 and treatment with VEGF peptide mimics. There is a significant difference between immunization plus irrelevant treatment and immunization plus treatment with VEGF peptide mimics (*P<0.001). Also there was a greater delay in tumor growth in the case of the D-amino acid VEGF peptide mimic (MVF-HER-2+P4) as compared to the case of the L-amino acid VEGF peptide (MVF-HER-2+P3).
Figure 19D:
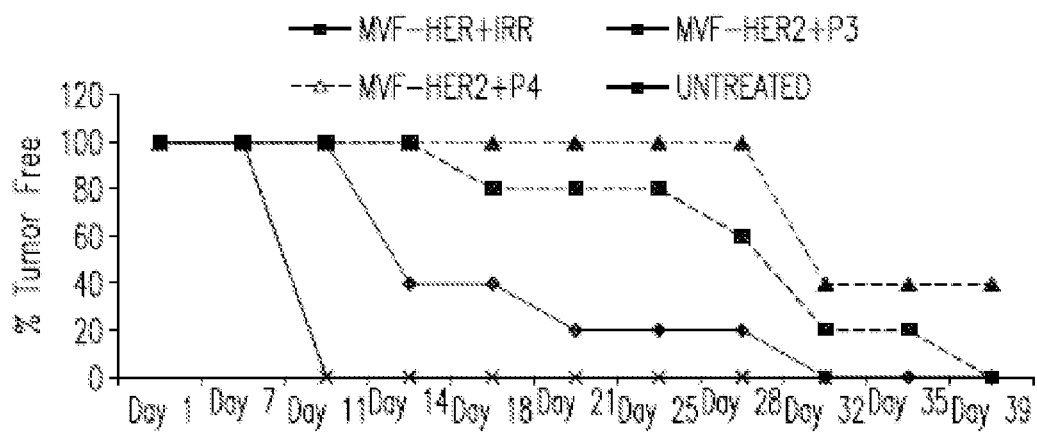
FIG. 19D: Shows the effects of immunization and treatment on tumor development. Results shows that immunization with MVF-HER-2 and treatment with VEGF-P4 (D-amino acid VEGF peptide) produced the best results since 40% of the mice (2 out of 5) remained tumor free at the end of the experiment. There was also a greater delay in onset of tumor development in the case of VEGF-P3 peptide as compared to the MVF-HER-2 immunization alone.
Figure 19E:
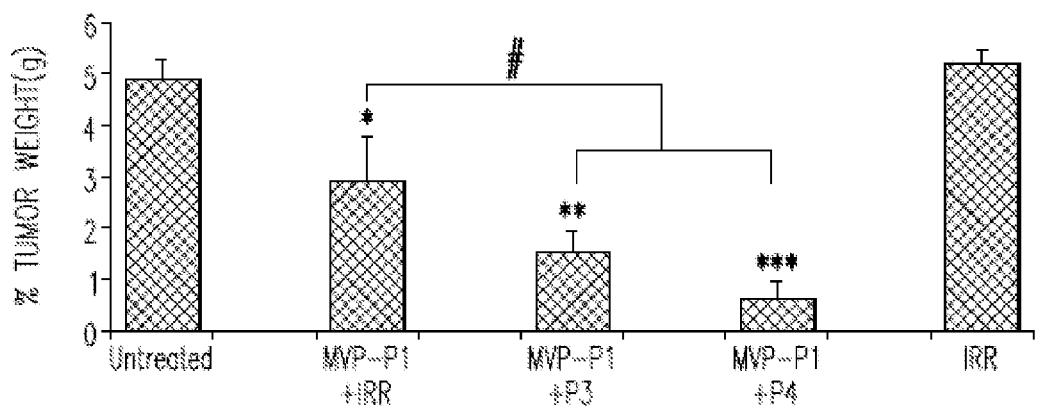
FIG. 19E: Effects of peptide treatment on % tumor weight. After treatment, the tumors were removed and weighed and the results show a significant difference between the treated groups and the untreated. The group that was immunized with MVF-HER-2 and treated with irrelevant peptide showed a P* value of 0.044. In the case of MVF-HER-2+VEGF-P3, the P value was 0.002 while in the case of MVF-HER-2+VEGF-P4, the P* value was <0.001. Comparing the effects of both immunization and treatment with VEGF peptides to that of immunization and treatment with irrelevant peptide also showed a significant difference with a P value of 0.018(#).
Figure 20:
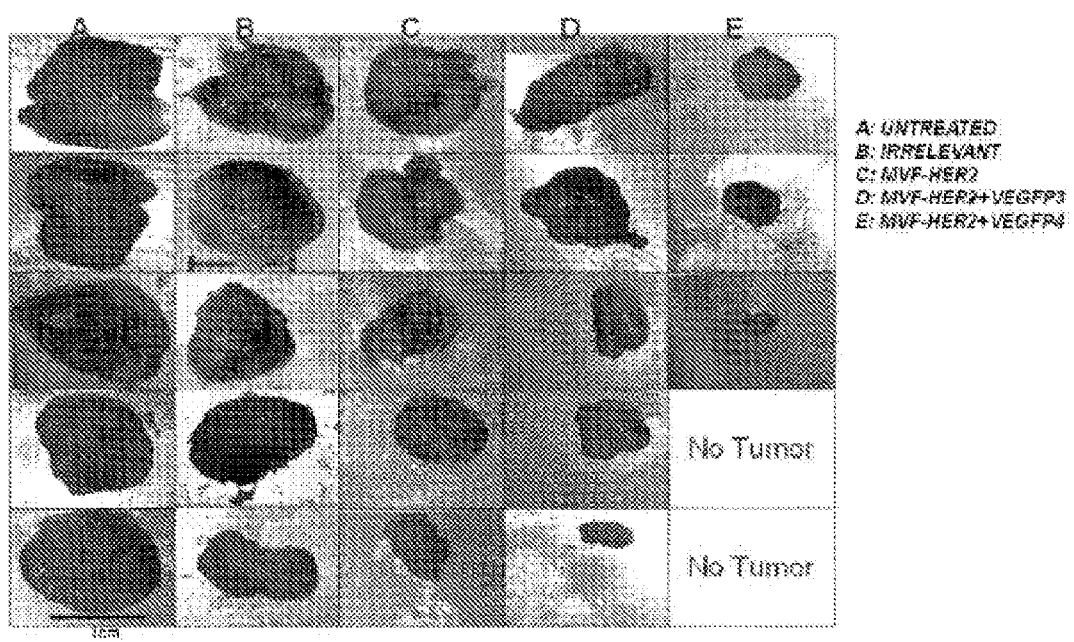
FIG. 20 shows that physical observation of the tumors showed a decrease in size in the case of the treated and also a decrease in blood since the tumors were less red in color especially in the cases of treatment with the VEGF peptide mimics.

Transplantable tumor challenge models. We used a rat neu-expressing tumor challenge model which is produced by challenging wild type Balb/c mice with TUBO cells. The rat neu has a 97% similarity to that of the human HER-2266-296 sequence with only one disparate amino acid (20). To investigate the efficacy of both immunization and peptide treatment, we immunized BALB/c mice with 100 μg of MVF-HER-2-266 peptide three times at three weeks intervals and two weeks after the third immunization, mice were challenged with TUBO cells derived from tumors of BALB-neuT transgenic mice (23). Groups of mice (n=5) were treated with either VEGF peptides, irrelevant peptide or left untreated. Results obtained indicates that immunization with MVF-HER-2 and treatment with VEGF peptide mimics caused greater delay in tumor growth and development (FIGS. 19A & 19B) and a significant delay in tumor growth (P** of <0.001) was observed (FIG. 19A). The groups that were immunized with MVF-HER-2 peptide and treated with the irrelevant peptide or just immunization alone also showed a delay in tumor growth and development though the difference was not statistically significant since the P* value was =0.082 using the 95% confidence intervals (FIG. 19A) when compared to the untreated. Most interestingly, there was a significant difference between immunization alone and immunization and treatment with the VEGF peptides. In both cases, the P* values were <0.001 but in the case of the D-amino VEGF peptide mimic (MVF-HER-2+P4), there was a greater delay in tumor growth as compared to the L-amino acid VEGF peptide (MVF-HER-2+P3) (FIG. 19B). At the end of the experiment, some of the mice were tumor free and this was observed in the case of both immunization with MVF-HER-2 and treatment with the D-amino acid VEGF peptide (MVF-HER-2+P4) where 40% of the mice (2 out of 5) did not develop tumors (FIG. 19C). We also measured the tumor weights after the experiment and calculated the % tumor weights and the results indicated a statistical difference between all treatments except the irrelevant with the untreated. The P* value was <0.001 in the case of both immunization with MVF-HER-2 and treatment with the D-amino acid VEGF peptide while the P value was <0.002 in the case of immunization and treatment with the L-amino acid VEGF peptide. In the case of immunization alone, the difference was also statistically significant with a P* of 0.044. We also compared the group of immunization with HER-2 alone to that of both immunization and treatment with VEGF peptides and we observed a statistically significant difference using the 95% confidence interval with a P# value of 0.018 (FIG. 19D). Physical observation of the tumors showed a decrease in size in the case of the treated and also a decrease in blood since the tumors were less red in color especially in the cases of treatment with the VEGF peptide mimics (FIG. 20). Also there was a great evidence of a decrease in blood flow to the tumors and normalization of the tumor vasculature in the case of immunization with MVF-HER-2 and treatment with VEGF peptides (FIGS. 21 C&D) while immunization and treatment with irrelevant peptide only decreases tumor size but no effect on blood supply (FIG. 21B). Results from these studies strongly suggest that targeting both HER-2 and VEGF is a better strategy that can completely prevent tumor growth and development. Also, the retro inverso D-amino acid peptide produced better results than the L-amino acid peptide in both the cases of single and combination treatments as illustrated in FIGS. 19B, 19C, 19D, and 21D.

The receptor HER-2 has been shown to be upregulated in many types of cancers especially breast. Weak immune responses has been detected in patients with HER-2 positive cancers indicating that the receptor is weakly immunogenic. Humanized monoclonal antibodies like Trastuzumab, Pertuzumab and Bevacizumab have been developed to treat different types of cancers. Despite their approval by the FDA, a lot of concerns still exist with passive immunotherapy using these antibodies. There is the requirement of repeated treatment with high dosing and also high cost, the immunogenicity of these antibodies resulting to production of anti-idiotypic antibodies and the development of resistance due to loss of immunodominant epitopes. Above all there is high level of toxic side effects like cardiotoxicity associated with these treatments. Immunization or treatment with peptides offers the opportunity of stimulating the body's immune response leading to immunological memory. Peptides are relatively safe, non toxic, cheaper and highly specific. The only drawback associated with peptides is their ability to be degraded by proteases in the body. This can however be overcome by using D-amino acids that cannot be recognized by proteases. The peptide can be synthesized with a reversal of the peptide chirality and using D-amino acids resulting to a topographical equivalent of the parent peptide.

The overexpression of HER-2 is associated with increased expression of VEGF at both the RNA and protein levels in human breast cancer cells and exposure of HER-2 positive cells to trastuzumab significantly decreases VEGF. Shc, a downstream adaptor protein of the HER-2 signaling pathway, has been identified as a critical angiogenic switch for VEGF production showing that VEGF is a downstream target of the HER-2 signaling pathway. This shows that, the effects of HER-2 on tumor cell behavior may be mediated in part through stimulation of angiogenesis. A two pronged approach to target cancer cells by co-immunizing with defined tumor associated antigens and angiogenesis associated antigens have been shown to have synergistic effects. All of these show that, combination therapy targeting both HER-2 and VEGF is a very promising strategy since anti-angiogenic therapy alone will only delay tumor growth and targeting HER-2 and VEGF will destroy two different tumor dependent pathways.

During the past decade, work in our laboratory was mainly focused on the development of B-cell vaccines targeting the HER-2 epitope. The association between HER-2 and VEGF and the Folkman's idea that tumor growth is angiogenesis dependent attracted us to targeting these two different proteins. Our main hypothesis is that immunization with HER-2 peptide epitopes will produce highly specific antibodies that will fight cancer cells and treatment with VEGF peptides will be able to prevent angiogenesis thereby preventing tumor growth due to decrease in blood and oxygen supply. We there for hypothesized that targeting these two sub pathways will most efficiently prevent the establishment of tumors. We have designed several peptides based on the binding of the ECD of HER-2 with pertuzumab and after several in vitro and in vivo studies, the HER-2 266-296 was shown to produce superior anti-tumor effects. Abs raised against this peptide was also able to recognize HER-2 and also inhibit tumor growth both in vitro and in vivo. Another set of peptides were also synthesized based on the binding of VEGF to its receptor VEGFR-2 and after several studies using cancer cells and animal models, the VEGF-P3-CYC was selected for further studies. The retro-inverso analog of the VEGF peptide was synthesized using D-amino acids. The peptides were immunogenic though the D-amino acid peptide needed more booster immunizations before higher titers could be obtained (FIG. 17).

Figure 16D:
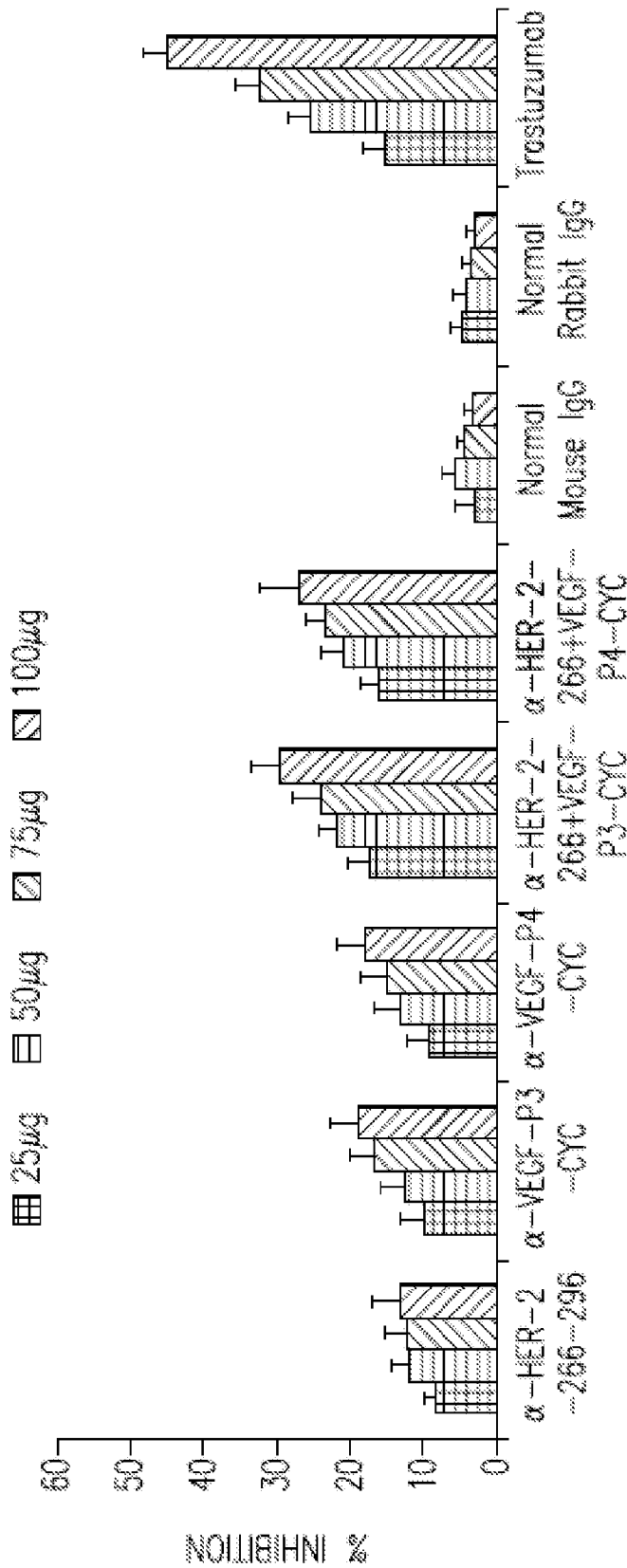
FIG. 16D shows BT-474 cells were treated in the same manner as in FIG. 16B and treated with HER-2 peptide, VEGF peptides or combination of both. Trastuzumab and irrelevant peptide were used as positive and negative controls. Rate of inhibition was calculated using the same formula in FIG. 16B and all results represents the average of three different experiments. Error bars represent SD of the mean. Results represent average of three different experiments.

We evaluated the antiproliferative effects of the anti-peptide Abs or their combinations on different cell lines. Trastuzumab has been shown to be specific to only HER-2 positive cells and this was observed in our results (FIG. 16A) where little inhibition was observed with the MDA-468 (HER-2 low) cell line as compared to the BT-474 cell line (HER-2 high). The anti-peptide abs were effective in inhibiting HER-2 cancer cells. The HER-2-266 peptide abs showed some inhibitory effects on the HER-2 low cell line (MDA-468) (FIG. 16A) and this is probably due to the fact that the peptide was synthesized using the pertuzumab epitope so Abs raised against this peptide should be able to function like pertuzumab so should have some inhibitory effects in cells independent of HER-2 since pertuzumab is also effective in cells that are independent of HER-2. We also evaluated the in vitro effects of combination treatment with both HER-2 and VEGF anti-peptide abs on cell proliferation and viability, and the results illustrates that combination treatment produce greater anti-tumor effects than single treatments alone. (FIGS. 16B-16D).

HER-2 is known to dimerize with its partner HER-1 and HER-3 leading to receptor phosphorylation and intracellular signaling and pertuzumab mainly functions by sterically blocking this receptor from binding to its partners and is therefore classified as a dimerization inhibitor. We therefore investigated the effects of the anti-peptide abs on phosphorylation and the results also showed and increased in phosphorylation inhibition from less than 35% in the case of single treatments to about 75% in the case of combination treatment (FIG. 17B). One of the main mode of action of Abs is to cause ADCC, so we also evaluated the ability of anti-peptide abs to cause ADCC of BT-474 cells. Results showed that the anti-peptide abs were able to cause ADCC and their effects were comparable to that of the positive control Trastuzumab (FIG. 17C). Also in the case of combination treatment with both anti-HER-2 and anti-VEGF peptide abs, there was an increase in ADCC as compared to single treatments. The combination treatment was greater than that of Trastuzumab.

In order to evaluate the effects of peptide treatment in vivo, we used a transplantable mouse model. BALB/c mice were immunized with MVF-HER-2 peptide before being challenged with TUBO cells and treated with VEGF peptides. The results obtained showed significant differences between the treated groups and the untreated and also a delay in tumor growth and development, with a decrease in tumor weight. The case of immunization with MVF-HER-2 and treatment with VEGF-P4 produced the best results and 40% of the mice in this group remained tumor free at the end of the experiment (FIG. 19A-19D). The VEGF peptide treatment also appeared to cause a decrease in blood flow to the tumors thereby limiting their size increase (FIGS. 20 & 21) and normalization of the tumor vasculature (FIGS. 21C & 21D). The results strongly suggest that tumor growth and development can be completely prevented by targeting both the tumors and preventing blood supply. This is because; the tumor cells are genetically unstable so they constantly changes thereby developing resistance but the tumor vasculature is genetically stable. Targeting both the genetically stable vasculature will be able to prevent the tumors that develop resistance overtime from growing thereby producing greater inhibitory effects. Active immunization with HER-2 peptide epitopes and treatment with VEGF peptide mimics is a better strategy than immunization alone. Also, the D-amino acid peptide produces greater inhibitory effects probably due to its longer half-life in vivo due to inability of proteases to recognize it.

What is claimed is:

1. A composition comprising a VEGF peptide, wherein the VEGF peptide comprises ITMQCGIHQGQHPKIRMICEMSF (SEQ ID NO: 41), wherein the two cysteine residues of the VEGF peptide are linked by a disulfide bond.

2. The composition of claim 1, wherein the VEGF peptide forms a twisted, anti-parallel, β-sheet structure.

3. The composition of claim 2, wherein the VEGF peptide mimics the structure of amino acids 102 to 122 in native VEGF.

4. The composition of claim 3, wherein the VEGF peptide mimic binds to a VEGF receptor.

5. The composition of claim 4, wherein the VEGF receptor is selected from the group consisting of VEGFR-1, VEGFR-2, and VEGFR-3.

6. The composition of claim 5, wherein the VEGF receptor is VEGFR-2.

7. The composition of claim 1, wherein the VEGF peptide further comprises a T-cell epitope selected from the group consisting of:

```
                                    (SEQ ID NO: 2)
KLLSLIKGVIVHRLEGVE;

(SEQ ID NO: 3)
NSVDDALINSTIYSYFPSV;

(SEQ ID NO: 4)
PGINGKAIHLVNNQSSE;

(SEQ ID NO: 5)
QYIKANSKFIGITEL;

(SEQ ID NO: 6)
FNNFTVSFWLRVPKVSASHLE;

(SEQ ID NO: 7)
LSEIKGVIVHRLEGV;

(SEQ ID NO: 8)
FFLLTRILTIPQSLN;
and (SEQ ID NO: 9)
TCGVGVRVRSRVNAANKKPE.
```

8. The composition of claim 7, wherein the VEGF peptide further comprises a linker between the VEGF peptide and T-cell epitope.

9. The composition of claim 8, wherein the linker comprises a sequence that is between 1 and 15 amino acids in length.

10. The composition of claim 9, wherein the linker comprises an amino acid sequence of GPSL (SEQ ID NO: 10).

11. A composition comprising a VEGF peptide, wherein the VEGF peptide comprises ITMQCGIHQGQHPKIRMICEMSF (SEQ ID NO: 41) in retro-inverso form (VEGF-RI-P4) or the retro-inverso form wherein the two cysteine residues are linked by a disulfide bond.

12. The composition of claim 11, wherein the two cysteine residues of the retro-inverso VEGF peptide are linked by a disulfide bond (VEGF-RI-P4(CYC)).

13. The composition of claim 1, further comprising at least one HER-2 epitope or a cyclized form or its retro-inverso form, wherein the HER-2 epitope is selected from the group consisting of:

```
                                    (SEQ ID NO: 11)
TGTDMKLRLPASPETHLDM;

(SEQ ID NO: 12)
AVLDNGDPLNNTTPVTGASPGG;

(SEQ ID NO: 13)
LWKDIFHKNNQLALTLIDTNRS;

(SEQ ID NO: 14)
TLIDTNRSRACHPCSPMCKGSRCWGESSEDCQSLT;

(SEQ ID NO: 15)
ALVTYNTDTFESMPNPEGRYT;

(SEQ ID NO: 16)
PLHNQEVTAEDGTQRAEKCSKPCA;

(SEQ ID NO: 17)
PESFDGDPASNTAPLQPE;

(SEQ ID NO: 18)
LYISAWPDSLPDLSVFQNLQ;

(SEQ ID NO: 19)
LFRNPHQALLHTANRPEDE;

(SEQ ID NO: 20)
CLPCHPECQPQNGSVTCFGPEADQCVACAHYKDP;

(SEQ ID NO: 21)
KPDLSYMPIWKFPDEEGA;

(SEQ ID NO: 22)
INGTHSCVDLDDKGCPAEQRAS;

(SEQ ID NO: 23)
CHPECQPQNGSVTCFGPEADQVACAHYKDPPFCVA;

(SEQ ID NO: 24)
VACAHYKDPPFCVA;

(SEQ ID NO: 25)
VARCPSGVKPDLSYMPIWKFPDEEGACQPL;

(SEQ ID NO: 26)
IWKFPDEEGACQPL;

(SEQ ID NO: 27)
LHCPALVTYNTDTFESMPNPEGRYTFGASCV;

(SEQ ID NO: 28)
ACPYNYLSTDVGSCTLVCPLHNQEVTAEDGTQRCEK;

(SEQ ID NO: 29)
CPLHNQEVTAEDGTQRCEK;
and
```

-continued

CPINCTHSCVDLDDKGCPAEQRAS. (SEQ ID NO: 30)

14. The composition of claim 13, wherein the HER-2 epitope is cyclized.

15. The composition of claim 13, wherein the HER-2 epitope is in retro-inverso form.

16. The composition of claim 13, wherein the HER-2 epitope is immunogenic.

17. The composition of claim 13, wherein the HER-2 epitope further comprises a T-cell epitope selected from the group consisting of:

KLLSLIKGVIVHRLEGVE; (SEQ ID NO: 31)

NSVDDALINSTIYSYFPSV; (SEQ ID NO: 32)

PGINGKAIHLVNNQSSE; (SEQ ID NO: 33)

QYIKANSKFIGITEL; (SEQ ID NO: 34)

-continued

FNNFTVSFWLRVPKVSASHLE; (SEQ ID NO: 35)

LSEIKGVIVHRLEGV; (SEQ ID NO: 36)

FFLLTRILTIPQSLN; (SEQ ID NO: 37)
and

TCGVGVRVRSRVNAANKKPE. (SEQ ID NO: 38)

18. The composition of claim 17, wherein the HER-2 epitope further comprises a linker of from 1 to 15 amino acids in length.

19. The composition of claim 18, wherein the linker comprises an amino acid sequence of GPSL (SEQ ID NO: 10).

20. A method of treating cancer in a subject comprising administering a pharmaceutical composition to the subject, the pharmaceutical composition comprising a pharmaceutically acceptable vehicle, and at least one composition of claim 1, 7, 13, or 17.

* * * * *

UNITED STATES PATENT AND TRADEMARK OFFICE
CERTIFICATE OF CORRECTION

PATENT NO. : 9,504,738 B2
APPLICATION NO. : 13/662024
DATED : November 29, 2016
INVENTOR(S) : Kaumaya Pravin Page 1 of 1

It is certified that error appears in the above-identified patent and that said Letters Patent is hereby corrected as shown below:

In the Specification

In Column 1, Lines 18-24, cancel the text beginning with "This invention was made" to and ending "rights in the invention." and insert the following paragraph:
--STATEMENT REGARDING FEDERALLY SPONSORED RESEARCH
This invention was made with government support under CA084356 awarded by the National Institutes of Health. The government has certain rights in the invention.--

Signed and Sealed this
Twenty-seventh Day of November, 2018

Andrei Iancu
*Director of the United States Patent and Trademark Office*

UNITED STATES PATENT AND TRADEMARK OFFICE
CERTIFICATE OF CORRECTION

PATENT NO. : 9,504,738 B2
APPLICATION NO. : 13/662024
DATED : November 29, 2016
INVENTOR(S) : Kaumaya Pravin It is certified that error appears in the above-identified patent and that said Letters Patent is hereby corrected as shown below:

In the Specification

Column 1, Lines 22-24 replace the Government Support Clause with:
--This invention was made with government support under grant number CA084356 awarded by the National Institutes of Health. The government has certain rights in the invention.--

This certificate supersedes the Certificate of Correction issued November 27, 2018.

Signed and Sealed this
Fourth Day of August, 2020

Andrei Iancu
*Director of the United States Patent and Trademark Office*

SEQUENCE LISTING

```
<160> NUMBER OF SEQ ID NOS: 41

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 1

Ile Thr Met Gln Cys Gly Ile His Gln Gly Gln His Pro Lys Ile Met
1               5                   10                  15

Ile Cys Glu Met Ser Phe
            20

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 2

Lys Leu Leu Ser Leu Ile Lys Gly Val Ile Val His Arg Leu Glu Gly
```

Val Glu

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 3

Asn Ser Val Asp Asp Ala Leu Ile Asn Ser Thr Ile Tyr Ser Tyr Phe
1               5                   10                  15

Pro Ser Val

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 4

Pro Gly Ile Asn Gly Lys Ala Ile His Leu Val Asn Asn Gln Ser Ser
1               5                   10                  15

Glu

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 5

Gln Tyr Ile Lys Ala Asn Ser Lys Phe Ile Gly Ile Thr Glu Leu
1               5                   10                  15

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 6

Phe Asn Asn Phe Thr Val Ser Phe Trp Leu Arg Val Pro Lys Val Ser
1               5                   10                  15

Ala Ser His Leu Glu
            20

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 7

Leu Ser Glu Ile Lys Gly Val Ile Val His Arg Leu Glu Gly Val
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: note = synthetic construct

<400> SEQUENCE: 8

Phe Phe Leu Leu Thr Arg Ile Leu Thr Ile Pro Gln Ser Leu Asn
1               5                   10                  15

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: note = synthetic construct

<400> SEQUENCE: 9

Thr Cys Gly Val Gly Val Arg Val Arg Ser Arg Val Asn Ala Ala Asn
1               5                   10                  15

Lys Lys Pro Glu
            20

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: note = synthetic construct

<400> SEQUENCE: 10

Gly Pro Ser Leu
1

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: note = synthetic construct

<400> SEQUENCE: 11

Thr Gly Thr Asp Met Lys Leu Arg Leu Pro Ala Ser Pro Glu Thr His
1               5                   10                  15

Leu Asp Met

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: note = synthetic construct

<400> SEQUENCE: 12

Ala Val Leu Asp Asn Gly Asp Pro Leu Asn Asn Thr Thr Pro Val Thr
1               5                   10                  15

Gly Ala Ser Pro Gly Gly
            20

```
<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 13

Leu Trp Lys Asp Ile Phe His Lys Asn Asn Gln Leu Ala Leu Thr Leu
1               5                   10                  15

Ile Asp Thr Asn Arg Ser
            20

<210> SEQ ID NO 14
<211> LENGTH: 35
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 14

Thr Leu Ile Asp Thr Asn Arg Ser Arg Ala Cys His Pro Cys Ser Pro
1               5                   10                  15

Met Cys Lys Gly Ser Arg Cys Trp Gly Glu Ser Ser Glu Asp Cys Gln
            20                  25                  30

Ser Leu Thr
        35

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 15

Ala Leu Val Thr Tyr Asn Thr Asp Thr Phe Glu Ser Met Pro Asn Pro
1               5                   10                  15

Glu Gly Arg Tyr Thr
            20

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 16

Pro Leu His Asn Gln Glu Val Thr Ala Glu Asp Gly Thr Gln Arg Ala
1               5                   10                  15

Glu Lys Cys Ser Lys Pro Cys Ala
            20

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: note =
``` synthetic construct

<400> SEQUENCE: 17

Pro Glu Ser Phe Asp Gly Asp Pro Ala Ser Asn Thr Ala Pro Leu Gln
1               5                   10                  15

Pro Glu

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 18

Leu Tyr Ile Ser Ala Trp Pro Asp Ser Leu Pro Asp Leu Ser Val Phe
1               5                   10                  15

Gln Asn Leu Gln
            20

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 19

Leu Phe Arg Asn Pro His Gln Ala Leu Leu His Thr Ala Asn Arg Pro
1               5                   10                  15

Glu Asp Glu

<210> SEQ ID NO 20
<211> LENGTH: 34
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 20

Cys Leu Pro Cys His Pro Glu Cys Gln Pro Gln Asn Gly Ser Val Thr
1               5                   10                  15

Cys Phe Gly Pro Glu Ala Asp Gln Cys Val Ala Cys Ala His Tyr Lys
            20                  25                  30

Asp Pro

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 21

Lys Pro Asp Leu Ser Tyr Met Pro Ile Trp Lys Phe Pro Asp Glu Glu
1               5                   10                  15

Gly Ala

<210> SEQ ID NO 22

```
<211> LENGTH: 22
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 22

Ile Asn Gly Thr His Ser Cys Val Asp Leu Asp Asp Lys Gly Cys Pro
1               5                   10                  15

Ala Glu Gln Arg Ala Ser
            20

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 23

Cys His Pro Glu Cys Gln Pro Gln Asn Gly Ser Val Thr Cys Phe Gly
1               5                   10                  15

Pro Glu Ala Asp Gln Cys Val Ala Cys Ala His Tyr Lys Asp Pro Pro
            20                  25                  30

Phe Cys Val Ala
        35

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 24

Val Ala Cys Ala His Tyr Lys Asp Pro Pro Phe Cys Val Ala
1               5                   10

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 25

Val Ala Arg Cys Pro Ser Gly Val Lys Pro Asp Leu Ser Tyr Met Pro
1               5                   10                  15

Ile Trp Lys Phe Pro Asp Glu Glu Gly Ala Cys Gln Pro Leu
            20                  25                  30

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 26

Ile Trp Lys Phe Pro Asp Glu Glu Gly Ala Cys Gln Pro Leu
1               5                   10
```

<210> SEQ ID NO 27
<211> LENGTH: 31
<212> TYPE: PRT
<213> ORGANISM: Artificial Sequence
<220> FEATURE:
<223> OTHER INFORMATION: Description of Artificial Sequence: note = synthetic construct

<400> SEQUENCE: 27

Leu His Cys Pro Ala Leu Val Thr Tyr Asn Thr Asp Thr Phe Glu Ser
1               5                   10                  15

Met Pro Asn Pro Glu Gly Arg Tyr Thr Phe Gly Ala Ser Cys Val
            20                  25                  30

<210> SEQ ID NO 28
<211> LENGTH: 36
<212> TYPE: PRT
<213> ORGANISM: Artificial Sequence
<220> FEATURE:
<223> OTHER INFORMATION: Description of Artificial Sequence: note = synthetic construct

<400> SEQUENCE: 28

Ala Cys Pro Tyr Asn Tyr Leu Ser Thr Asp Val Gly Ser Cys Thr Leu
1               5                   10                  15

Val Cys Pro Leu His Asn Gln Glu Val Thr Ala Glu Asp Gly Thr Gln
            20                  25                  30

Arg Cys Glu Lys
        35

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: note = synthetic construct

<400> SEQUENCE: 29

Cys Pro Leu His Asn Gln Glu Val Thr Ala Glu Asp Gly Thr Gln Arg
1               5                   10                  15

Cys Glu Lys

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence: note = synthetic construct

<400> SEQUENCE: 30

Cys Pro Ile Asn Cys Thr His Ser Cys Val Asp Leu Asp Asp Lys Gly
1               5                   10                  15

Cys Pro Ala Glu Gln Arg Ala Ser
            20

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: note = synthetic construct

```
<400> SEQUENCE: 31

Lys Leu Leu Ser Leu Ile Lys Gly Val Ile Val His Arg Leu Glu Gly
1               5                   10                  15

Val Glu

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 32

Asn Ser Val Asp Asp Ala Leu Ile Asn Ser Thr Ile Tyr Ser Tyr Phe
1               5                   10                  15

Pro Ser Val

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 33

Pro Gly Ile Asn Gly Lys Ala Ile His Leu Val Asn Asn Gln Ser Ser
1               5                   10                  15

Glu

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 34

Gln Tyr Ile Lys Ala Asn Ser Lys Phe Ile Gly Ile Thr Glu Leu
1               5                   10                  15

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 35

Phe Asn Asn Phe Thr Val Ser Phe Trp Leu Arg Val Pro Lys Val Ser
1               5                   10                  15

Ala Ser His Leu Glu
            20

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: note =
      synthetic construct
```

```
<400> SEQUENCE: 36

Leu Ser Glu Ile Lys Gly Val Ile Val His Arg Leu Glu Gly Val
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 37

Phe Phe Leu Leu Thr Arg Ile Leu Thr Ile Pro Gln Ser Leu Asn
1               5                   10                  15

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 38

Thr Cys Gly Val Gly Val Arg Val Arg Ser Arg Val Asn Ala Ala Asn
1               5                   10                  15

Lys Lys Pro Glu
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 39

Ile Thr Met Gln Ile Met Arg Ile Lys Pro His Gln Gly Gln His Ile
1               5                   10                  15

Gly Glu Met Ser Phe
            20

<210> SEQ ID NO 40
<211> LENGTH: 23
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 40

Ile Thr Met Gln Cys Gly Ile His Gln Gly Gln His Pro Lys Ile Arg
1               5                   10                  15

Met Ile Cys Glu Met Ser Phe
            20

<210> SEQ ID NO 41
<211> LENGTH: 23
<212> TYPE: PRT
<213> ORGANISM: Artificial Sequence
<220> FEATURE:
<223> OTHER INFORMATION: Description of Atrificial Sequence: note =
      synthetic construct
```

<400> SEQUENCE: 41

Ile Thr Met Gln Cys Gly Ile His Gln Gly Gln His Pro Lys Ile Arg
1               5                   10                  15
Met Ile Cys Glu Met Ser Phe
                20